(12) United States Patent
Keil et al.

(10) Patent No.: US 7,732,440 B2
(45) Date of Patent: Jun. 8, 2010

(54) PHENOTHIAZIN DERIVATIVES, METHOD FOR THE PRODUCTION THEREOF AND USE THEREOF AS PHARMACEUTICALS

(75) Inventors: Stefanie Keil, Frankfurt am Main (DE); Elisabeth Defossa, Frankfurt am Main (DE); Karl Schoenafinger, Alzenau (DE); Dieter Schmoll, Frankfurt am Main (DE); Axel Deitrich, Frankfurt am Main (DE); Johanna Kuhlmann-Gottke, Frankfurt am Main (DE); Karl-Christian Engel, Frankfurt am Main (DE)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 12/507,202

(22) Filed: Jul. 22, 2009

(65) Prior Publication Data

US 2009/0325942 A1  Dec. 31, 2009

Related U.S. Application Data

(63) Continuation of application No. PCT/EP2008/000163, filed on Jan. 11, 2008.

(30) Foreign Application Priority Data

Jan. 26, 2007 (DE) .................. 10 2007 005 045
Aug. 31, 2007 (EP) .................. 07291062

(51) Int. Cl.
C07D 417/14 (2006.01)
A61K 31/5415 (2006.01)

(52) U.S. Cl. ...................... 514/225.2; 544/35
(58) Field of Classification Search ............. 544/35; 514/225.2
See application file for complete search history.

(56) References Cited

U.S. PATENT DOCUMENTS

2005/0288279 A1  12/2005  Rozman et al.

FOREIGN PATENT DOCUMENTS

WO   WO 02/062772   8/2002

*Primary Examiner*—Kahsay T Habte
(74) *Attorney, Agent, or Firm*—Jiang Lin

(57) ABSTRACT

The invention relates to compounds of the formula I,

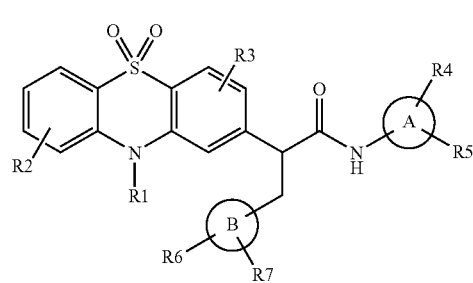

wherein R1, R2, R3, R4, R5, R6, R7, A and B are as defined herein, the pharmaceutical compositions and the uses as pharmaceuticals.

18 Claims, No Drawings

PHENOTHIAZIN DERIVATIVES, METHOD FOR THE PRODUCTION THEREOF AND USE THEREOF AS PHARMACEUTICALS

This application is a Continuation of International Application No. PCT/EP2008/000163, filed Jan. 11, 2008, which is incorporated herein by reference in its entirety.

FIELD OF THE INVENTION

The present invention relates to substituted phenothiazines and physiologically acceptable salts thereof.

BACKGROUND OF THE INVENTION

Phenothiazine derivatives such as, for example, chlorpromazine (3-(2-chloro-4-a,10a-dihydro-10H-phenothiazin-10-yl)-N,N-dimethylpropane-1-amine) are already known as neuroleptics.

It was an object of the present invention to develop compounds for the treatment of diabetes. In particular, these compounds should lower the blood glucose level.

SUMMARY OF THE INVENTION

Accordingly, the invention relates to compounds of the formula I,

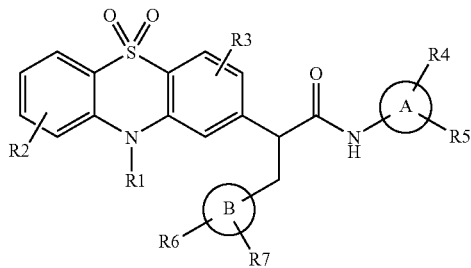

in which
R1 is H, $(C_1-C_6)$-alkyl, $(C_0-C_6)$-alkylene-aryl, CO—$(C_1-C_6)$-alkyl, $(C_2-C_6)$-alkylene-COO—$(C_0-C_6)$-alkyl, $(C_2-C_6)$-alkylene-O—$(C_1-C_6)$-alkyl;
R2, R3 independently of one another are H, F, Cl, Br, CN, $NO_2$, $(C_0-C_6)$-alkylene-COO—$(C_0-C_6)$-alkyl, $(C_0-C_6)$-alkylene-O—$(C_0-C_6)$-alkyl, $(C_1-C_6)$-alkyl, $(C_0-C_6)$-alkylene-CO—$(C_1-C_6)$-alkyl, $(C_0-C_6)$-alkylene-phenyl, $SCF_3$, $SF_5$, $SCH_3$;
R4, R5 independently of one another are H, F, Cl, Br, CN, SCN, $NO_2$, $(C_0-C_6)$-alkylene-COO—$(C_0-C_6)$-alkyl, —CO—COO—$(C_0-C_6)$-alkyl, $(C_0-C_6)$-alkylene-O—$(C_0-C_6)$-alkyl, $(C_1-C_6)$-alkyl, $(C_0-C_6)$-alkylene-CO—$(C_1-C_6)$-alkyl, $(C_0-C_6)$-alkylene-CONH$(C_0-C_6)$-alkyl, $(C_0-C_6)$-alkylene-CON[$(C_0-C_6)$-alkyl]$_2$, $(C_0-C_6)$-alkylene-NH$(C_0-C_6)$-alkyl, $(C_0-C_6)$-alkylene-NH—COO—$(C_0-C_6)$-alkyl, $(C_0-C_6)$-alkylene-CON[$(C_0-C_6)$-alkyl]-O—$(C_0-C_6)$-alkyl, $(C_0-C_6)$-alkylene-N[$(C_0-C_6)$-alkyl]$_2$, $(C_0-C_6)$-alkylene-aryl, $SF_5$, $(C_0-C_6)$-alkyl-S(O)$_x(C_1-C_6)$-alkyl, S(O)$_x(C_1-C_6)$-alkylene-COO—$(C_0-C_6)$-alkyl, S(O)$_x(C_2-C_6)$-alkylene-O—$(C_0-C_6)$-alkyl, —$SO_2$—NH—$(C_0-C_6)$-alkyl, —$SO_2$—N—[$(C_0-C_6)$-alkyl]$_2$, S(O)$_x(C_0-C_6)$-alkylene-heterocycle, S(O)$_x(C_1-C_6)$-alkylene-CO-heterocycle, —NH—$SO_2$—$(C_1-C_6)$-alkyl, $(C_0-C_6)$-alkylene-cycloalkyl, $(C_0-C_6)$-alkylene-heterocycle, $(C_0-C_6)$-alkylene-aryl;
x is 0, 1, 2;
R6, R7 independently of one another are H, F, Cl, Br, CN, $NO_2$, =O, =S, =N—O—$(C_0-C_6)$-alkyl, $(C_0-C_6)$-alkylene-COO—$(C_0-C_6)$-alkyl, $(C_0-C_6)$-alkylene-O—$(C_0-C_6)$-alkyl, $(C_0-C_6)$-alkyl, $(C_0-C_6)$-alkylene-O—CO—$(C_1-C_6)$-alkyl, $(C_1-C_6)$-alkyl, $(C_0-C_6)$-alkylene-CO—$(C_1-C_6)$-alkyl, $(C_0-C_6)$-alkylene-aryl, $SF_5$, $S(O)_n$—$(C_1-C_6)$-alkyl;
A is a 5- to 10-membered heterocycle, where the heterocycle may be fused to a further 5- to 10-membered ring;
B is a 4- to 8-membered cycloalkyl ring, a 4- to 10-membered heterocycle or a 6- to 10-membered aryl ring;

and physiologically acceptable salts thereof.

DETAILED DESCRIPTION OF THE INVENTION

Preference is given to compounds of the formula I in which one or more radicals have the following meaning:
R1 is H, $(C_1-C_6)$-alkyl, $(C_0-C_6)$-alkylene-aryl, CO—$(C_1-C_6)$-alkyl, $(C_2-C_6)$-alkylene-COO—$(C_0-C_6)$-alkyl, $(C_2-C_6)$-alkylene-O—$(C_1-C_6)$-alkyl;
R2, R3 independently of one another are H, F, Cl, Br, CN, $NO_2$, $(C_0-C_6)$-alkylene-COO—$(C_0-C_6)$-alkyl, $(C_0-C_6)$-alkylene-O—$(C_0-C_6)$-alkyl, $(C_1-C_6)$-alkyl, $(C_0-C_6)$-alkylene-CO—$(C_1-C_6)$-alkyl, $(C_0-C_6)$-alkylene-phenyl, $SCF_3$, $SF_5$, $SCH_3$;
R4, R5 independently of one another are H, F, Cl, Br, CN, SCN, $NO_2$, $(C_0-C_6)$-alkylene-COO—$(C_0-C_6)$-alkyl, —CO—COO—$(C_0-C_6)$-alkyl, $(C_0-C_6)$-alkylene-O—$(C_0-C_6)$-alkyl, $(C_1-C_6)$-alkyl, $(C_0-C_6)$-alkylene-CO—$(C_1-C_6)$-alkyl, $(C_0-C_6)$-alkylene-CONH$(C_0-C_6)$-alkyl, $(C_0-C_6)$-alkylene-CON[$(C_0-C_6)$-alkyl]$_2$, $(C_0-C_6)$-alkylene-NH$(C_0-C_6)$-alkyl, $(C_0-C_6)$-alkylene-NH—COO—$(C_0-C_6)$-alkyl, $(C_0-C_6)$-alkylene-CON[$(C_0-C_6)$-alkyl]-O—$(C_0-C_6)$-alkyl, $(C_0-C_6)$-alkylene-N[$(C_0-C_6)$-alkyl]$_2$, $(C_0-C_6)$-alkylene-aryl, $SF_5$, $(C_0-C_6)$-alkyl-S(O)$_x(C_1-C_6)$-alkyl, S(O)$_x(C_1-C_6)$-alkylene-COO—$(C_0-C_6)$-alkyl, S(O)$_x(C_2-C_6)$-alkylene-O—$(C_0-C_6)$-alkyl, —$SO_2$—NH—$(C_0-C_6)$-alkyl, —$SO_2$—N—[$(C_0-C_6)$-alkyl]$_2$, S(O)$_x(C_0-C_6)$-alkylene-heterocycle, S(O)$_x(C_1-C_6)$-alkylene-CO-heterocycle, —NH—$SO_2$—$(C_1-C_6)$-alkyl, $(C_0-C_6)$-alkylene-cycloalkyl, $(C_0-C_6)$-alkylene-heterocycle, $(C_0-C_6)$-alkylene-aryl;
x is 0, 1, 2;
R6, R7 independently of one another are H, F, Cl, Br, CN, $NO_2$, =O, =S, =N—O—$(C_0-C_6)$-alkyl, $(C_0-C_6)$-alkylene-COO—$(C_0-C_6)$-alkyl, $(C_0-C_6)$-alkylene-O—$(C_0-C_6)$-alkyl, $(C_0-C_6)$-alkyl, $(C_0-C_6)$-alkylene-O—CO—$(C_1-C_6)$-alkyl, $(C_1-C_6)$-alkyl, $(C_0-C_6)$-alkylene-CO—$(C_1-C_6)$-alkyl, $(C_0-C_6)$-alkylene-aryl, $SF_5$, $S(O)_n$—$(C_1-C_6)$-alkyl;
A is a 5- to 10-membered heterocycle which contains a —C=N— bond in the alpha position, where the heterocycle may be fused to a further 5- to 10-membered ring;
B is a 4- to 8-membered cycloalkyl ring, a 4- to 10-membered heterocycle or a 6- to 10-membered aryl ring;

and physiologically acceptable salts thereof.

Particular preference is given to compounds of the formula I in which one or more radicals have the following meaning:
R1 is H, $(C_1-C_6)$-alkyl, $(C_0-C_6)$-alkylene-aryl, CO—$(C_1-C_6)$-alkyl, $(C_2-C_6)$-alkylene-COO—$(C_0-C_6)$-alkyl, $(C_2-C_6)$-alkylene-O—$(C_1-C_6)$-alkyl;
R2, R3 are H;
R4, R5 independently of one another are H, F, Cl, Br, CN, SCN, $NO_2$, $(C_0-C_6)$-alkylene-COO—$(C_0-C_6)$-alkyl, —CO—COO—$(C_0-C_6)$-alkyl, $(C_0-C_6)$-alkylene-O—$(C_0-C_6)$-alkyl, $(C_1-C_6)$-alkyl, $(C_0-C_6)$-alkylene-CO—$(C_1-C_6)$-alkyl, $(C_0-C_6)$-alkylene-CONH$(C_0-C_6)$-alkyl, $(C_0-C_6)$- alkylene-CON[($C_0$-$C_6$)-alkyl]$_2$, ($C_0$-$C_6$)-alkylene-NH ($C_0$-$C_6$)-alkyl, ($C_0$-$C_6$)-alkylene-NH—COO—($C_0$-$C_6$)-alkyl, ($C_0$-$C_6$)-alkylene-CON[($C_0$-$C_6$)-alkyl]-O—($C_0$-$C_6$)-alkyl, ($C_0$-$C_6$)-alkylene-N [($C_0$-$C_6$)-alkyl]$_2$, ($C_0$-$C_6$)-alkylene-aryl, $SF_5$, ($C_0$-$C_6$)-alkyl-S(O)$_x$($C_1$-$C_6$)-alkyl, S(O)$_x$($C_1$-$C_6$)-alkylene-COO—($C_0$-$C_6$)-alkyl, S(O)$_x$($C_2$-$C_6$)-alkylene-O—($C_0$-$C_6$)-alkyl, —SO$_2$—NH—($C_0$-$C_6$)-alkyl, —SO$_2$—N—[($C_0$-$C_6$)-alkyl]$_2$, S(O)$_x$($C_0$-$C_6$)-alkylene-heterocycle, S(O))($C_1$-$C_6$)-alkylene-CO-heterocycle, —NH—SO$_2$—($C_1$-$C_6$)-alkyl, ($C_0$-$C_6$)-alkylene-cycloalkyl, ($C_0$-$C_6$)-alkylene-heterocycle, ($C_0$-$C_6$)-alkylene-aryl;

x is 0, 1, 2;

R6, R7 independently of one another are H, F, Cl, Br, CN, NO$_2$, =O, =S, =N—O—($C_0$-$C_6$)-alkyl, ($C_0$-$C_6$)-alkylene-COO—($C_0$-$C_6$)-alkyl, ($C_0$-$C_6$)-alkylene-O—($C_0$-$C_6$)-alkyl, ($C_0$-$C_6$)-alkylene-O—CO—($C_1$-$C_6$)-alkyl, ($C_1$-$C_6$)-alkyl, ($C_0$-$C_6$)-alkylene-CO—($C_1$-$C_6$)-alkyl, ($C_0$-$C_6$)-alkylene-aryl, $SF_5$, S(O)$_x$—($C_1$-$C_6$)-alkyl;

A is a 5-membered heterocycle which contains a —C=N— bond in the alpha position, where the heterocycle may be fused to a further 5- to 10-membered ring;

B is 4- to 8-membered cycloalkyl ring, a 4- to 10-membered heterocycle or a 6- to 10-membered aryl ring;

and physiologically acceptable salts thereof.

Very particular preference is given to compounds of the formula I in which one or more radicals have the following meaning:

R1 is H, ($C_1$-$C_6$)-alkyl, ($C_0$-$C_6$)-alkylene-aryl, CO—($C_1$-$C_6$)-alkyl, ($C_2$-$C_6$)-alkyl ene-COO—($C_0$-$C_6$)-alkyl, ($C_2$-$C_6$)-alkylene-O—($C_1$-$C_6$)-alkyl;

R2, R3 are H;

R4, R5 independently of one another are H, F, Cl, Br, CN, SCN, NO$_2$, ($C_0$-$C_6$)-alkylene-COO—($C_0$-$C_6$)-alkyl, —CO—COO—($C_0$-$C_6$)-alkyl, ($C_0$-$C_6$)-alkylene-O—($C_0$-$C_6$)-alkyl, ($C_1$-$C_6$)-alkyl, ($C_0$-$C_6$)-alkylene-CO—($C_1$-$C_6$)-alkyl, ($C_0$-$C_6$)-alkylene-CONH($C_0$-$C_6$)-alkyl, ($C_0$-$C_6$)-alkylene-CON[($C_0$-$C_6$)-alkyl]$_2$, ($C_0$-$C_6$)-alkylene-NH ($C_0$-$C_6$)-alkyl, ($C_0$-$C_6$)-alkylene-NH—COO—($C_0$-$C_6$)-alkyl, ($C_0$-$C_6$)-alkylene-CON[($C_0$-$C_6$)-alkyl]-O—($C_0$-$C_6$)-alkyl, ($C_0$-$C_6$)-alkylene-N[($C_0$-$C_6$)-alkyl]$_2$, ($C_0$-$C_6$)-alkylene-aryl, $SF_5$, ($C_0$-$C_6$)-alkyl-S(O)$_x$($C_1$-$C_6$)-alkyl, S(O)$_x$($C_1$-$C_6$)-alkylene-COO—($C_0$-$C_6$)-alkyl, S(O)$_x$($C_2$-$C_6$)-alkylene-O—($C_0$-$C_6$)-alkyl, —SO$_2$—NH—($C_0$-$C_6$)-alkyl, —SO$_2$—N—[($C_0$-$C_6$)-alkyl]$_2$, S(O)$_x$($C_0$-$C_6$)-alkylene-heterocycle, S(O)$_x$($C_1$-$C_6$)-alkylene-CO-heterocycle, —NH—SO$_2$—($C_1$-$C_6$)-alkyl, ($C_0$-$C_6$)-alkyl ene-cycloalkyl, ($C_0$-$C_6$)-alkylene-heterocycle, ($C_0$-$C_6$)-alkylene-aryl;

x is 0, 1, 2;

R6, R7 independently of one another are H, F, Cl, Br, CN, NO$_2$, =O, =S, =N—O—($C_0$-$C_6$)-alkyl, ($C_0$-$C_6$)-alkylene-COO—($C_0$-$C_6$)-alkyl, ($C_0$-$C_6$)-alkylene-O—($C_0$-$C_6$)-alkyl, ($C_0$-$C_6$)-alkylene-O—CO—($C_1$-$C_6$)-alkyl, ($C_1$-$C_6$)-alkyl, ($C_0$-$C_6$)-alkylene-CO—($C_1$-$C_6$)-alkyl, ($C_0$-$C_6$)-alkylene-aryl, $SF_5$, S(O)$_n$—($C_1$-$C_6$)-alkyl;

A is thiazol-2-yl, pyrazol-3-yl, pyridin-2-yl, oxazol-2-yl, isoxazol-3-yl, imidazol-2-yl, [1,2,4]thiadiazol-3-yl, [1,2,4]thiadiazol-5-yl, [1,3,4]thiadiazol-3-yl, pyridin-2-yl, pyrimidin-2-yl, pyrimidin-4-yl, pyrazin-2-yl, pyridazin-2-yl, [1,2,4]triazin-3-yl, [1,2,4]triazin-6-yl, thiazolo[4,5-b]pyridin-2-yl, thieno[2,3-d]thiazol-2-yl, benzothiazol-2-yl, benzoxazol-2-yl, benzimidazol-2-yl, quinolin-2-yl, isoquinolin-3-yl, 4,5,6,7-tetrahydro-benzothiazol-2-yl, 4,5,6,7-tetrahydrobenzoxazol-2-yl, 4,5,6,7-tetrahydro-benzimidazol-2-yl, 4,5,6,7-tetrahydropyrazolo[1,5-a]pyridin-2-yl, 5,6-dihydro-4H-cyclopentathiazol-2-yl, 4,5-dihydrothiazol-2-yl;

B is cyclopentyl, cyclohexyl, cyclohexenyl, tetrahydrofuranyl, tetrahydropyranyl, tetrahydrothiopyranyl, tetrahydrothiophene, piperidinyl, phenyl, pyridyl, furanyl, thiophenyl, thiazolyl, indanyl, oxetanyl, oxazolyl, pyrazolyl, isoxazolyl;

and physiologically acceptable salts thereof.

Very particular preference is furthermore given to compounds of the formula I in which one or more radicals have the following meaning:

R1 is H, ($C_1$-$C_6$)-alkyl, ($C_0$-$C_6$)-alkylene-aryl, CO—($C_1$-$C_6$)-alkyl, ($C_2$-$C_6$)-alkyl ene-COO—($C_0$-$C_6$)-alkyl, ($C_2$-$C_6$)-alkylene-O—($C_1$-$C_6$)-alkyl;

R2, R3 are H;

R4, R5 independently of one another are H, F, Cl, Br, CN, SCN, NO$_2$, ($C_0$-$C_6$)-alkylene-COO—($C_0$-$C_6$)-alkyl, —CO—COO—($C_0$-$C_6$)-alkyl, ($C_0$-$C_6$)-alkylene-O—($C_0$-$C_6$)-alkyl, ($C_1$-$C_6$)-alkyl, ($C_0$-$C_6$)-alkylene-CO—($C_1$-$C_6$)-alkyl, ($C_0$-$C_6$)-alkylene-CONH($C_0$-$C_6$)-alkyl, ($C_0$-$C_6$)-alkylene-CON[($C_0$-$C_6$)-alkyl]$_2$, ($C_0$-$C_6$)-alkylene-NH ($C_0$-$C_6$)-alkyl, ($C_0$-$C_6$)-alkylene-NH—COO—($C_0$-$C_6$)-alkyl, ($C_0$-$C_6$)-alkylene-CON[($C_0$-$C_6$)-alkyl]-O—($C_0$-$C_6$)-alkyl, ($C_0$-$C_6$)-alkylene-N [($C_0$-$C_6$)-alkyl]$_2$, ($C_0$-$C_6$)-alkylene-aryl, $SF_5$, ($C_0$-$C_6$)-alkyl-S(O)$_x$($C_1$-$C_6$)-alkyl, S(O)$_x$($C_1$-$C_6$)-alkylene-COO—($C_0$-$C_6$)-alkyl, S(O)$_x$($C_2$-$C_6$)-alkylene-O—($C_0$-$C_6$)-alkyl, —SO$_2$—NH—($C_0$-$C_6$)-alkyl, —SO$_2$—N—[($C_0$-$C_6$)-alkyl]$_2$, S(O)$_x$($C_0$-$C_6$)-alkylene-heterocycle, S(O)$_x$($C_1$-$C_6$)-alkylene-CO-heterocycle, —NH—SO$_2$—($C_1$-$C_6$)-alkyl, ($C_0$-$C_6$)-alkyl ene-cycloalkyl, ($C_0$-$C_6$)-alkylene-heterocycle, ($C_0$-$C_6$)-alkylene-aryl;

x is 0, 1, 2;

R6, R7 independently of one another are H, F, Cl, Br, CN, NO$_2$, =O, =S, =N—O—($C_0$-$C_6$)-alkyl, ($C_0$-$C_6$)-alkylene-COO—($C_0$-$C_6$)-alkyl, ($C_0$-$C_6$)-alkylene-O—($C_0$-$C_6$)-alkyl, ($C_0$-$C_6$)-alkylene-O—CO—($C_1$-$C_6$)-alkyl, ($C_1$-$C_6$)-alkyl, ($C_0$-$C_6$)-alkylene-CO—($C_1$-$C_6$)-alkyl, ($C_0$-$C_6$)-alkylene-aryl, $SF_5$, S(O)$_n$—($C_1$-$C_6$)-alkyl;

A is thiazol-2-yl, pyrazol-3-yl, pyridin-2-yl, oxazol-2-yl, isoxazol-3-yl, imidazol-2-yl, [1,2,4]thiadiazol-3-yl, [1,2,4]thiadiazol-5-yl, [1,3,4]thiadiazol-3-yl, pyridin-2-yl, pyrimidin-2-yl, pyrimidin-4-yl, pyrazin-2-yl, pyridazin-2-yl, [1,2,4]triazin-3-yl, [1,2,4]triazin-6-yl, thiazolo[4,5-b]pyridin-2-yl, thieno[2,3-d]thiazol-2-yl, benzothiazol-2-yl, benzoxazol-2-yl, benzimidazol-2-yl, quinolin-2-yl, isoquinolin-3-yl, 4,5,6,7-tetrahydro-benzothiazol-2-yl, 4,5,6,7-tetrahydrobenzoxazol-2-yl, 4,5,6,7-tetrahydro-benzimidazol-2-yl, 4,5,6,7-tetrahydropyrazolo[1,5-a]pyridin-2-yl, 5,6-dihydro-4H-cyclopentathiazol-2-yl, 4,5-dihydrothiazol-2-yl;

B is cyclopentyl, cyclohexyl, tetrahydrofuranyl, tetrahydropyranyl, tetrahydrothiopyranyl, piperidinyl, phenyl, pyridyl, furanyl, thiophenyl, thiazolyl, oxazolyl, pyrazolyl, isoxazolyl;

and physiologically acceptable salts thereof.

Very particular preference is furthermore given to compounds of the formula I in which one or more radicals have the following meaning:

R1 is H, ($C_1$-$C_6$)-alkyl;

R2, R3 are H;

R4 is H, F, Cl, Br, ($C_0$-$C_6$)-alkylene-COO—($C_0$-$C_6$)-alkyl, ($C_0$-$C_6$)-alkylene-O—($C_0$-$C_6$)-alkyl, =O, ($C_1$-$C_6$)-alkyl, ($C_0$-$C_6$)-alkylene-aryl;

R5 is H;

R6 is H;

R7 is H, F, Cl, Br, =O, =N—O—($C_0$-$C_6$)-alkyl, ($C_1$-$C_6$)-alkyl;

A is thiazol-2-yl, pyrazol-3-yl, isoxazol-3-yl, [1,2,4]thiadiazol-3-yl, [1,2,4]thiadiazol-5-yl, [1,3,4]thiadiazol-3-yl, pyridazin-2-yl, thiazolo[4,5-b]pyridin-2-yl, thieno[2,3-d]thiazol-2-yl;

B is cyclopentyl, cyclohexyl, cyclohexenyl, tetrahydrofuranyl, tetrahydropyranyl, tetrahydrothiophenyl, oxetanyl, piperidinyl, indanyl;

and physiologically acceptable salts thereof.

In one embodiment, preference is given to compounds of the formula I in which R1 is H.

In one embodiment, preference is given to compounds of the formula I in which R1 is methyl.

In one embodiment, preference is given to compounds of the formula I in which A is thiazol-2-yl.

In one embodiment, preference is given to compounds of the formula I in which A is pyrazol-3-yl.

In one embodiment, preference is given to compounds of the formula I in which A is isoxazol-3-yl.

In one embodiment, preference is given to compounds of the formula I in which A is [1,2,4]thiadiazol-3-yl, [1,2,4]thiadiazol-5-yl or [1,3,4]thiadiazol-3-yl.

In one embodiment, preference is given to compounds of the formula I in which A is pyridazin-2-yl.

In one embodiment, preference is given to compounds of the formula I in which A is thiazolo[4,5-b]pyridin-2-yl.

In one embodiment, preference is given to compounds of the formula I in which A is thieno[2,3-d]thiazol-2-yl.

In one embodiment, preference is given to compounds of the formula I in which B is cyclopentyl.

In one embodiment, preference is given to compounds of the formula I in which B is cyclohexyl.

In one embodiment, preference is given to compounds of the formula I in which B is cyclohexenyl.

In one embodiment, preference is given to compounds of the formula I in which B is tetrahydrofuranyl.

In one embodiment, preference is given to compounds of the formula I in which B is tetrahydropyranyl.

In one embodiment, preference is given to compounds of the formula I in which B is tetrahydrothiophenyl.

In one embodiment, preference is given to compounds of the formula I in which B is oxetanyl.

In one embodiment, preference is given to compounds of the formula I in which B is piperidinyl.

In one embodiment, preference is given to compounds of the formula I in which B is indanyl.

In one embodiment, preference is given to compounds of the formula I in which R6 is H.

In one embodiment, preference is given to compounds of the formula I in which R6 is ($C_1$-$C_6$)-alkyl.

In one embodiment, preference is given to compounds of the formula I in which R6 is =O.

In one embodiment, preference is given to compounds of the formula I in which R6 is —OH.

In one embodiment, preference is given to compounds of the formula I in which R6 is =NOH.

In one embodiment, preference is given to compounds of the formula I in which R6 is F, Cl or Br.

In one embodiment, preference is given to compounds of the formula I in which R7 is H.

In one embodiment, preference is given to compounds of the formula I in which R7 is =O.

In one embodiment, preference is given to compounds of the formula I in which R4 is F, Cl or Br.

In one embodiment, preference is given to compounds of the formula I in which R4 is H.

In one embodiment, preference is given to compounds of the formula I in which R4 is ($C_1$-$C_6$)-alkyl.

In one embodiment, preference is given to compounds of the formula I in which R4 is =O.

In one embodiment, preference is given to compounds of the formula I in which R4 is ($C_0$-$C_6$)-alkylene-COO—($C_0$-$C_6$)-alkyl.

In one embodiment, preference is given to compounds of the formula I in which R4 is ($C_0$-$C_6$)-alkylene-O—($C_0$-$C_6$)-alkyl.

In one embodiment, preference is given to compounds of the formula I in which R4 is benzyl.

The invention relates to compounds of the formula I in the form of their racemates, racemic mixtures and pure enantiomers and also to their diastereomers and mixtures thereof.

If radicals or substituents may be present more than once in the compounds of the formula I, they may all independently of one another have the given meanings and may be identical or different.

The definition ($C_0$-$C_6$)-alkylene- is to be understood as meaning that either a bond or a ($C_1$-$C_6$)-alkylene group may be present.

The definition —($C_0$-$C_6$)-alkyl is to be understood as meaning that either a hydrogen or a ($C_1$-$C_6$)-alkyl group may be present.

"Fusing" or "fused" is to be understood as meaning that a further ring system is fused on. The further fused-on ring system may be aromatic or nonaromatic and carbocyclic or heterocyclic.

Pharmaceutically acceptable salts are, because their solubility in water is greater than that of the initial or basic compounds, particularly suitable for medical applications. These salts must have a pharmaceutically acceptable anion or cation. Suitable pharmaceutically acceptable acid addition salts of the compounds of the invention are salts of inorganic acids such as hydrochloric acid, hydrobromic, phosphoric, metaphosphoric, nitric and sulfuric acids, and organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acids. Suitable pharmaceutically acceptable basic salts are ammonium salts, alkali metal salts (such as sodium and potassium salts), alkaline earth metal salts (such as magnesium and calcium salts), trometamol (2-amino-2-hydroxymethyl-1,3-propanediol), diethanolamine, lysine or ethylenediamine salt.

Salts with a pharmaceutically unacceptable anion such as, for example, trifluoroacetate likewise belong within the framework of the invention as useful intermediates for preparing or purifying pharmaceutically acceptable salts and/or for use in nontherapeutic, for example in vitro applications.

A further aspect of the invention are the physiologically functional derivatives of the compounds of the formula I. The term "physiologically functional derivative" used here refers to all physiologically acceptable derivatives of a compound of the formula I according to the invention, for example an ester, which, when administered to a mammal such as, for example, man is able to form (directly or indirectly) a compound of the formula I or an active metabolite thereof.

The physiologically functional derivatives also include prodrugs of the compounds according to the invention such as, for example, those described in H. Okada et al., Chem. Pharm. Bull. 1994, 42, 57-61. Such prodrugs can be metabolized in vivo to a compound according to the invention. For their part, these prodrugs may be active or not.

The compounds of the invention may also exist in various polymorphous forms, for example as amorphous and crystalline polymorphous forms. All polymorphous forms of the compounds according to the invention belong within the framework of the invention and are a further aspect of the invention.

All references to "compound(s) of formula I" hereinafter refer to compound(s) of the formula I as described hereinabove, and the salts, solvates and physiologically functional derivatives thereof as described herein.

An alkyl radical means a straight-chain or branched hydrocarbon chain having one or more carbons such as, for example, methyl, ethyl, isopropyl, tert-butyl, hexyl. The alkyl radicals may be mono- or polysubstituted by suitable groups such as, for example: F, Cl, Br, I, $CF_3$, $NO_2$, $N_3$, CN, COOH, $COO(C_1-C_6)$-alkyl, $CONH_2$, $CONH(C_1-C_6)$-alkyl, $CON[(C_1-C_6)$-alkyl$]_2$ cycloalkyl, $(C_2-C_6)$-alkenyl, $(C_2-C_6)$-alkynyl, O—$(C_1-C_6)$-alkyl, O—CO—$(C_1-C_6)$-alkyl, O—CO—$(C_1-C_6)$-aryl, O—CO—$(C_1-C_6)$-heterocycle; $PO_3H_2$, $SO_3H$, $SO_2$—$NH_2$, $SO_2NH(C_1-C_6)$-alkyl, $SO_2N[(C_1-C_6)$-alkyl$]_2$, S—$(C_1-C_6)$-alkyl, S—$(CH_2)_n$-aryl, S—$(CH_2)_n$-heterocycle, SO—$(C_1-C_6)$-alkyl, SO—$(CH_2)_n$-aryl, SO—$(CH_2)_n$-heterocycle, $SO_2$—$(C_1-C_6)$-alkyl, $SO_2$—$(CH_2)_n$-aryl, $SO_2$—$(CH_2)_n$-heterocycle, $SO_2$—$NH(CH_2)_n$-aryl, $SO_2$—$NH(CH_2)_n$-heterocycle, $SO_2$—$N((C_1-C_6)$-alkyl$)(CH_2)_n$-aryl, $SO_2$—$N((C_1-C_6)$-alkyl$)(CH_2)_n$-heterocycle, $SO_2$—$N((CH_2)_n$-aryl$)_2$, $SO_2$—$N((CH_2)_n$-heterocycle$)_2$ where n=0-6 and where the aryl radical or the heterocyclic radical may be substituted up to two times by F, Cl, Br, OH, $CF_3$, $NO_2$, CN, $OCF_3$, O—$(C_1-C_6)$-alkyl, $(C_1-C_6)$-alkyl, $NH_2$;

$C(NH)(NH_2)$, $NH_2$, NH—$(C_1-C_6)$-alkyl, $N((C_1-C_6)$-alkyl$)_2$, $NH(C_2-C_7)$-acyl, NH—CO—$(C_1-C_6)$-alkyl, NH—COO—$(C_1-C_6)$-alkyl, NH—CO-aryl, NH—CO-heterocycle, NH—COO-aryl, NH—COO-heterocycle, NH—CO—NH—$(C_1-C_6)$-alkyl, NH—CO—NH-aryl, NH—CO—NH-heterocycle, $N[(C_1-C_6)$-alkyl]-CO—$(C_1-C_6)$-alkyl, $N[(C_1-C_6)$-alkyl]-COO—$(C_1-C_6)$-alkyl, $N[(C_1-C_6)$-alkyl]-CO-aryl, $N[(C_1-C_6)$-alkyl]-CO-heterocycle, $N(C_1-C_6)$-alkyl-COO-aryl, $N[(C_1-C_6)$-alkyl]-COO-heterocycle, $N[(C_1-C_6)$-alkyl]-CO—NH—$(C_1-C_6)$-alkyl), $N[(C_1-C_6)$-alkyl]-CO—NH-aryl, $N[(C_1-C_6)$-alkyl]-CO—NH-heterocycle, $N[(C_1-C_6)$-alkyl]-CO—N—$[(C_1-C_6)$-alkyl$]_2$, $N[(C_1-C_6)$-alkyl]-CO—N$[(C_1-C_6)$-alkyl)]-aryl, $N[(C_1-C_6)$-alkyl]-CO—$N[(C_1-C_6)$-alkyl]-heterocycle, $N[(C_1-C_6)$-alkyl]-CO—N-(aryl)$_2$, $N[(C_1-C_6)$-alkyl]-CO—N-(heterocycle)$_2$, N(aryl)-CO—$(C_1-C_6)$-alkyl, N(heterocycle)-CO—$(C_1-C_6)$-alkyl, N(aryl)-COO—$(C_1-C_6)$-alkyl, N(heterocycle)-COO—$(C_1-C_6)$-alkyl, N(aryl)-CO-aryl, N(heterocycle)-CO-aryl, N(aryl)-COO-aryl, N(heterocycle)-COO-aryl, N(aryl)-CO—NH—$(C_1-C_6)$-alkyl), N(heterocycle)-CO—NH—$(C_1-C_6)$-alkyl, N(aryl)-CO—NH-aryl, N(heterocycle)-CO—NH-aryl, N(aryl)-CO—N—$[(C_1-C_6)$-alkyl$]_2$, N(heterocycle)-CO—N—$[(C_1-C_6)$-alkyl$]_2$, N(aryl)-CO—$N[(C_1-C_6)$-alkyl]-aryl, N(heterocycle)-CO—$N[(C_1-C_6)$-alkyl]-aryl, N (aryl)-CO—N-(aryl)$_2$, N (heterocycle)-CO—N-(aryl)$_2$, aryl, O—$(CH_2)_n$-aryl, O—$(CH_2)_n$-heterocycle, where n=0-6 and where the aryl radical or heterocyclic radical may be mono- to trisubstituted by F, Cl, Br, I, OH, $CF_3$, $NO_2$, CN, $OCF_3$, O—$(C_1-C_6)$-alkyl, $(C_1-C_6)$-alkyl, $NH_2$, $NH(C_1-C_6)$-alkyl, $N[(C_1-C_6)$-alkyl$]_2$, $SO_2$—$CH_3$, COOH, COO—$(C_1-C_6)$-alkyl or $CONH_2$.

An alkynyl radical is to be understood as meaning a straight-chain or branched hydrocarbon chain having two or more carbons and also one or more tripple bonds such as, for example, ethynyl, propynyl, hexynyl.

The alkynyl radicals may be mono- or polysubstituted by suitable groups such as, for example: F, Cl, Br, I, $CF_3$, $NO_2$, $N_3$, CN, COOH, $COO(C_1-C_6)$-alkyl, $CONH_2$, $CONH(C_1-C_6)$-alkyl, $CON[(C_1-C_6)$-alkyl$]_2$, cycloalkyl, $(C_2-C_6)$-alkenyl, $(C_2-C_6)$-alkynyl, O—$(C_1-C_6)$-alkyl, O—CO—$(C_1-C_6)$-alkyl, O—CO—$(C_1-C_6)$-aryl, O—CO—$(C_1-C_6)$-heterocycle; $PO_3H_2$, $SO_3H$, $SO_2$—$NH_2$, $SO_2NH(C_1-C_6)$-alkyl, $SO_2N[(C_1-C_6)$-alkyl$]_2$, S—$(C_1-C_6)$-alkyl, S—$(CH_2)_n$-aryl, S—$(CH_2)_n$-heterocycle, SO—$(C_1-C_6)$-alkyl, SO—$(CH_2)_n$-aryl, SO—$(CH_2)_n$-heterocycle, $SO_2$—$(C_1-C_6)$-alkyl, $SO_2$—$(CH_2)_n$-aryl, $SO_2$—$(CH_2)_n$-heterocycle, $SO_2$—NH$(CH_2)_n$-aryl, $SO_2$—$NH(CH_2)_n$-heterocycle, $SO_2$—$N((C_1-C_6)$-alkyl$)(CH_2)_n$-aryl, $SO_2$—$N((C_1-C_6)$-alkyl$)(CH_2)_n$-heterocycle, $SO_2-N((CH_2)_n$-aryl$)_2$, $SO_2-N((CH_2)_n$-heterocycle$)_2$ where n=0-6 and where the aryl radical or the heterocyclic radical may be substituted up to two times by F, Cl, Br, OH, $CF_3$, $NO_2$, CN, $OCF_3$, $O-(C_1-C_6)$-alkyl, $(C_1-C_6)$-alkyl, $NH_2$;

$C(NH)(NH_2)$, $NH_2$, $NH-(C_1-C_6)$-alkyl, $N((C_1-C_6)$-alkyl$)_2$, $NH(C_2-C_7)$-acyl, $NH-CO-(C_1-C_6)$-alkyl, $NH-COO-(C_1-C_6)$-alkyl, NH—CO-aryl, NH—CO-heterocycle, NH—COO-aryl, NH—COO-heterocycle, $NH-CO-NH-(C_1-C_6)$-alkyl, NH—CO—NH-aryl, NH—CO—NH-heterocycle, $N[(C_1-C_6)$-alkyl$]$-$CO-(C_1-C_6)$-alkyl, $N[(C_1-C_6)$-alkyl$]$-$COO-(C_1-C_6)$-alkyl, $N[(C_1-C_6)$-alkyl$]$-CO-aryl, $N[(C_1-C_6)$-alkyl$]$-CO-heterocycle, $N(C_1-C_6)$-alkyl-COO-aryl, $N[(C_1-C_6)$-alkyl$]$-COO-heterocycle, $N[(C_1-C_6)$-alkyl$]$-$CO-NH-(C_1-C_6)$-alkyl), $N[(C_1-C_6)$-alkyl$]$-CO—NH-aryl, $N[(C_1-C_6)$-alkyl$]$-CO—NH-heterocycle, $N[(C_1-C_6)$-alkyl$]$-$CO-N-[(C_1-C_6)$-alkyl$]_2$, $N[(C_1-C_6)$-alkyl$]$-CO—N$[(C_1-C_6)$-alkyl$)]$-aryl, $N[(C_1-C_6)$-alkyl$]$-$CO-N[(C_1-C_6)$-alkyl$]$-heterocycle, $N[(C_1-C_6)$-alkyl$]$-CO—N-(aryl$)_2$, $N[(C_1-C_6)$-alkyl$]$-CO—N-(heterocycle$)_2$, N(aryl)-CO—$(C_1-C_6)$-alkyl, N(heterocycle)-CO—$(C_1-C_6)$-alkyl, N(aryl)-COO—$(C_1-C_6)$-alkyl, N(heterocycle)-COO—$(C_1-C_6)$-alkyl, N (aryl)-CO-aryl, N(heterocycle)-CO-aryl, N(aryl)-COO-aryl, N(heterocycle)-COO-aryl, N(aryl)-CO—NH—$(C_1-C_6)$-alkyl), N(heterocycle)-CO—NH—$(C_1-C_6)$-alkyl, N(aryl)-CO—NH-aryl, N (heterocycle)-CO—NH-aryl, N(aryl)-CO—N—$[(C_1-C_6)$-alkyl$]_2$, N(heterocycle)-CO—N—$[(C_1-C_6)$-alkyl$]_2$, N(aryl)-CO—N$[(C_1-C_6)$-alkyl$]$-aryl, N(heterocycle)-CO—N$[(C_1-C_6)$-alkyl$]$-aryl, N(aryl)-CO—N-(aryl$)_2$, N(heterocycle)-CO—N-(aryl$)_2$, aryl, O—$(CH_2)_n$-aryl, O—$(CH_2)_n$-heterocycle, where n=0-6 and where the aryl radical or heterocyclic radical may be mono- to trisubstituted by F, Cl, Br, I, OH, $CF_3$, $NO_2$, CN, $OCF_3$, $O-(C_1-C_6)$-alkyl, $(C_1-C_6)$-alkyl, $NH_2$, $NH(C_1-C_6)$-alkyl, $N[(C_1-C_6)$-alkyl$]_2$, $SO_2-CH_3$, COOH, COO—$(C_1-C_6)$-alkyl or $CONH_2$.

An aryl radical is to be understood as meaning a phenyl, naphthyl, biphenyl, tetrahydronaphthyl, alpha- or beta-tetralone, indanyl- or indan-1-onyl radical.

The aryl radicals may be mono- or polysubstituted by suitable groups such as, for example: F, Cl, Br, I, $CF_3$, $NO_2$, $N_3$, CN, COOH, $COO(C_1-C_6)$-alkyl, $CONH_2$, $CONH(C_1-C_6)$-alkyl, $CON[(C_1-C_6)$-alkyl$]_2$, cycloalkyl, $(C_2-C_6)$-alkenyl, $(C_2-C_6)$-alkynyl, $O-(C_1-C_6)$-alkyl, $O-CO-(C_1-C_6)$-alkyl, $O-CO-(C_1-C_6)$-aryl, $O-CO-(C_1-C_6)$-heterocycle; $PO_3H_2$, $SO_3H$, $SO_2-NH_2$, $SO_2NH(C_1-C_6)$-alkyl, $SO_2N[(C_1-C_6)$-alkyl$]_2$, $S-(C_1-C_6)$-alkyl, $S-(CH_2)_n$-aryl, $S-(CH_2)_n$-heterocycle, $SO-(C_1-C_6)$-alkyl, SO—$(CH_2)_n$-aryl, SO—$(CH_2)_n$-heterocycle, $SO_2-(C_1-C_6)$-alkyl, $SO_2-(CH_2)_n$-aryl, $SO_2-(CH_2)_n$-heterocycle, $SO_2-NH(CH_2)_n$-aryl, $SO_2-NH(CH_2)_n$-heterocycle, $SO_2-N((C_1-C_6)$-alkyl$)(CH_2)_n$-aryl, $SO_2-N((C_1-C_6)$-alkyl$)(CH_2)_n$-heterocycle, $SO_2-N((CH_2)_n$-aryl$)_2$, $SO_2-N((CH_2)_n$-heterocycle$)_2$ where n=0-6 and where the aryl radical or the heterocyclic radical may be substituted up to two times by F, Cl, Br, OH, $CF_3$, $NO_2$, CN, $OCF_3$, $O-(C_1-C_6)$-alkyl, $(C_1-C_6)$-alkyl, $NH_2$;

$C(NH)(NH_2)$, $NH_2$, $NH-(C_1-C_6)$-alkyl, $N((C_1-C_6)$-alkyl$)_2$, $NH(C_2-C_7)$-acyl, $NH-CO-(C_1-C_6)$-alkyl, $NH-COO-(C_1-C_6)$-alkyl, NH—CO-aryl, NH—CO-heterocycle, NH—COO-aryl, NH—COO-heterocycle, $NH-CO-NH-(C_1-C_6)$-alkyl, NH—CO—NH-aryl, NH—CO—NH-heterocycle, $N[(C_1-C_6)$-alkyl$]$-$CO-(C_1-C_6)$-alkyl, $N[(C_1-C_6)$-alkyl$]$-$COO-(C_1-C_6)$-alkyl, $N[(C_1-C_6)$-alkyl$]$-CO-aryl, $N[(C_1-C_6)$-alkyl$]$-CO-heterocycle, $N(C_1-C_6)$-alkyl-COO-aryl, $N[(C_1-C_6)$-alkyl$]$-COO-heterocycle, $N[(C_1-C_6)$-alkyl$]$-$CO-NH-(C_1-C_6)$-alkyl), $N[(C_1-C_6)$-alkyl$]$-CO—NH-aryl, $N[(C_1-C_6)$-alkyl$]$-CO—NH-heterocycle, $N[(C_1-C_6)$-alkyl$]$-$CO-N-[(C_1-C_6)$-alkyl$]_2$, $N[(C_1-C_6)$-alkyl$]$-CO—N$[(C_1-C_6)$-alkyl$)]$-aryl, $N[(C_1-C_6)$-alkyl$]$-$CO-N[(C_1-C_6)$-alkyl$]$-heterocycle, $N[(C_1-C_6)$-alkyl$]$-CO—N-(aryl$)_2$, $N[(C_1-C_6)$-alkyl$]$-CO—N-(heterocycle$)_2$, N(aryl)-CO—$(C_1-C_6)$-alkyl, N(heterocycle)-CO—$(C_1-C_6)$-alkyl, N (aryl)-COO—$(C_1-C_6)$-alkyl, N(heterocycle)-COO—$(C_1-C_6)$-alkyl, N (aryl)-CO-aryl, N(heterocycle)-CO-aryl, N(aryl)-COO-aryl, N(heterocycle)-COO-aryl, N(aryl)-CO—NH—$(C_1-C_6)$-alkyl), N(heterocycle)-CO—NH—$(C_1-C_6)$-alkyl, N (aryl)-CO—NH-aryl, N(heterocycle)-CO—NH-aryl, N(aryl)-CO—N—$[(C_1-C_6)$-alkyl$]_2$, N(heterocycle)-CO—N—$[(C_1-C_6)$-alkyl$]_2$, N(aryl)-CO—N$[(C_1-C_6)$-alkyl$]$-aryl, N(heterocycle)-CO—N$[(C_1-C_6)$-alkyl$]$-aryl, N(aryl)-CO—N-(aryl$)_2$, N(heterocycle)-CO—N-(aryl$)_2$, aryl, O—$(CH_2)_n$-aryl, O—$(CH_2)_n$-heterocycle, where n=0-6 and where the aryl radical or heterocyclic radical may be mono- to trisubstituted by F, Cl, Br, I, OH, $CF_3$, $NO_2$, CN, $OCF_3$, $O-(C_1-C_6)$-alkyl, $(C_1-C_6)$-alkyl, $NH_2$, $NH(C_1-C_6)$-alkyl, $N[(C_1-C_6)$-alkyl$]_2$, $SO_2-CH_3$, COOH, COO—$(C_1-C_6)$-alkyl or $CONH_2$.

A cycloalkyl radical is to be understood as meaning a ring system which comprises one or more rings and is saturated or partially unsaturated (with one or two double bonds) and is constructed exclusively of carbon atoms, such as, for example, cyclopropyl, cyclopentyl, cyclopentenyl, cyclohexyl or adamantyl.

The cycloalkyl radicals may be mono- or polysubstituted by suitable groups such as, for example: F, Cl, Br, I, $CF_3$, $NO_2$, $N_3$, CN, COOH, $COO(C_1-C_6)$-alkyl, $CONH_2$, $CONH(C_1-C_6)$-alkyl, $CON[(C_1-C_6)$-alkyl$]_2$, cycloalkyl, $(C_2-C_6)$-alkenyl, $(C_2-C_6)$-alkynyl, $O-(C_1-C_6)$-alkyl, $O-CO-(C_1-C_6)$-alkyl, $O-CO-(C_1-C_6)$-aryl, $O-CO-(C_1-C_6)$-heterocycle, $PO_3H_2$, $SO_3H$, $SO_2-NH_2$, $SO_2NH(C_1-C_6)$-alkyl, $SO_2N[(C_1-C_6)$-alkyl$]_2$, $S-(C_1-C_6)$-alkyl, $S-(CH_2)_n$-aryl, $S-(CH_2)_n$-heterocycle, $SO-(C_1-C_6)$-alkyl, SO—$(CH_2)_n$-aryl, SO—$(CH_2)_n$-heterocycle, $SO_2-(C_1-C_6)$-alkyl, $SO_2-(CH_2)_n$-aryl, $SO_2-(CH_2)_n$-heterocycle, $SO_2-NH(CH_2)_n$-aryl, $SO_2-NH(CH_2)_n$-heterocycle, $SO_2-N((C_1-C_6)$-alkyl$)(CH_2)_n$-aryl, $SO_2-N((C_1-C_6)$-alkyl$)(CH_2)_n$-heterocycle, $SO_2-N((CH_2)_n$-aryl$)_2$, $SO_2-N((CH_2)_n$-heterocycle$)_2$ where n=0-6 and where the aryl radical or the heterocyclic radical may be substituted up to two times by F, Cl, Br, OH, $CF_3$, $NO_2$, CN, $OCF_3$, $O-(C_1-C_6)$-alkyl, $(C_1-C_6)$-alkyl, $NH_2$;

$C(NH)(NH_2)$, $NH_2$, $NH-(C_1-C_6)$-alkyl, $N((C_1-C_6)$-alkyl$)_2$, $NH(C_2-C_7)$-acyl, $NH-CO-(C_1-C_6)$-alkyl, $NH-COO-(C_1-C_6)$-alkyl, NH—CO-aryl, NH—CO-heterocycle, NH—COO-aryl, NH—COO-heterocycle, $NH-CO-NH-(C_1-C_6)$-alkyl, NH—CO—NH-aryl, NH—CO—NH-heterocycle, $N[(C_1-C_6)$-alkyl$]$-$CO-(C_1-C_6)$-alkyl, $N[(C_1-C_6)$-alkyl$]$-$COO-(C_1-C_6)$-alkyl, $N[(C_1-C_6)$-alkyl$]$-CO-aryl, $N[(C_1-C_6)$-alkyl$]$-CO-heterocycle, $N(C_1-C_6)$-alkyl-COO-aryl, $N[(C_1-C_6)$-alkyl$]$-COO-heterocycle, $N[(C_1-C_6)$-alkyl$]$-$CO-NH-(C_1-C_6)$-alkyl), $N[(C_1-C_6)$-alkyl$]$-CO—NH-aryl, $N[(C_1-C_6)$-alkyl$]$-CO—NH-heterocycle, $N[(C_1-C_6)$-alkyl$]$-$CO-N-[(C_1-C_6)$-alkyl$]_2$, $N[(C_1-C_6)$-alkyl$]$-CO—N$[(C_1-C_6)$-alkyl$)]$-aryl, $N[(C_1-C_6)$-alkyl$]$-$CO-N[(C_1-C_6)$-alkyl$]$-heterocycle, $N[(C_1-C_6)$-alkyl$]$-CO—N-(aryl$)_2$. $N[(C_1-C_6)$-alkyl$]$-CO—N-(heterocycle$)_2$, N (aryl)-CO—$(C_1-C_6)$-alkyl, N (heterocycle)-CO—$(C_1-C_6)$-alkyl, N(aryl)-COO—$(C_1-C_6)$-alkyl, N(heterocycle)-COO—$(C_1-C_6)$-alkyl, N(aryl)-CO-aryl, N(heterocycle)-CO-aryl, N(aryl)-COO-aryl, N(heterocycle)-COO-aryl, N (aryl)-CO—NH—$(C_1-C_6)$-alkyl), N(heterocycle)-CO—NH—$(C_1-C_6)$-alkyl, N(aryl)-CO—NH-aryl, N(heterocycle)-CO—NH-aryl, N(aryl)-CO—N—[(C$_1$-C$_6$)-alkyl]$_2$, N(heterocycle)-CO—N—[(C$_1$-C$_6$)-alkyl]$_2$, N(aryl)-CO—N[(C$_1$-C$_6$)-alkyl]-aryl, N(heterocycle)-CO—N[(C$_1$-C$_6$)-alkyl]-aryl, N(aryl)-CO—N-(aryl)$_2$, N(heterocycle)-CO—N-(aryl)$_2$, aryl, O—(CH$_2$)$_n$-aryl, O—(CH$_2$)$_n$-heterocycle, where n=0-6 and where the aryl radical or the heterocyclic radical may be mono- to trisubstituted by F, Cl, Br, I, OH, CF$_3$, NO$_2$, CN, OCF$_3$, O—(C$_1$-C$_6$)-alkyl, (C$_1$-C$_6$)-alkyl, NH$_2$, NH(C$_1$-C$_6$)-alkyl, N[(C$_1$-C$_6$)-alkyl]$_2$, SO$_2$—CH$_3$, COOH, COO—(C$_1$-C$_6$)-alkyl or CONH$_2$.

A heterocycle or heterocyclic radical is to be understood as meaning rings and ring systems which, in addition to carbon, also contain heteroatoms, such as, for example, nitrogen, oxygen or sulfur. This definition furthermore includes ring systems in which the heterocyle or the heterocyclic radical is fused to a further ring system.

Suitable "heterocycles" or "heterocyclic radicals" are acridinyl, azocinyl, benzimidazolyl, benzofuryl, benzothienyl, benzothiophenyl, benzoxazolyl, benzothiazolyl, benzotriazolyl, benzotetrazolyl, benzisoxazolyl, benzisothiazolyl, benzimidazalinyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, 2H,6H-1,5,2-dithiazinyl, dihydrofuro[2,3-b]-tetrahydrofuran, 5,6-dihydro-4H-cyclopentathiazol-2-yl, 4,5-dihydrothiazol-2-yl, furyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, 4,5,6,7-tetrahydrobenzoxazol-2-yl, 4,5,6,7-tetrahydro-benzothiazol-2-yl, 4,5,6,7-tetrahydrobenzimidazol-2-yl, 4,5,6,7-tetrahydro-pyrazolo[1,5-a]pyridin-2-yl, tetrahydrofuranyl, tetrahydropyranyl, tetrahydroisoquinolinyl, tetrahydroquinolinyl, 6H-1,2,5-thiadazinyl, thiazolyl, 1,2,3-thiadiazolyl, 1,2,4-thiadiazolyl, 1,2,5-thiadiazolyl, 1,3,4-thiadiazolyl, thienyl, triazinyl, triazolyl, tetrazolyl, thiazolo[4,5-b]pyridinyl, thieno[2,3-d]thiazol-2-yl and xanthenyl.

Pyridyl denotes both 2-, 3- and 4-pyridyl. Thienyl denotes both 2- and 3-thienyl. Furyl denotes both 2- and 3-furyl.

Also included are the corresponding N-oxides of these compounds, i.e., for example, 1-oxy-2-, 3- or 4-pyridyl.

Furthermore included are mono- or polybenzo-fused derivatives of these heterocycles.

The heterocycles or heterocyclic radicals may be mono- or polysubstituted by suitable groups such as, for example: F, Cl, Br, I, CF$_3$, NO$_2$, N$_3$, CN, COOH, COO(C$_1$-C$_6$)-alkyl, CONH$_2$, CONH(C$_1$-C$_6$)-alkyl, CON[(C$_1$-C$_6$)-alkyl]$_2$, cycloalkyl, (C$_2$-C$_6$)-alkenyl, (C$_2$-C$_6$)-alkynyl, O—(C$_1$-C$_6$)-alkyl, O—CO—(C$_1$-C$_6$)-alkyl, O—CO—(C$_1$-C$_6$)-aryl, O—CO—(C$_1$-C$_6$)-heterocycle;

PO$_3$H$_2$, SO$_3$H, SO$_2$—NH$_2$, SO$_2$NH(C$_1$-C$_6$)-alkyl, SO$_2$N[(C$_1$-C$_6$)-alkyl]$_2$, S—(C$_1$-C$_6$)-alkyl, S—(CH$_2$)$_n$-aryl, S—(CH$_2$)$_n$-heterocycle, SO—(C$_1$-C$_6$)-alkyl, SO—(CH$_2$)$_n$-aryl, SO—(CH$_2$)$_n$-heterocycle, SO$_2$—(C$_1$-C$_6$)-alkyl, SO$_2$—(CH$_2$)$_n$-aryl, SO$_2$—(CH$_2$)$_n$-heterocycle, SO$_2$—NH(CH$_2$)$_n$-aryl, SO$_2$—NH(CH$_2$)$_n$-heterocycle, SO$_2$—N(C$_1$-C$_6$)-alkyl)(CH$_2$)$_n$-aryl, SO$_2$—N(C$_1$-C$_6$)-alkyl)(CH$_2$)$_n$-heterocycle, SO$_2$—N((CH$_2$)$_n$-aryl)$_2$, SO$_2$—N((CH$_2$)$_n$-(heterocycle)$_2$ where n=0-6 and where the aryl radical or the heterocyclic radical may be substituted up to two times by F, Cl, Br, OH, CF$_3$, NO$_2$, CN, OCF$_3$, O—(C$_1$-C$_6$)-alkyl, (C$_1$-C$_6$)-alkyl, NH$_2$;

C(NH)(NH$_2$), NH$_2$, NH—(C$_1$-C$_6$)-alkyl, N((C$_1$-C$_6$)-alkyl)$_2$, NH(C$_2$-C$_7$)-acyl, NH—CO—(C$_1$-C$_6$)-alkyl, NH—COO—(C$_1$-C$_6$)-alkyl, NH—CO-aryl, NH—CO-heterocycle, NH—COO-aryl, NH—COO-heterocycle, NH—CO—NH—(C$_1$-C$_6$)-alkyl, NH—CO—NH-aryl, NH—CO—NH-heterocycle, N[(C$_1$-C$_6$)-alkyl]-CO—(C$_1$-C$_6$)-alkyl, N[(C$_1$-C$_6$)-alkyl]-COO—(C$_1$-C$_6$)-alkyl, N[(C$_1$-C$_6$)-alkyl]-CO-aryl, N[(C$_1$-C$_6$)-alkyl]-CO-heterocycle, N(C$_1$-C$_6$)-alkyl-COO-aryl, N[(C$_1$-C$_6$)-alkyl]-COO-heterocycle, N[(C$_1$-C$_6$)-alkyl]-CO—NH—(C$_1$-C$_6$)-alkyl), N[(C$_1$-C$_6$)-alkyl]-CO—NH-aryl, N[(C$_1$-C$_6$)-alkyl]-CO—NH-heterocycle, N[(C$_1$-C$_6$)-alkyl]-CO—N—[(C$_1$-C$_6$)-alkyl]$_2$, N[(C$_1$-C$_6$)-alkyl]-CO—N[(C$_1$-C$_6$)-alkyl)]-aryl, N[(C$_1$-C$_6$)-alkyl]-CO—N[(C$_1$-C$_6$)-alkyl]-heterocycle, N[(C$_1$-C$_6$)-alkyl]-CO—N-(aryl)$_2$, N[(C$_1$-C$_6$)-alkyl]-CO—N-(heterocycle)$_2$, N(aryl)-CO—(C$_1$-C$_6$)-alkyl, N(heterocycle)-CO—(C$_1$-C$_6$)-alkyl, N(aryl)-COO—(C$_1$-C$_6$)-alkyl, N(heterocycle)-COO—(C$_1$-C$_6$)-alkyl, N(aryl)-CO-aryl, N(heterocycle)-CO-aryl, N(aryl)-COO-aryl, N(heterocycle)-COO-aryl, N(aryl)-CO—NH—(C$_1$-C$_6$)-alkyl), N(heterocycle)-CO—NH—(C$_1$-C$_6$)-alkyl, N(aryl)-CO—NH-aryl, N(heterocycle)-CO—NH-aryl, N(aryl)-CO—N—[(C$_1$-C$_6$)-alkyl]$_2$, N(heterocycle)-CO—N—[(C$_1$-C$_6$)-alkyl]$_2$, N(aryl)-CO—N[(C$_1$-C$_6$)-alkyl]-aryl, N(heterocycle)-CO—N[(C$_1$-C$_6$)-alkyl]-aryl, N(aryl)-CO—N-(aryl)$_2$, N(heterocycle)-CO—N-(aryl)$_2$, aryl, O—(CH$_2$)$_n$-aryl, O—(CH$_2$)$_n$-heterocycle, where n=0-6 and where the aryl radical or the heterocyclic radical may be mono- to trisubstituted by F, Cl, Br, I, OH, CF$_3$, NO$_2$, CN, OCF$_3$, O—(C$_1$-C$_6$)-alkyl, (C$_1$-C$_6$)-alkyl, NH$_2$, NH(C$_1$-C$_6$)-alkyl, N[(C$_1$-C$_6$)-alkyl]$_2$, SO$_2$—CH$_3$, COOH, COO—(C$_1$-C$_6$)-alkyl or CONH$_2$.

Compounds of the formula I activate glucose metabolism in glucokinase-expressing cells. They are therefore highly suitable for treating and preventing elevated blood glucose levels, obesity and metabolic syndrome (Sagen et al. Diabetes 55, 1713-1722, Levin et al. Diabetes (2006), S122-S130, Matschinsky et al (2006) 55, 1-12).

By virtue of the fact that they activate glucokinase, the compounds of the formula I may also be suitable for treating or preventing further diseases and conditions caused by elevated blood glucose levels, obesity or by reduced glucokinase activity in a mammal, preferably a human.

The compounds of the present invention are suitable in particular for the treatment and/or prevention of:

1.—Glucose utilization disorders and disorders of fatty acid metabolism
    disorders associated with insulin resistance Diabetes mellitus, in particular type-2 diabetes, including the prevention of sequelae associated therewith.

Particular aspects in this context are
    hyperglycemia,
    improving insulin resistance,
    improving glucose tolerance,
    protection of the β-cells of the pancreas
    prevention of macro- and microvascular disorders 2. Obesity and its sequelae such as, for example, dyslipidemias, atherosclerosis, coronary heart disease, cerebrovascular disorders etc., in particular (but not limited thereto) those with are characterized by one or more of the following factors:
high plasma triglyceride concentrations, high postprandial plasmatriglyceride concentrations,
low HDL cholesterol concentration
low ApoA lipoprotein concentrations
high LDL cholesterol concentrations
low density LDL cholesterol particles high ApoB lipoprotein concentrations 3. Various other conditions which may be associated with metabolic syndrome or syndrome X such as
increasing waist line
dyslipidemia (for example hypertriglyceridemia and/or low HDL)
insulin resistance
hypercoagulability
hyperurikemia
microalbuminemia
thromboses, hypercoagulable and prothrombotic conditions (arterial and venous)
hypertension
heart failure, for example (but not limited thereto) after myocardial infarction, hypertensive heart disease or cardiomyopathy 4. Primary hypertriglyceridemia or secondary hypertriglyceridemias after familiar reticulohistiocytosis lipoprotein-lipase deficiency hyperlipoproteinemias apolipoprotein deficiency (for example ApoCII or ApoE deficiency)

5. Genetically reduced activity of glucokinase, in particular MODY2

6. Diseases or conditions associated with neurological, psychiatric or immune disorders or conditions
The compound(s) of the formula (I) can also be administered in combination with further active ingredients.

The amount of a compound of formula I necessary to achieve the desired biological effect depends on a number of factors, for example the specific compound chosen, the intended use, the mode of administration and the clinical condition of the patient. The daily dose is generally in the range from 0.3 mg to 100 mg (typically from 3 mg to 50 mg) per day and per kilogram of body weight, for example 3-10 mg/kg/day. An intravenous dose may be for example in the range from 0.3 mg to 1.0 mg/kg, which can suitably be administered as infusion of from 10 ng to 100 ng per kilogram per minute. Suitable infusion solutions for these purposes may comprise for example from 0.1 ng to 10 mg, typically from 1 ng to 10 mg, per milliliter. Single doses may comprise for example from 1 mg to 10 g of the active ingredient. Thus, ampules for injections may comprise for example from 1 mg to 100 mg, and single-dose formulations which can be administered orally, such as, for example, tablets or capsules, may comprise for example from 1.0 to 1000 mg, typically from 10 to 600 mg. For the therapy of the abovementioned conditions, the compounds of formula I may be used as the compound itself, but are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including further compounds of formula I. The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be in the form of separate units such as, for example, capsules, cachets, suckable tablets or tablets, each of which contains a defined amount of the compound of formula I; as powders or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surface-active/dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise suckable tablets which contain a compound of formula I with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5% by weight of the active compound.

Pharmaceutical compositions suitable for rectal administration are preferably in the form of single-dose suppositories. These can be produced by mixing a compound of the formula I with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single patches which are suitable for long-term close contact with the patient's epidermis. Such patches suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described, for example, in Pharmaceutical Research, 2(6): 318 (1986).

Further active ingredients suitable for combination products are:

All antidiabetics which are mentioned in the Rote Liste 2006, chapter 12; all weight-reducing agents/appetite suppressants which are mentioned in the Rote Liste 2006, chapter 1; all lipid-lowering agents which are mentioned in the Rote Liste 2006, chapter 58. They may be combined with the compound of the invention of the formula I in particular for a synergistic improvement in the effect. The active ingredient combination can be administered either by separate administration of the active ingredients to the patient or in the form of combination products in which a plurality of active ingredients is present in a pharmaceutical preparation. Most of the active ingredients mentioned hereinafter are disclosed in the USP Dictionary of USAN and International Drug Names, US Pharmacopeia, Rockville 2001.

Antidiabetics include insulin and insulin derivatives such as, for example, Lantus® (see www.lantus.com) or HMR 1964 or Levemir® (insulin detemir) or those described in WO2005005477 (Novo Nordisk), fast-acting insulins (see U.S. Pat. No. 6,221,633), inhalable insulins such as, for example, Exubera® or oral insulins such as, for example, IN-105 (Nobex) or Oral-Lyn™ (Generex Biotechnology), GLP-1 derivatives such as, for example, exenatide, liraglutide or those which have been disclosed in WO98/08871, WO2005027978, WO2006037811, WO2006037810 of Novo Nordisk A/S, in WO01/04156 of Zealand or in WO00/34331 of Beaufour-Ipsen, pramlintide acetate (Symlin; Amylin Pharmaceuticals), and orally effective hypoglycemic active ingredients.

The orally effective hypoglycemic active ingredients include preferably sulfonylureas, biguanidines, meglitinides, oxadiazolidinediones, thiazolidinediones, glucosidase inhibitors, inhibitors of glycogen phosphorylase, glucagon antagonists, glucokinase activators, inhibitors of fructose-1,6-bisphosphatase, modulators of glucose transporter 4 (GLUT4), inhibitors of glutamine-fructose-6-phosphate amidotransferase (GFAT), GLP-1 agonists, potassium channel openers such as, for example those which have been disclosed in WO 97/26265 and WO 99/03861 of Novo Nordisk A/S or those described in WO2006045799 (Solvay), inhibitors of dipeptidylpeptidase IV (DPP-IV), insulin sensitizers, inhibitors of liver enzymes involved in stimulating gluconeogenesis and/or glycogenolysis, modulators of glucose uptake, of glucose transport and of glucose reabsorption, inhibitors of 11β-HSD 1, inhibitors of protein tyrosine phosphatase 1B (PTP1B), modulators of the sodium-dependent glucose transporter 1 or 2 (SGLT1, SGLT2), compounds which alter lipid metabolism such as antihyperlipidemic active ingredients and antilipidemic active ingredients, compounds which reduce food intake, compounds which increase thermogenesis, PPAR and RXR modulators and active ingredients which act on the ATP-dependent potassium channel of the beta cells.

In one embodiment of the invention, the compound of the formula I is administered in combination with an HMGCoA reductase inhibitor such as simvastatin, fluvastatin, pravastatin, lovastatin, atorvastatin, cerivastatin, rosuvastatin, L-659699.

In one embodiment of the invention, the compound of the formula I is administered in combination with a cholesterol absorption inhibitor such as, for example, ezetimibe, tiqueside, pamaqueside, FM-VP4 (sitostanol/campesterol ascorbyl phosphate; Forbes Medi-Tech, WO2005042692, WO2005005453), MD-0727 (Microbia Inc., WO2005021497, WO2005021495) or with compounds as described in WO2002066464 (Kotobuki Pharmaceutical Co. Ltd.) or WO2005044256 or WO2005062824 (Merck & Co.) or WO2005061451 and WO2005061452 (AstraZeneca AB) and WO2006017257 (Phenomix) or WO2005033100 (Lipideon Biotechnology AG).

In one embodiment of the invention, the compound of the formula I is administered in combination with Vytorin™, a fixed combination of ezetimibe with simvastatin.

In one embodiment of the invention, the compound of the formula I is administered in combination with a fixed combination of ezetimibe with fenofibrate.

In a further embodiment of the invention, the compound of the formula I is administered in combination with a fixed combination of fenofibrate with rosuvastatin.

In one embodiment of the invention, the compound of the formula I is administered in combination with ISIS-301012, an antisense oligonucleotide able to regulate the apolipoprotein B gene.

In one embodiment of the invention, the compound of the formula I is administered in combination with a PPAR gamma agonist such as, for example, rosiglitazone, pioglitazone, JTT-501, GI 262570, R483 or CS-011 (rivoglitazone).

In one embodiment of the invention, the compound of the formula I is administered in combination with Competact™, a fixed combination of pioglitazone hydrochloride with metformin hydrochloride.

In one embodiment of the invention, the compound of the formula I is administered in combination with Duetact™, a fixed combination of pioglitazone hydrochloride with glimepiride.

In one embodiment of the invention, the compound of the formula I is administered in combination with Avandamet®, a fixed combination of rosiglitazone maleate with metformin hydrochloride.

In one embodiment of the invention, the compound of the formula I is administered in combination with a PPAR alpha agonist such as, for example, GW9578, GW-590735, K-111, LY-674, KRP-101, DRF-10945.

In one embodiment of the invention, the compound of the formula I is administered in combination with a mixed PPAR alpha/gamma agonist such as, for example, naveglitazar, LY-510929, ONO-5129, E-3030, AVE 8042, AVE 8134, AVE 0847, or as in PCT/US00/11833, PCT/US00/11490, DE10142734.4 or as described in J. P. Berger et al., TRENDS in Pharmacological Sciences 28(5), 244-251, 2005.

In one embodiment, the compound of the formula I is administered in combination with a PPAR delta agonist such as, for example, GW-501516.

In one embodiment, the compound of the formula I is administered in combination with metaglidasen or with MBX-2044 or other partial PPAR gamma agonists/antagonists.

In a further embodiment of the invention, the compound of the formula I is administered in combination with an activator of AMP-activated protein kinase (AMPK), such as, for example, A-769662 or those compounds as described in US20050038068.

In one embodiment of the invention, the compound of the formula I is administered in combination with a fibrate such as, for example, fenofibrate, clofibrate, bezafibrate.

In one embodiment of the invention, the compound of the formula I is administered in combination with an MTP inhibitor such as, for example, implitapide, BMS-201038, R-103757 or those as described in WO2005085226, WO2005121091, WO2006010423.

In one embodiment of the invention, the compound of the formula I is administered in combination with a CETP inhibitor such as, for example, torcetrapib or JTT-705 or those as described in WO2006002342, WO2006010422, WO2006012093.

In one embodiment of the invention, the compound of the formula I is administered in combination with a bile acid absorption inhibitor (see, for example, U.S. Pat. No. 6,245, 744, U.S. Pat. No. 6,221,897 or WO00/61568) such as, for example, HMR 1741 or those as described in DE 10 2005 033099.1 and DE 10 2005 033100.9.

In one embodiment, the compound of the formula I is administered in combination with a polymeric bile acid adsorbent such as, for example, cholestyramine or colesevelam.

In one embodiment of the invention, the compound of the formula I is administered in combination with an LDL receptor inducer (see U.S. Pat. No. 6,342,512), such as, for example, HMR1171, HMR1586 or those as described in WO2005097738.

In one embodiment, the compound of the formula I is administered in combination with Omacor<D (omega-3 fatty acids; highly concentrated ethyl esters of eicosapentaenoic acid and of docosahexaenoic acid).

In one embodiment of the invention, the compound of the formula I is administered in combination with an ACAT inhibitor such as, for example, avasimibe or SMP-797.

In one embodiment of the invention, the compound of the formula I is administered in combination with an antioxidant such as, for example, OPC-14117, probucol, tocopherol, ascorbic acid, β-carotene or selenium.

In one embodiment of the invention, the compound of the formula I is administered in combination with a vitamin such as, for example, vitamin B6 or vitamin B12.

In one embodiment of the invention, the compound of the formula I is administered in combination with a lipoprotein lipase modulator such as, for example, ibrolipim (NO-1886).

In one embodiment of the invention, the compound of the formula I is administered in combination with an ATP citrate lyase inhibitor such as, for example, SB-204990.

In one embodiment of the invention, the compound of the formula I is administered in combination with a squalene synthetase inhibitor such as, for example, BMS-188494 or as described in WO2005077907.

In one embodiment of the invention, the compound of the formula I is administered in combination with a lipoprotein (a) antagonist such as, for example, gemcabene (Cl-1027).

In one embodiment of the invention, the compound of the formula I is administered in combination with an agonist of GPR109A (HM74A receptor agonist) such as, for example, nicotinic acid or extended release niacin in conjunction with MK-0524A or the compounds described in WO2006045565, WO2006045564, WO2006069242.

In another embodiment of the invention, the compound of the formula I is administered in combination with an agonist of GPR116 as described for example in WO2006067531, WO2006067532.

In one embodiment of the invention, the compound of the formula I is administered in combination with a lipase inhibitor such as, for example, orlistat or cetilistat (ATL-962).

In one embodiment of the invention, the compound of the formula I is administered in combination with insulin.

In one embodiment, the compound of the formula I is administered in combination with a sulfonylurea such as, for example, tolbutamide, glibenclamide, glipizide or glimepiride.

In one embodiment, the compound of the formula I is administered in combination with a substance which enhances insulin secretion, such as, for example, KCP-265 (WO2003097064).

In one embodiment, the compound of the formula I is administered in combination with agonists of the glucose-dependent insulinotropic receptor (GDIR), such as, for example, APD-668.

In one embodiment, the compound of the formula I is administered in combination with a biguanide such as, for example, metformin.

In another embodiment, the compound of the formula I is administered in combination with a meglitinide such as, for example, repaglinide or nateglinide.

In one embodiment, the compound of the formula I is administered in combination with a thiazolidinedione such as, for example, troglitazone, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinyl)methoxy]phenyl] methyl]-2,4-thiazolidinedione.

In one embodiment, the compound of the formula I is administered in combination with an α-glucosidase inhibitor such as, for example, miglitol or acarbose.

In one embodiment, the compound of the formula I is administered in combination with an active ingredient which acts on the ATP-dependent potassium channel of the beta cells, such as, for example, tolbutamide, glibenclamide, glipizide, glimepiride or repaglinide.

In one embodiment, the compound of the formula I is administered in combination with more than one of the aforementioned compounds, for example in combination with a sulfonylurea and metformin, a sulfonylurea and acarbose, repaglinide and metformin, insulin and a sulfonylurea, insulin and metformin, insulin and troglitazone, insulin and lovastatin, etc.

In one embodiment, the compound of the formula I is administered in combination with an inhibitor of glycogen phosphorylase, such as, for example, PSN-357 or FR-258900 or those as described in WO2003084922, WO2004007455, WO2005073229-31, WO2005067932.

In one embodiment, the compound of the formula I is administered in combination with glucagon receptor antagonists such as, for example, A-770077, NNC-25-2504 or as described in WO2004100875 or WO2005065680.

In one embodiment, the compound of the formula I is administered in combination with activators of glucokinase, such as, for example, LY-2121260 (WO2004063179), PSN-105, PSN-110, GKA-50 or those as are described, for example, in WO2004072031, WO2004072066, WO2005080360, WO2005044801, WO2006016194, WO2006058923.

In one embodiment, the compound of the formula I is administered in combination with an inhibitor of gluconeogenesis, such as, for example, FR-225654.

In one embodiment, the compound of the formula I is administered in combination with inhibitors of fructose-1,6-bisphosphatase (FBPase), such as, for example, CS-917 (MB-06322) or MB-07803 or those described in WO2006023515.

In one embodiment, the compound of the formula I is administered in combination with modulators of glucose transporter 4 (GLUT4), such as, for example, KST-48 (D.-O. Lee et al.: Arzneim.-Forsch. Drug Res. 54 (12), 835 (2004)).

In one embodiment, the compound of the formula I is administered in combination with inhibitors of glutamine-fructose-6-phosphate amidotransferase (GFAT), as are described for example in WO2004101528.

In one embodiment of the invention, the compound of the formula I is administered in combination with inhibitors of dipeptidylpeptidase IV (DPP-IV), such as, for example, vildagliptin (LAF-237), sitagliptin (MK-0431), saxagliptin ((BMS477118), GSK-823093, PSN-9301, SYR-322, SYR-619, TA-6666, TS-021, GRC-8200, GW-825964X, KRP-104, DP-893 or as described in WO2003074500, WO2003106456, WO200450658, WO2005058901, WO2005012312, WO2005/012308, WO2006039325, WO2006058064, PCT/EP2005/007821, PCT/EP2005/008005, PCT/EP2005/008002, PCT/EP2005/008004, PCT/EP2005/008283, DE 10 2005 012874.2 or DE 10 2005 012873.4.

In one embodiment, the compound of the formula I is administered in combination with Januvia™, a fixed combination of sitagliptin phosphate with metformin hydrochloride.

In one embodiment, the compound of the formula I is administered in combination with inhibitors of 1'-beta-hydroxysteroid dehydrogenase 1 (11β-HSD1), such as, for example, BVT-2733, JNJ-25918646, INCB-13739 or those as are described, for example, in WO200190090-94, WO200343999, WO2004112782, WO200344000, WO200344009, WO2004112779, WO2004113310, WO2004103980, WO2004112784, WO2003065983, WO2003104207, WO2003104208, WO2004106294, WO2004011410, WO2004033427, WO2004041264, WO2004037251, WO2004056744, WO2004058730, WO2004065351, WO2004089367, WO2004089380, WO2004089470-71, WO2004089896, WO2005016877, WO2005097759, WO2006010546, WO2006012227, WO2006012173, WO2006017542, WO2006034804, WO2006040329, WO2006051662, WO2006048750, WO2006049952, WO2006048331, WO2006050908, WO2006024627, WO2006040329, WO2006066109.

In one embodiment, the compound of the formula I is administered in combination with inhibitors of protein tyrosine phosphatase 1B (PTP1B), as are described for example in WO200119830-31, WO200117516, WO2004506446, WO2005012295, WO2005116003, PCT/EP2005/005311, PCT/EP2005/005321, PCT/EP2005/007151, PCT/EP2005/01294 or DE 10 2004 060542.4.

In one embodiment, the compound of the formula I is administered in combination with modulators of the sodium-dependent glucose transporter 1 or 2 (SGLT1, SGLT2) such as, for example, KGA-2727, T-1095, SGL-0010, AVE 2268 and SAR 7226 or as described, for example, in WO2004007517, WO200452903, WO200452902, PCT/EP2005/005959, WO2005085237, JP2004359630, WO2005121161, WO2006018150, WO2006035796, WO2006062224, WO2006058597 or by A. L. Handlon in Expert Opin. Ther. Patents (2005) 15(11), 1531-1540.

In one embodiment, the compound of the formula I is administered in combination with modulators of GPR40.

In one embodiment, the compound of the formula I is administered in combination with modulators of GPR119b as described, for example, in WO2004041274.

In one embodiment, the compound of the formula I is administered in combination with modulators of GPR119 as described, for example, in WO2005061489 (PSN-632408).

In one embodiment, the compound of the formula I is administered in combination with inhibitors of hormone-sensitive lipase (HSL) as described, for example, in WO2005073199.

In one embodiment, the compound of the formula I is administered in combination with inhibitors of acetyl-CoA carboxylase (ACC), such as, for example, those as described in WO199946262, WO200372197, WO2003072197, WO2005044814, WO2005108370, JP2006131559.

In one embodiment, the compound of the formula I is administered in combination with an inhibitor of phosphoenolpyruvate carboxykinase (PEPCK), such as, for example, those as described in WO2004074288.

In one embodiment, the compound of the formula I is administered in combination with an inhibitor of glycogen synthase kinase 3 beta (GSK-3 beta), as described, for example, in US2005222220, WO2005085230, PCT/EP2005/005346, WO2003078403, WO2004022544, WO2003106410, WO2005058908, US2005038023, WO2005009997, US2005026984, WO2005000836, WO2004106343, EP1460075, WO2004014910, WO2003076442, WO2005087727, WO2004046117.

In one embodiment, the compound of the formula I is administered in combination with an inhibitor of protein kinase C beta (PKC beta), such as, for example, ruboxistaurin.

In one embodiment, the compound of the formula I is administered in combination with an endothelin A receptor antagonist such as, for example, avosentan (SPP-301).

In one embodiment, the compound of the formula I is administered in combination with inhibitors of "I-kappaB kinase" (IKK inhibitors), as are described for example in WO2001000610, WO2001030774, WO2004022553 or WO2005097129.

In one embodiment, the compound of the formula I is administered in combination with modulators of the glucocorticoid receptor like those described, for example, in WO2005090336.

In a further embodiment, the compound of the formula I is administered in combination with CART modulators (see "Cocaine-amphetamine-regulated transcript influences energy metabolism, anxiety and gastric emptying in mice" Asakawa, A. et al.: Hormone and Metabolic Research (2001), 33(9), 554-558);

NPY antagonists such as, for example, naphthalene-1-sulfonic acid {4-[(4-aminoquinazolin-2-ylamino)methyl] cyclohexylmethyl}amide hydrochloride (CGP 71683A);

NPY-5 receptor antagonists such as L-152804 or S-2367 or as are described, for example in WO2006001318;

peptide YY 3-36 (PYY3-36) or analogous compounds, such as, for example, CJC-1682 (PYY3-36 conjugated with human serum albumin via Cys34), CJC-1643 (derivative of PYY3-36 which conjugates in vivo to serum albumin) or those as are described in WO2005080424;

CB1R (cannabinoid receptor 1) antagonists (such as, for example, rimonabant, SR147778 or those as described, for example, in EP 0656354, WO 00/15609, WO 02/076949, WO2005080345, WO2005080328, WO2005080343, WO2005075450, WO2005080357, WO200170700, WO2003026647-48, WO200302776, WO2003040107, WO2003007887, WO2003027069, U.S. Pat. No. 6,509,367, WO200132663, WO2003086288, WO2003087037, WO2004048317, WO2004058145, WO2003084930, WO2003084943, WO2004058744, WO2004013120, WO2004029204, WO2004035566, WO2004058249, WO2004058255, WO2004058727, WO2004069838, US20040214837, US20040214855, US20040214856, WO2004096209, WO2004096763, WO2004096794, WO2005000809, WO2004099157, US20040266845, WO2004110453, WO2004108728, WO2004000817, WO2005000820, US20050009870, WO200500974, WO2004111033-34, WO200411038-39, WO2005016286, WO2005007111, WO2005007628, US20050054679, WO2005027837, WO2005028456, WO2005063761-62, WO2005061509, WO2005077897, WO2006047516, WO2006060461, WO2006067428, WO2006067443); MC4 agonists (for example 1-amino-1,2,3,4-tetrahydronaphthalene-2-carboxylic acid [2-(3a-benzyl-2-methyl-3-oxo-2,3, 3a,4,6,7-hexahydropyrazolo[4,3-c]pyridin-5-yl)-1-(4-chlorophenyl)-2-oxoethyl]amide; (WO 01/91752)) or LB53280, LB53279, LB53278 or THIQ, MB243, RY764, CHIR-785, PT-141 or those that are described in WO2005060985, WO2005009950, WO2004087159, WO2004078717, WO2004078716, WO2004024720, US20050124652, WO2005051391, WO2004112793, WOUS20050222014, US20050176728, US20050164914, US20050124636, US20050130988, US20040167201, WO2004005324, WO2004037797, WO2005042516, WO2005040109, WO2005030797, US20040224901, WO200501921, WO200509184, WO2005000339, EP1460069, WO2005047253, WO2005047251, EP1538159, WO2004072076, WO2004072077, WO2006021655-57;

orexin receptor antagonists (for example 1-(2-methylbenzoxazol-6-yl)-3-[1,5]naphthyridin-4-ylurea hydrochloride (SB-334867-A) or those as are described for example in WO200196302, WO200185693, WO2004085403, WO2005075458, WO2006/67224);

histamine H3 receptor agonists (for example 3-cyclohexyl-1-(4,4-dimethyl-1,4,6,7-tetrahydroimidazo[4,5-c]pyridin-5-yl)propan-1-one oxalic acid salt (WO 00/63208) or those as are described in WO200064884, WO2005082893); CRF antagonists (for example [2-methyl-9-(2,4,6-trimethylphenyl)-9H-1,3,9-triazafluoren-4-yl]dipropylamine (WO 00/66585)); CRF BP antagonists (for example urocortin); urocortin agonists;

agonists of the beta-3 adrenoreceptor such as, for example, 1-(4-chloro-3-methanesulfonyl methylphenyl)-2-[2-(2,3-dimethyl-1H-indol-6-yloxy)ethylamino]ethanol hydrochloride (WO 01/83451) or solabegron (GW-427353) or N-5984 (KRP-204), or those as are described in JP2006111553;

MSH (melanocyte-stimulating hormone) agonists;

MCH (melanin-concentrating hormone) receptor antagonists (such as, for example, NBI-845, A-761, A-665798, A-798, ATC-0175, T-226296, T-71, GW-803430 or compounds such as are described in WO2003/15769, WO2005085200, WO2005019240, WO2004011438, WO2004012648, WO2003015769, WO2004072025, WO2005070898, WO2005070925, WO2004039780, WO2003033476, WO2002006245, WO2002089729, WO2002002744, WO2003004027, FR2868780, WO2006010446, WO2006038680, WO2006044293, WO2006044174);

CCK-A agonists (such as, for example, {2-[4-(4-chloro-2,5-dimethoxyphenyl)-5-(2-cyclohexylethyl)thiazol-2-ylcarbamoyl]-5,7-dimethyl indol-1-yl}acetic acid trifluoroacetic acid salt (WO 99/15525) or SR-146131 (WO 0244150) or SSR-125180) or those as are described in WO2005116034; serotonin reuptake inhibitors (e.g. dexfenfluramine);

mixed serotoninergic and noradrenergic compounds (for example WO 00/71549);

5-HT receptor agonists, for example 1-(3-ethylbenzofuran-7-yl)piperazine oxalic acid salt (WO 01/09111);

5-HT2C receptor agonists (such as, for example, lorcaserin hydrochloride (APD-356) or BVT-933 or those as are described in WO200077010, WO20077001-02, WO2005019180, WO2003064423, WO200242304, WO2005082859);

5-HT6 receptor antagonists as described, for example, in WO2005058858;

bombesin receptor agonists (BRS-3 agonists);

galanin receptor antagonists;

growth hormone (e.g. human growth hormone or AOD-9604);

growth hormone-releasing compounds (tertiary butyl 6-benzyloxy-1-(2-diisopropyl-aminoethylcarbamoyl)-3,4-dihydro-1H-isoquinoline-2-carboxylate (WO 01/85695));

growth hormone secretagogue receptor antagonists (ghrelin antagonists) such as, for example, A-778193 or those as are described in WO2005030734;

TRH agonists (see, for example, EP 0 462 884);

uncoupling protein 2 or 3 modulators;

leptin agonists (see, for example, Lee, Daniel W.; Leinung, Matthew C.;

Rozhavskaya-Arena, Marina; Grasso, Patricia. Leptin agonists as a potential approach to the treatment of obesity. Drugs of the Future (2001), 2.6 (9), 873-881);

DA agonists (bromocriptine or Doprexin); lipase/amylase inhibitors (for example WO 00/40569);

inhibitors of diacylglycerol O-acyltransferases (DGATS) such as for example BAY-74-4113 or as described for example in US2004/0224997, WO2004094618, WO200058491, WO2005044250, WO2005072740, JP2005206492, WO2005013907, WO2006004200, WO2006019020, WO2006064189;

inhibitors of fatty acid synthase (FAS) such as, for example, C75 or those as described in WO2004005277;

oxyntomodulin;

oleoyl-estrone or thyroid hormone receptor agonists such as, for example: KB-2115 or those as described in WO20058279, WO200172692, WO200194293, WO2003084915, WO2004018421, WO2005092316.

In one embodiment, the further active ingredient is varenicline tartrate, a partial agonist of the alpha 4-beta 2 nicotinic acetylcholine receptor.

In one embodiment, the further active ingredient is trodusquemine.

In one embodiment, the further active ingredient is a modulator of the SIRT1 enzyme, a member of the human sirtuin enzyme family.

In one embodiment of the invention, the further active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In one embodiment, the further active ingredient is dexamphetamine or amphetamine.

In one embodiment, the further active ingredient is fenfluramine or dexfenfluramine.

In another embodiment, the further active ingredient is sibutramine.

In one embodiment, the further active ingredient is mazindole or phentermine.

In one embodiment, the compound of the formula I is administered in combination with bulking agents, preferably insoluble bulking agents (see, for example, Carob/Caromax® (Zunft H J; et al., Carob pulp preparation for treatment of hypercholesterolemia, ADVANCES IN THERAPY (2001 September-October), 18(5), 230-6. Caromax is a carob-containing product from Nutrinova, Nutrition Specialties & Food Ingredients GmbH, Industriepark Höchst, 65926 Frankfurt/Main). Combination with Caromax® is possible in one preparation or by separate administration of compounds of the formula I and Caromax®. Caromax® can in this connection also be administered in the form of food products such as, for example, in bakery products or muesli bars.

It will be understood that every suitable combination of the compounds of the invention with one or more of the aforementioned compounds and optionally one or more further pharmacologically active substances will be regarded as falling within the protection conferred by the present invention.

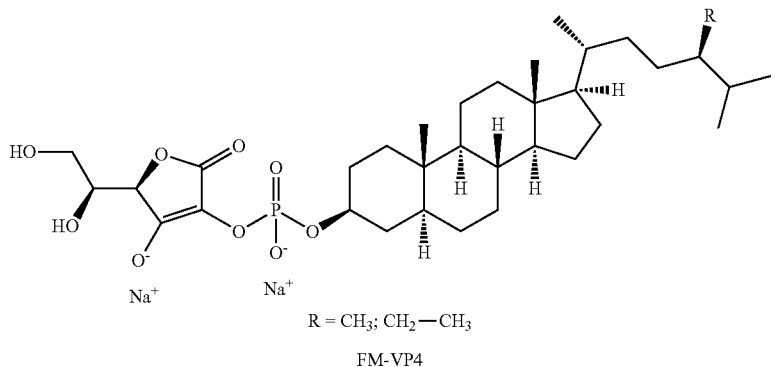

FM-VP4

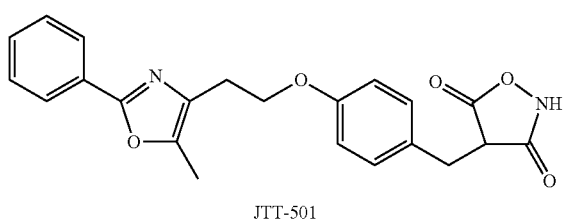

JTT-501

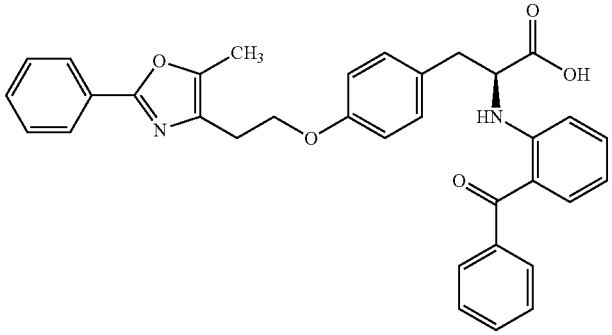

GI 262570

-continued
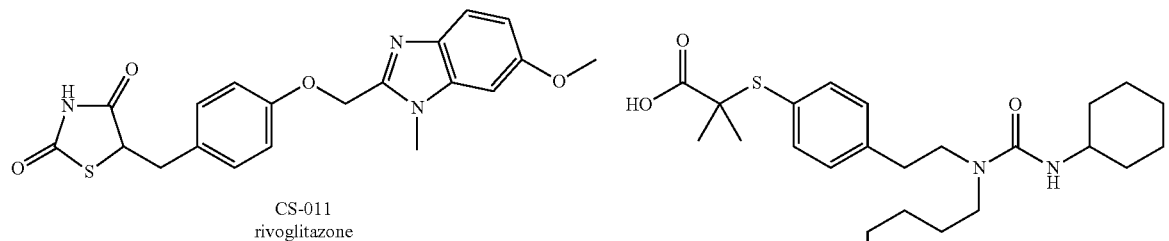
CS-011
rivoglitazone
GW-9578
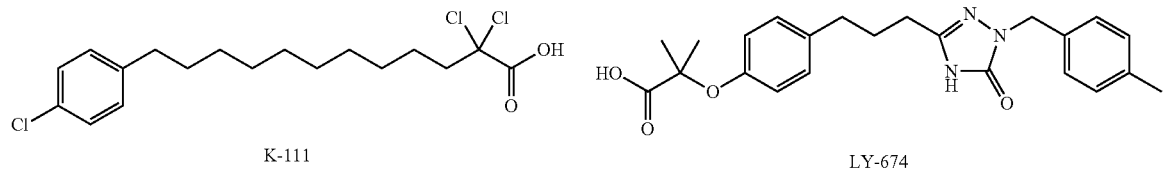
K-111
LY-674
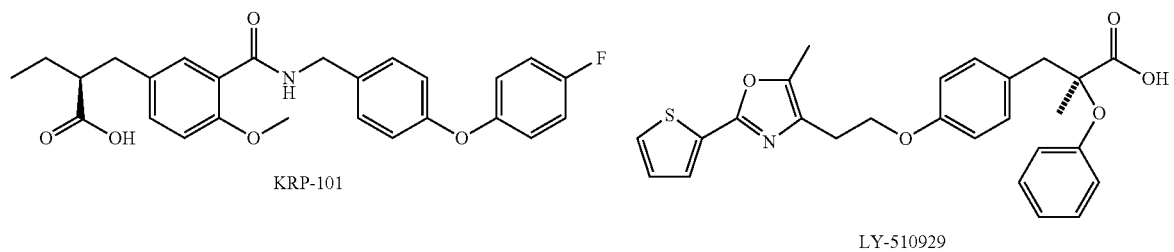
KRP-101
LY-510929
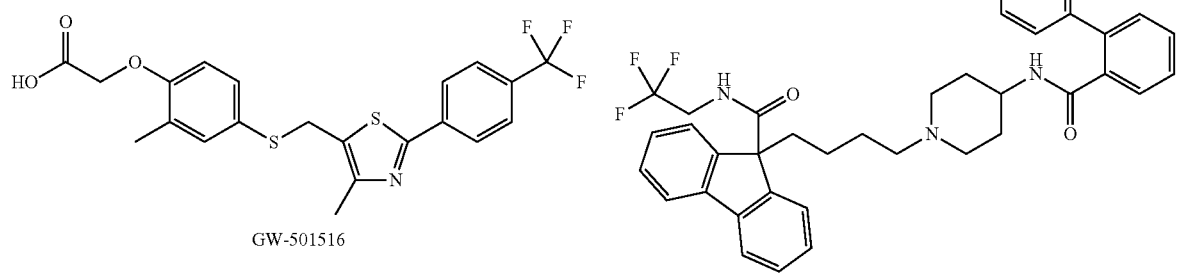
GW-501516
BMS-201038

-continued
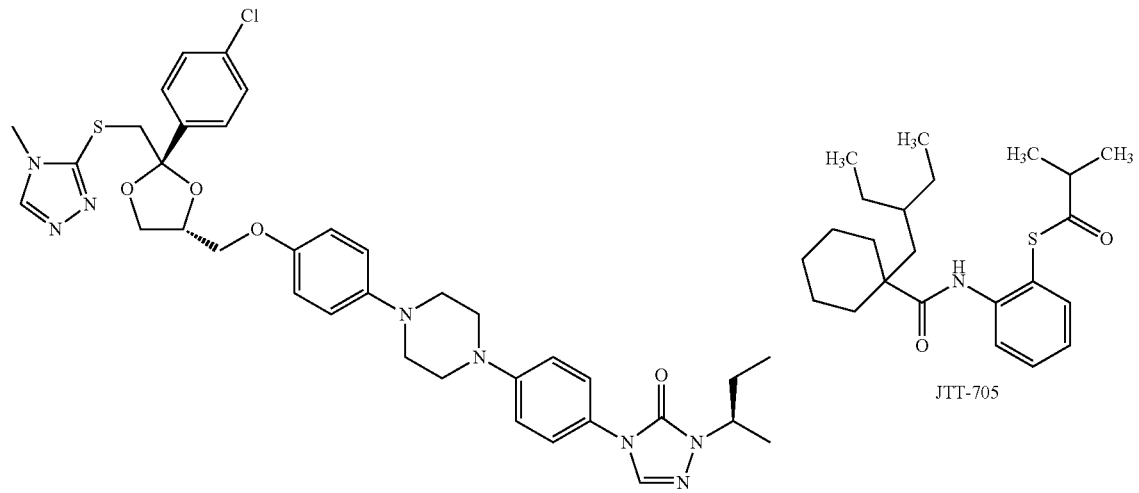
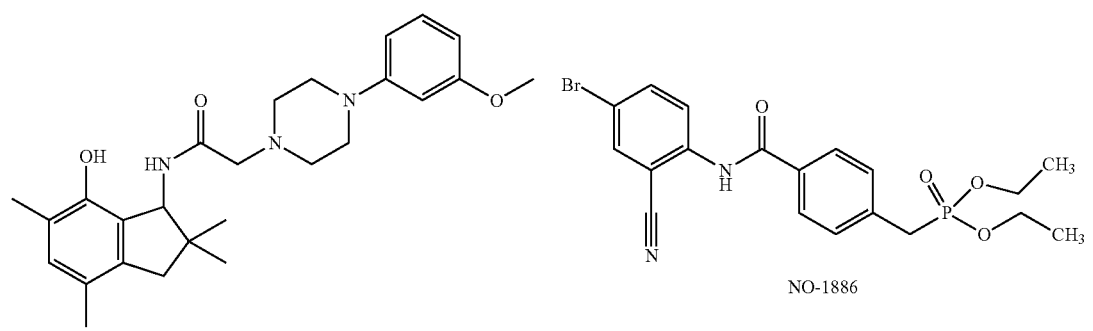
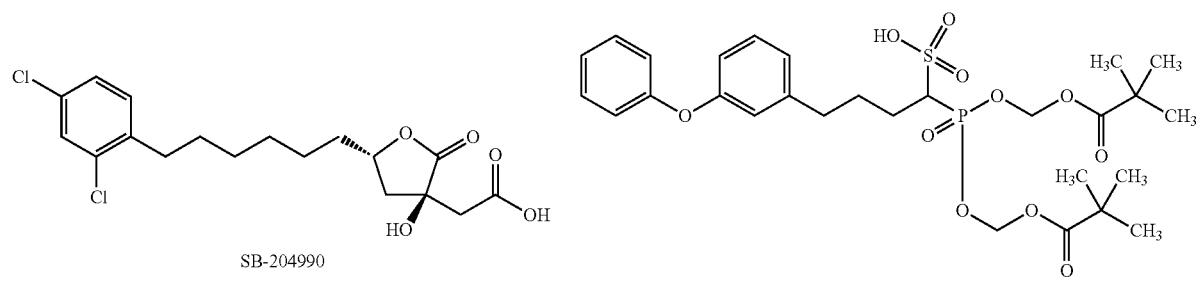
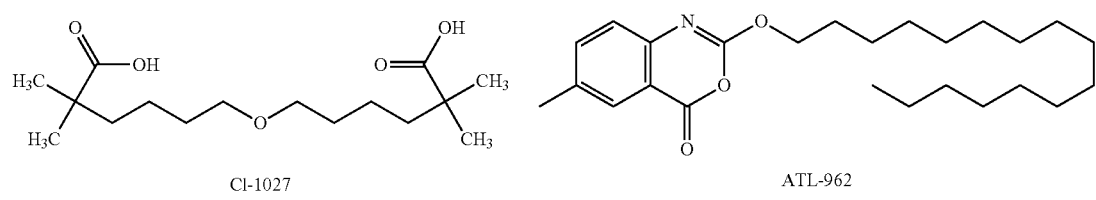

-continued
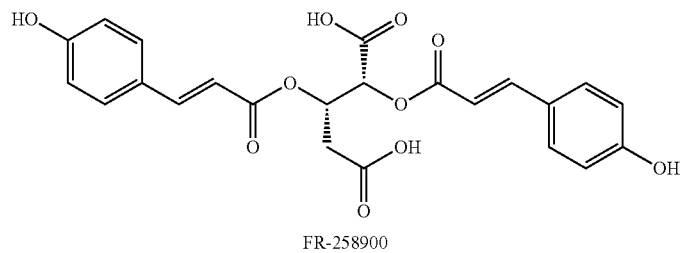
FR-258900
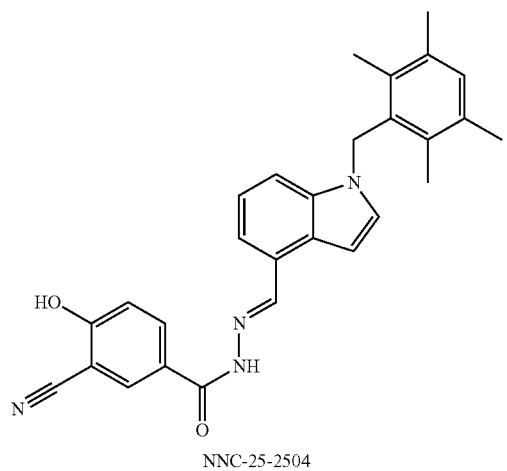
NNC-25-2504
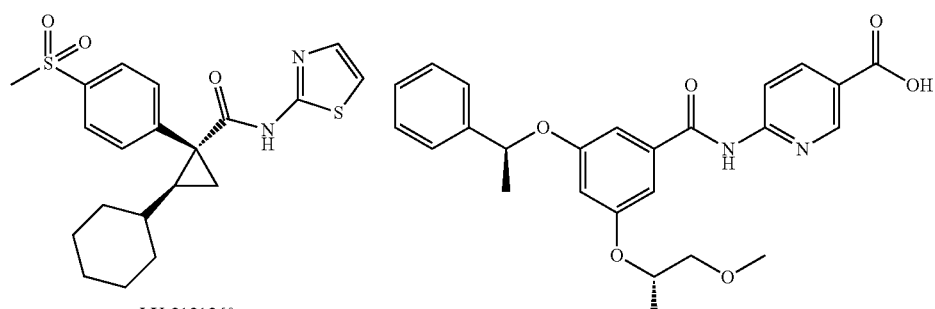
LY-2121260
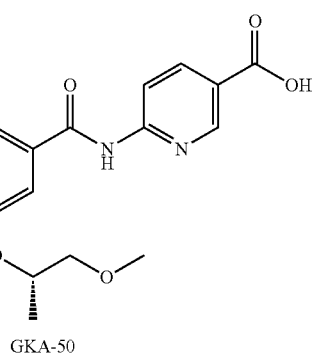
GKA-50
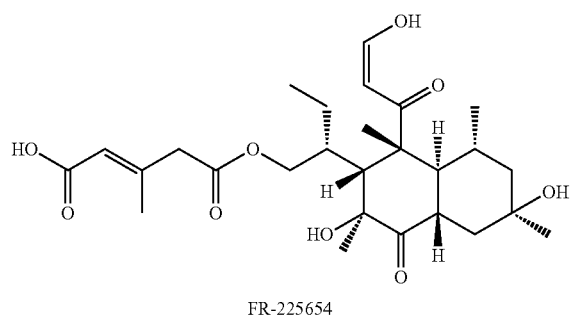
FR-225654
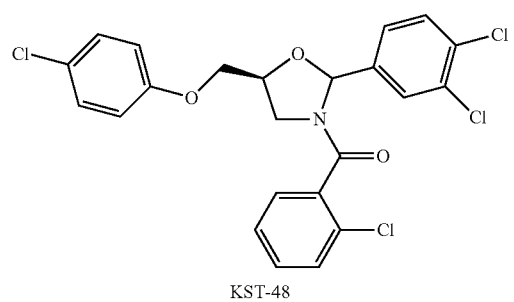
KST-48
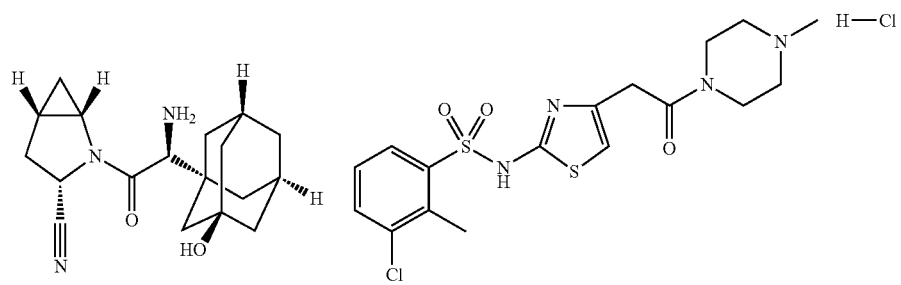
BMS-477118
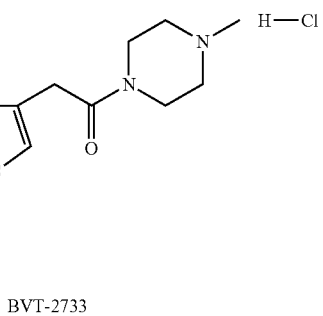
BVT-2733

-continued
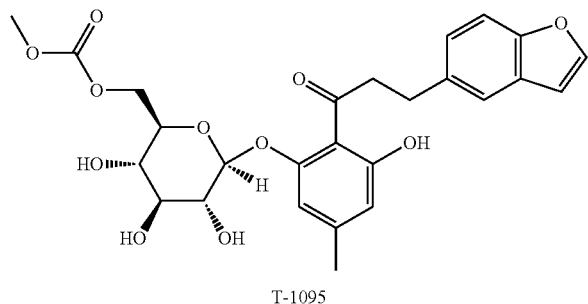
T-1095
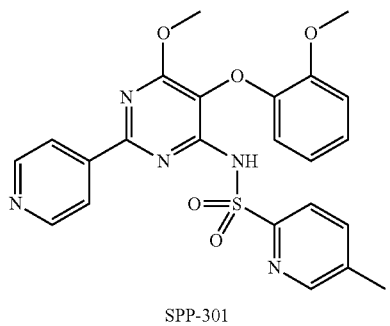
SPP-301
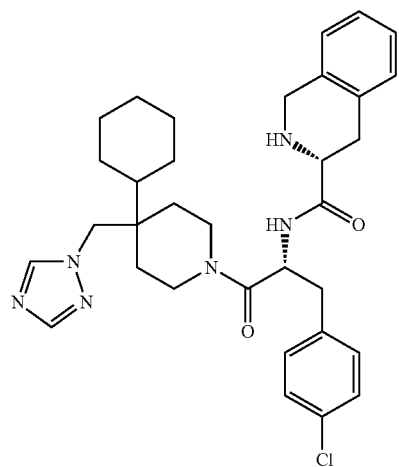
THIQ
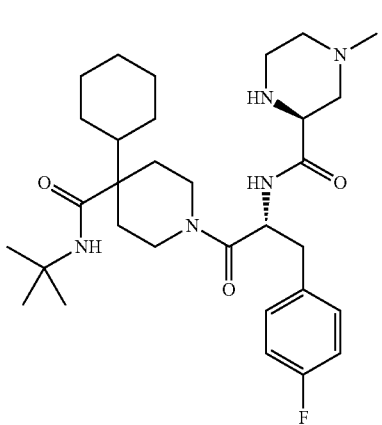
MB243
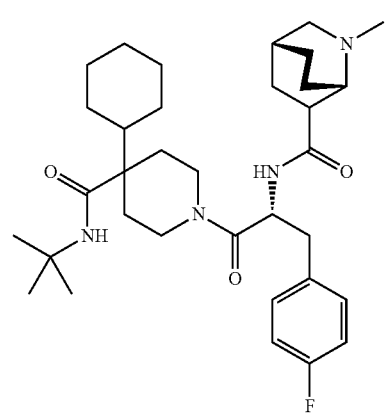
RY764
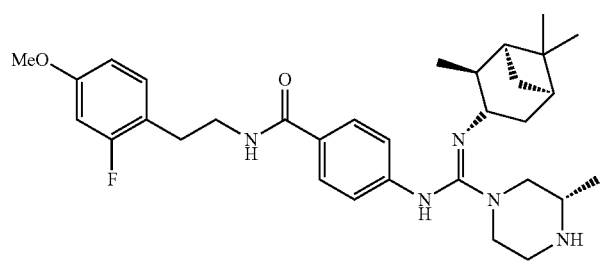
CHIR-785
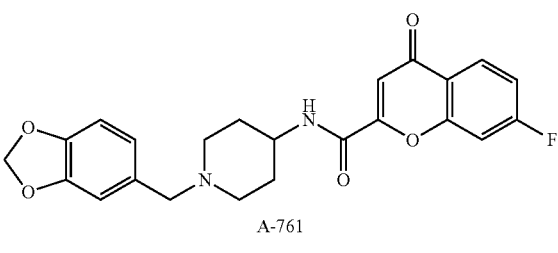
A-761
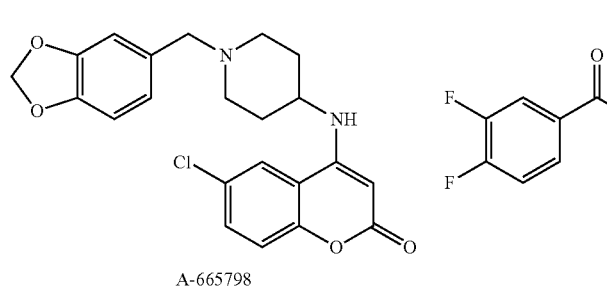
A-665798
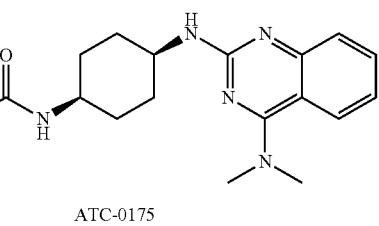
ATC-0175
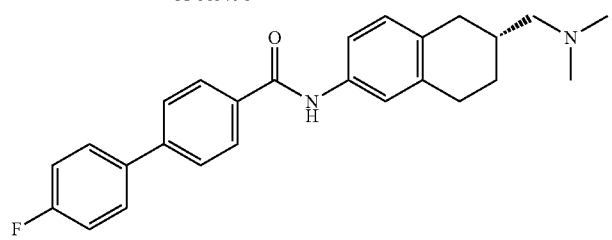
T-226296

-continued
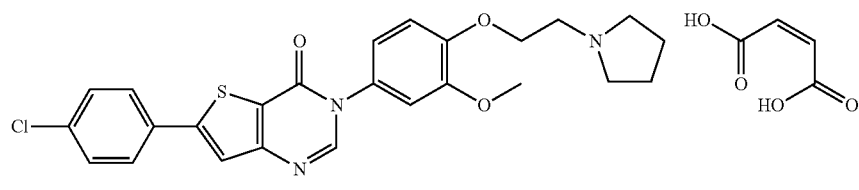
GW-803430
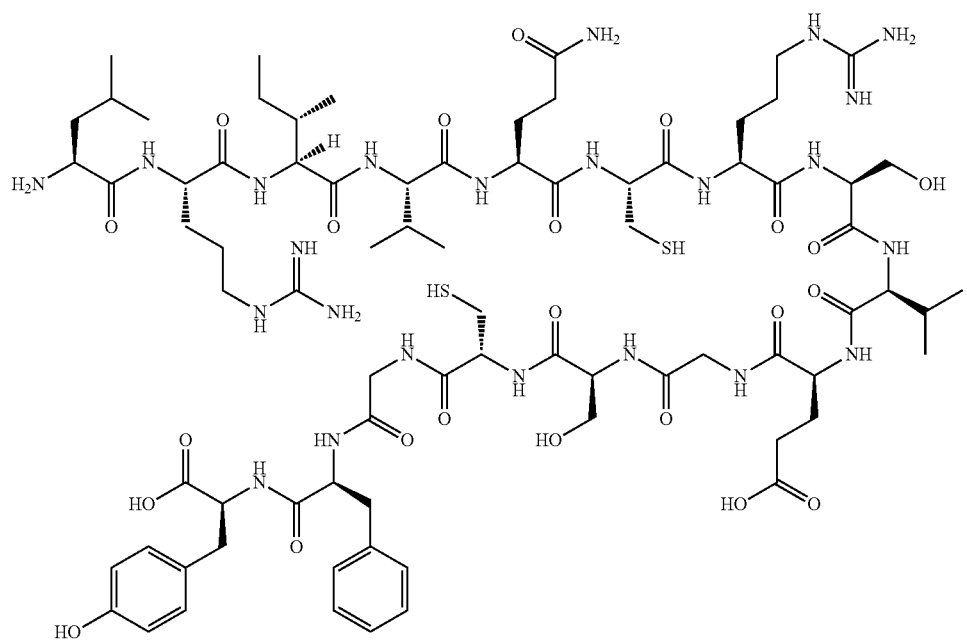
AOD-9604
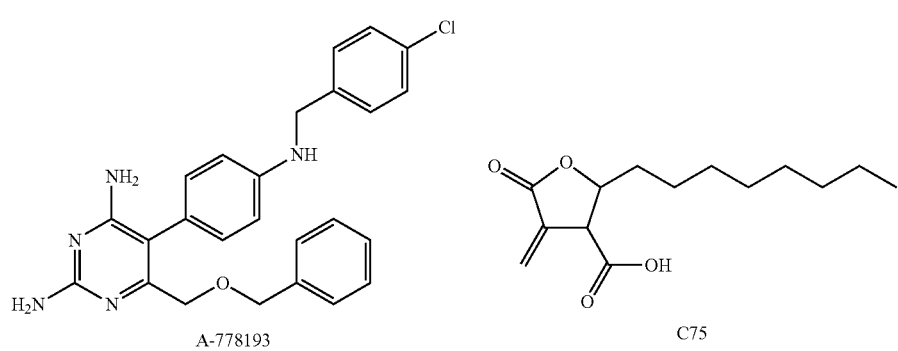
A-778193                    C75
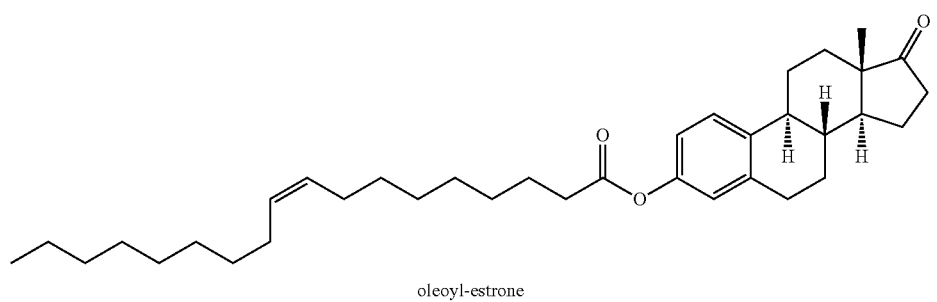
oleoyl-estrone -continued
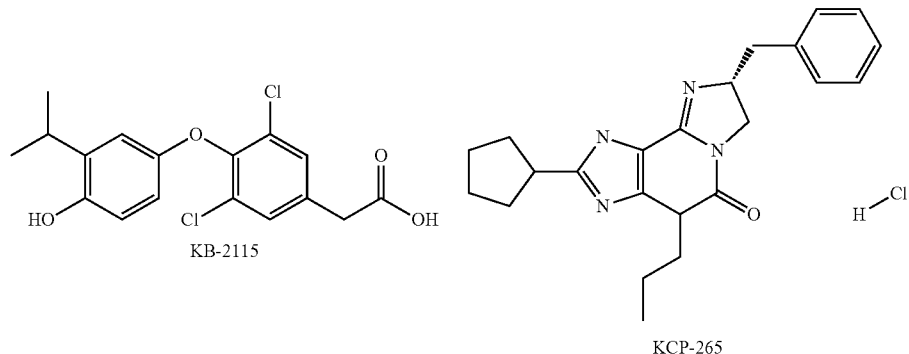
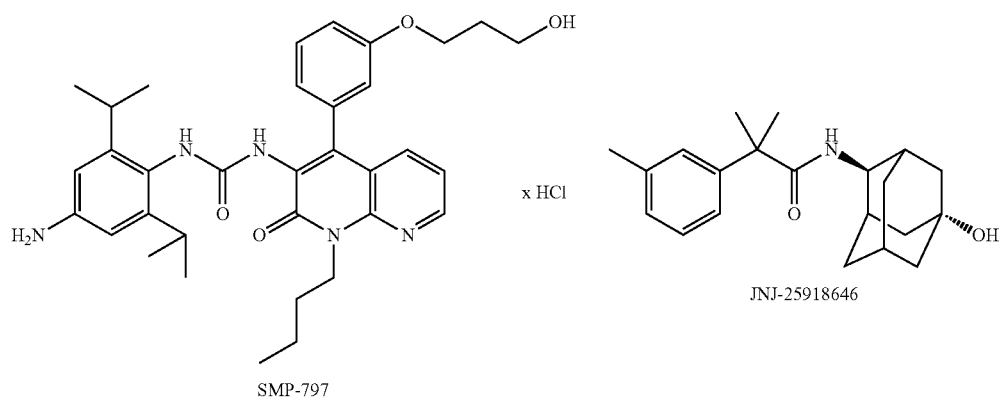
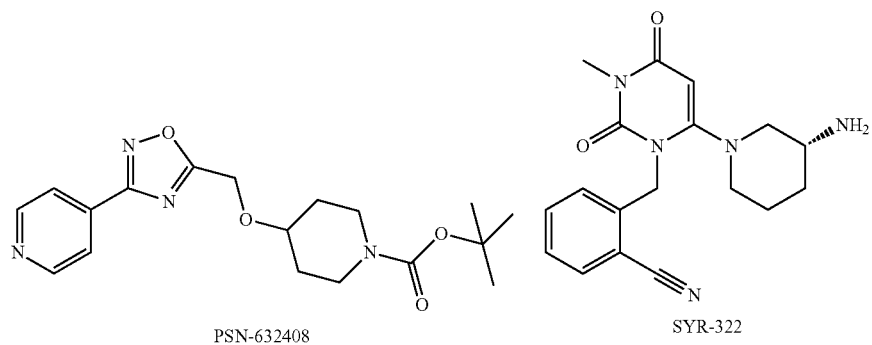
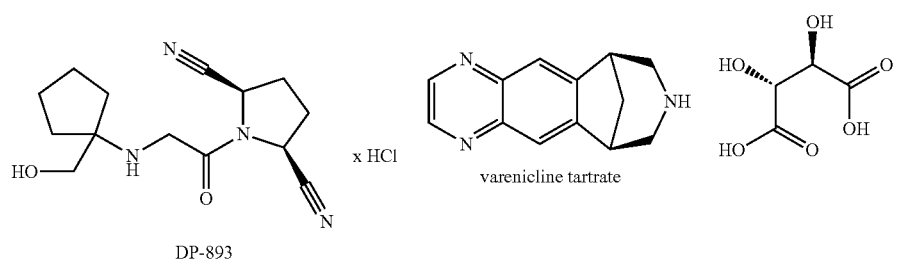

-continued
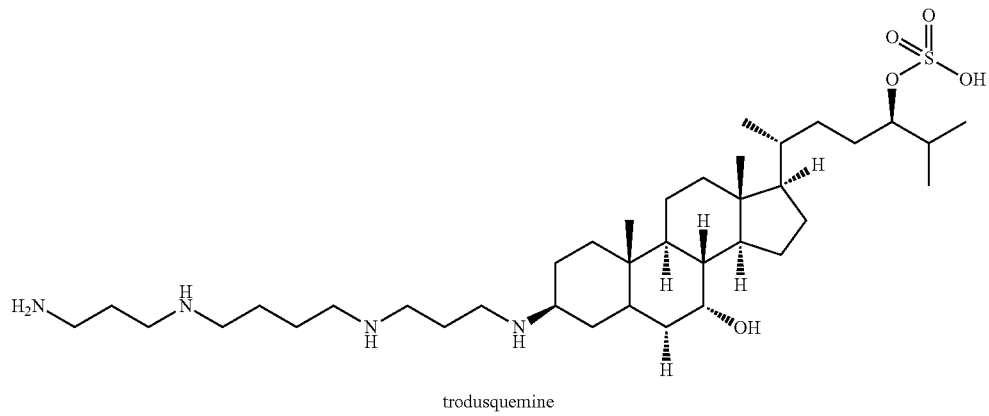
trodusquemine
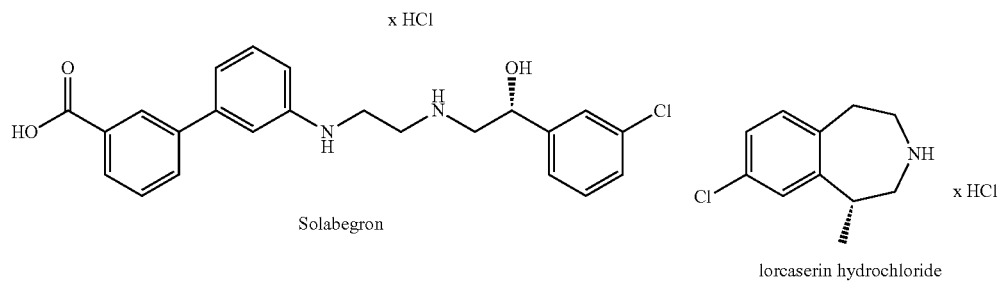
Solabegron x HCl
lorcaserin hydrochloride x HCl
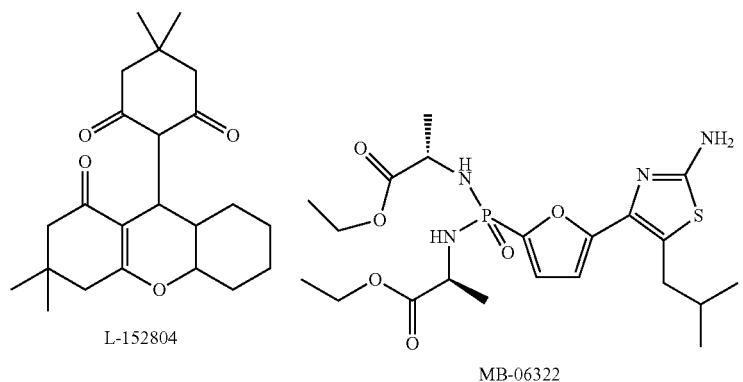
L-152804
MB-06322
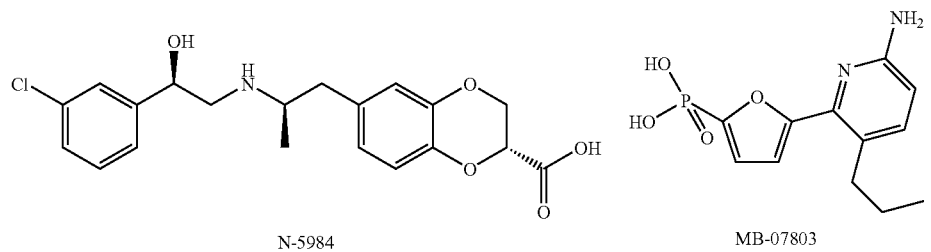
N-5984
MB-07803

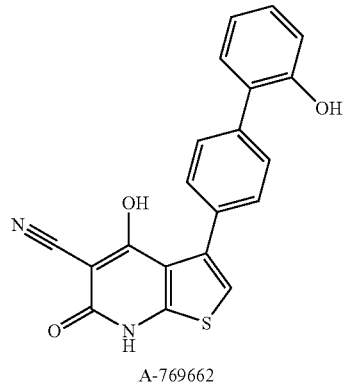
A-769662
EXAMPLES
The examples given below serve to illustrate the invention, but without limiting it.
TABLE 1
| Example | R1 | R2 | R3 | A | R4 | R5 | B | R6 | R7 |
|---------|-----|----|----|----|------|----|----|----|----|
| 1 | CH₃ | H | H | thiazol-2-yl | H | H | tetrahydropyran-4-yl | H | H |
| 2 | CH₃ | H | H | thiazol-2-yl | 5-CH₃ | H | tetrahydropyran-4-yl | H | H |
| 3 | CH₃ | H | H | thiazol-2-yl | 5-Cl | H | tetrahydropyran-4-yl | H | H |
| 4 | CH₃ | H | H | 1,3,4-thiadiazol-2-yl | 3-CH₃ | H | tetrahydropyran-4-yl | H | H |

TABLE 1-continued

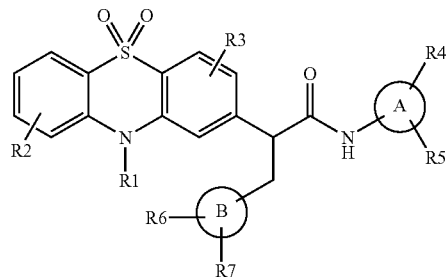

| Example | R1 | R2 | R3 | A | R4 | R5 | B | R6 | R7 |
|---|---|---|---|---|---|---|---|---|---|
| 5 | CH₃ | H | H | pyrazole | 1-CH₃ | H | tetrahydropyran | H | H |
| 6 | CH₃ | H | H | pyridazine | 6-CH₃ | H | tetrahydropyran | H | H |
| 7 | CH₃ | H | H | thiazole | 4-CO₂Et | H | tetrahydropyran | H | H |
| 8 | CH₃ | H | H | thiazole | 4-CH₂—CO₂Et | H | tetrahydropyran | H | H |
| 9 | CH₃ | H | H | thiazole | H | H | cyclopentane | H | H |
| 10 | CH₃ | H | H | thiazole | 4-CH₂—CO₂H | H | tetrahydropyran | H | H |
| 11 | CH₃ | H | H | thiazole | 4-CO₂H | H | tetrahydropyran | H | H |
| 12 | CH₃ | H | H | pyrazole | 1-CH₃ | H | tetrahydrofuran | H | H |

TABLE 1-continued
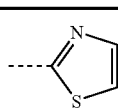
| Example | R1 | R2 | R3 | A | R4 | R5 | B | R6 | R7 |
|---|---|---|---|---|---|---|---|---|---|
| 13 | CH$_3$ | H | H |  | H | H | 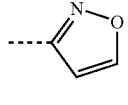 | H | H |
| 14 | CH$_3$ | H | H | 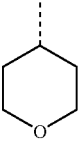 | H | H | 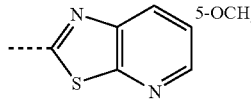 | H | H |
| 15 | CH$_3$ | H | H | 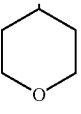 | 5-OCH$_3$ | H | 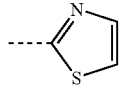 | H | H |
| 16 | CH$_3$ | H | H | 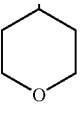 | 4-CH$_3$ | H | 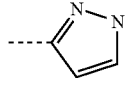 | H | H |
| 17 | CH$_3$ | H | H | 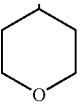 | 1-CH$_2$CO$_2$CH$_2$CH$_3$ | H | 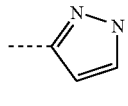 | H | H |
| 18 | CH$_3$ | H | H | 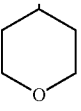 | 1-CH$_2$CO$_2$H | H | 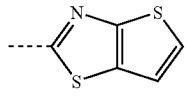 | H | H |
| 19 | CH$_3$ | H | H | 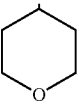 | 6-CO$_2$CH$_3$ | H | 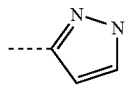 | H | H |
| 20 | CH$_3$ | H | H | 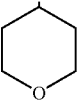 | 1-CH$_2$Ph | H | | H | H |

TABLE 1-continued
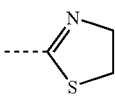
| Example | R1 | R2 | R3 | A | R4 | R5 | B | R6 | R7 |
|---|---|---|---|---|---|---|---|---|---|
| 21 | CH$_3$ | H | H |  | 4-'=O' | H | 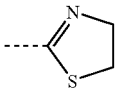 | H | H |
| 22 | CH$_3$ | H | H | 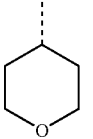 | H | H | 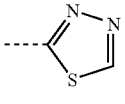 | H | H |
| 23 | CH$_3$ | H | H |  | H | H | 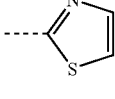 | H | H |
| 24 | CH$_3$ | H | H |  | H | H | 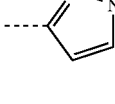 | H | H |
| 25 | CH$_3$ | H | H |  | 1-CH$_3$ | H | 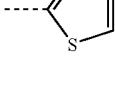 | H | H |
| 26 | CH$_3$ | H | H |  | H | H | 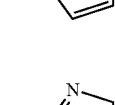 | 3-CH$_3$ | H |
| 27 | CH$_3$ | H | H |  | 1-CH$_3$ | H | 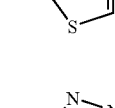 | 3-CH$_3$ | H |
| 28 | CH$_3$ | H | H |  | H | H | 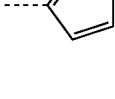 | 3-CH$_3$CH$_2$ | H |
| 29 | CH$_3$ | H | H |  | 1-CH$_3$ | H | | 3-CH$_3$CH$_2$ | H |

TABLE 1-continued
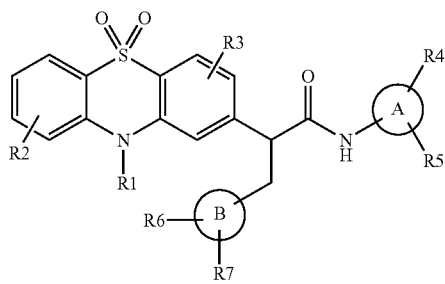
| Example | R1 | R2 | R3 | A | R4 | R5 | B | R6 | R7 |
|---|---|---|---|---|---|---|---|---|---|
| 30 | CH₃ | H | H | thiazol-2-yl | H | H | cyclohexyl | 4-CH₃ | H |
| 31 | CH₃ | H | H | pyrazol-3-yl | 1-CH₃ | H | cyclohexyl | 4-CH₃ | H |
| 32 | CH₃ | H | H | pyrazol-3-yl | 1-CH₃ | H | indanyl | H | H |
| 33 | CH₃ | H | H | thiazolo[5,4-b]pyridin-2-yl | 5-OCH₃ | H | indanyl | H | H |
| 34 | CH₃ | H | H | thiazol-2-yl | H | H | piperidin-3-yl | 1-CH₃ | H |
| 35 | CH₃ | H | H | pyrazol-3-yl | 1-CH₃ | H | piperidin-3-yl | 1-CH₃ | H |
| 36 | CH₃ | H | H | pyrazol-3-yl | 1-CH₃ | H | cyclohexyl | 4-'═O' | H |

TABLE 1-continued
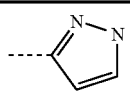
| Example | R1 | R2 | R3 | A | R4 | R5 | B | R6 | R7 |
|---|---|---|---|---|---|---|---|---|---|
| 37 | CH₃ | H | H |  | 1-CH₃ | H | 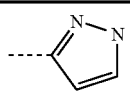 | 4'-'—OH' | H |
| 38 | CH₃ | H | H |  | 1-CH₃ | H | 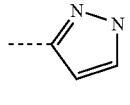 | 4'-'=NOH' | H |
| 39 | CH₃ | H | H | 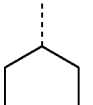 | 5-OCH₃ | H | 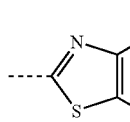 | 1'-'=O' | 1'-'=O' |
| 40 | CH₃ | H | H | 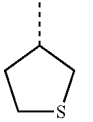 | 1-CH₃ | H | 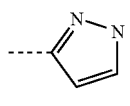 | 3'-'=O' | H |
| 41 | CH₃ | H | H |  | 5-OCH₃ | H | 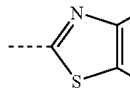 | 3'-'=O' | H |
| 42 | CH₃ | 3-CO₂CH₂CH₃ | H | 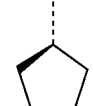 | 1-CH₃ | H | 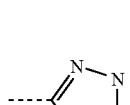 | 3'-'=O' | H |
| 43 | CH₃ | 3-CO₂H | H | 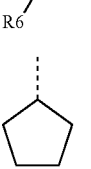 | 1-CH₃ | H | 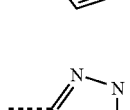 | 3'-'=O' | H |
| 44 | H | H | H |  | 1-CH₃ | H | 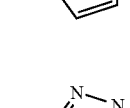 | H | H |
| 45 | H | H | H | 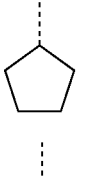 | 1-CH₃ | H |  | 3'-'=O' | H |

TABLE 1-continued

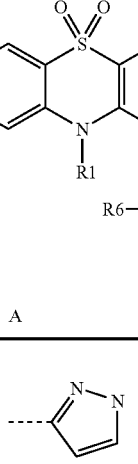

| Example | R1 | R2 | R3 | A | R4 | R5 | B | R6 | R7 |
|---|---|---|---|---|---|---|---|---|---|
| 46 | H | H | H | pyrazole | 1-CH$_3$ | H | cyclopentyl | 3-'=O' | H |
| 47 | H | H | H | thiazolopyridine | 5-OCH$_3$ | H | cyclopentyl | | |
| 48 | H | H | H | thiazolopyridine | 5-OCH$_3$ | H | cyclopentyl | 3-'=O' | H |
| 49 | H | H | H | pyrazole | 1-CH$_2$Ph | H | cyclopentyl | 3-'=O' | H |
| 50 | H | H | H | thiazolopyridine | 5-OCH$_3$ | H | cyclohexyl | 4-F | 4-F |
| 51 | H | H | H | pyrazole | 1-CH$_2$Ph | H | cyclohexyl | 4-F | 4-F |
| 52 | H | H | H | pyrazole | 1-CH$_3$ | H | cyclohexyl | 4-F | 4-F |
| 53 | H | H | H | thiazolopyridine | 5-OCH$_3$ | H | cyclohexenyl | 4-F | H |

TABLE 1-continued

| Example | R1 | R2 | R3 | A | R4 | R5 | B | R6 | R7 |
|---|---|---|---|---|---|---|---|---|---|
| 54 | H | H | H | pyrazole (N-N) | 1-CH₃ | H | cyclohexenyl | 4-F | H |
| 55 | H | H | H | thiazolopyridine | 5-OCH₃ | H | cyclopentyl | 3-F | 3-F |
| 56 | H | H | H | pyrazole (N-N) | 1-CH₃ | H | cyclopentyl | 3-F | 3-F |

The broken line in the radicals A and B indicates the point of attachment of the bond to the ring.

The broken line in the radicals A and B indicates the point of attachment of the bond to the ring.

The activity of the compounds was tested as follows:

Enzymatic Test of Glucokinase Activators

Human Glucokinase

Human glucokinase is expressed as a fusion protein with glutathione S-transferase (GST) in *E. coli* BI21 and purified by affinity chromatography. GSH is cleaved off by digestion with factor Xa, and the glucokinase polypeptide beginning with Ser-6 is obtained. The latter is purified chromatographically. At room temperature, a typical glucokinase preparation has a specific activity of 30 U/mg protein.

Enyzymatic Test

The activity of glucokinase and the effect of compounds on this activity are determined by a coupled optical test at 25° C. The test volume is 100 µl. The test composition is: 25 mM HEPES/NaOH (Merck; #110110) pH 7, 25 mM KCl (Merck; #04933), 2 mM MgCl₂ (Merck; #05833), 1 mM dithiothreitol (Merck; #112013), 1 mM NAD (Sigma; #N1511), 5 mM glucose (Merck; #108337), 1 mM ATP (Sigma; #A2383), 0.1% (w/v) bovine serum albumin (Merck; #112018), 0.002 U glucokinase preparation and 3.2 U glucose 6-phosphate dehydrogenase (Sigma; #G8529). The mixture furthermore contains a test compound. The test compounds are in each case dissolved in 10 mM DMSO and are tested at final concentrations of 0 µM, 0.1 µM, 0.3 µM, 1 µM, 3 µM, 10 µM, 30 µM and 100 µM. The final concentration of DMSO in the test is 1% (v/v). The reaction is started by addition of ATP. The absorption of the mixture at 340 nm is determined immediately after the addition of ATP and then 25 min later using a multiwell plate photometer (from Labsystems, Multiskan Ascent). The change of the absorption during this period is calculated.

Evaluation:

The crude data of the changes in extinction are transferred into a Microsoft Excel file. The value for 0 µM test compound is assigned to be 100%. Dose/activity curves are calculated using the program XL.Fit according to the instructions of the manufacturer (IDBS). The concentration of a test compound which increases the enzymatic activity by 50% is defined as EC150. The maximum fold stimulation corresponds to the ratio of the highest change in extinction in the concentration range of a test compound to the change of the absorption without test substance.

TABLE 2

| | Biological activity | |
|---|---|---|
| Example No | $EC_{150}$ [µM] | Fold induction |
| 1 | 4.2 | 2.0 |
| 5 | 2.1 | 4.4 |
| 6 | 15.5 | 2.1 |
| 9 | 2.2 | 2.8 |
| 15 | 0.9 | 5.0 |
| 36 | 0.5 | 4.0 |
| 41 | 0.7 | 3.9 |
| 42 | 1.2 | 3.6 |
| 46 | 0.6 | 5.0 |
| 54 | 1.0 | 4.5 |

It is evident from the measured data in the table that the compounds according to the invention activate glucokinase.

These compounds are therefore suitable in particular for lowering the blood glucose level and for the treatment of diabetes.

Process

The compounds of the formula I according to the invention can be prepared according to the reaction scheme below:

Process A:

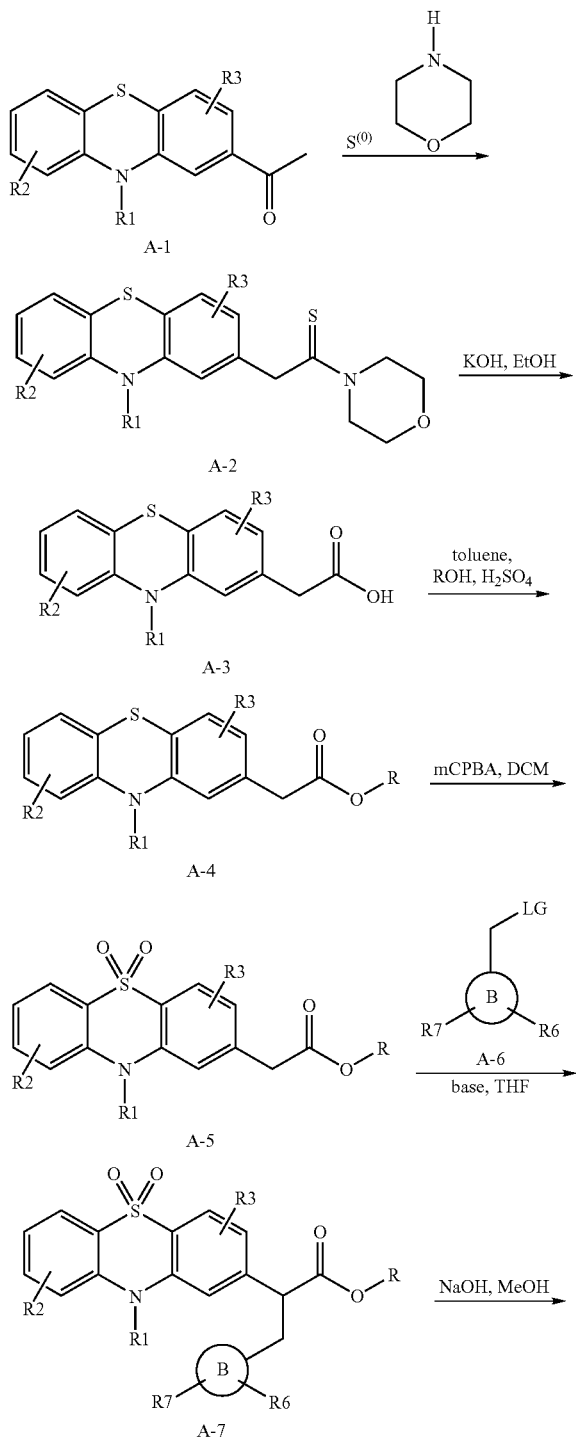

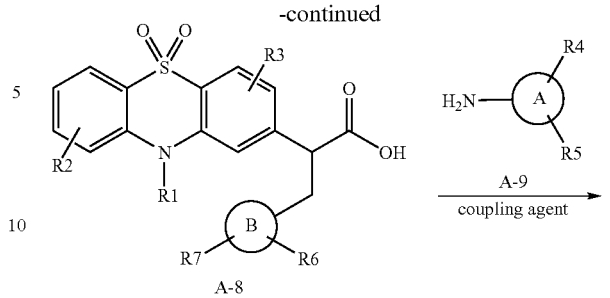

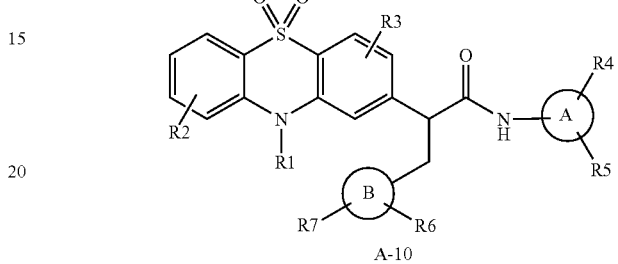

A 1-(phenothiazin-2-yl)ethanone of the general formula A-1 in which R1, R2 and R3 have the meanings given above is reacted with sulfur and morpholine at elevated temperature (120-180° C.) to give the morpholin-4-ylethanethione of the general formula A-2. This is hydrolyzed with a base such as, for example, potassium hydroxide in a polar solvent such as, for example, water and ethanol to give the carboxylic acid of the general formula A-3. The carboxylic acid is converted into the ester of the general formula A-4 by heating the carboxylic acid azeotropically in an alcohol such as, for example, ethanol, in the presence of an acid catalyst such as, for example, sulfuric acid under dehydrating conditions, such as, for example, by boiling on a water separator in a solvent such as, for example, toluene. The compound of the general formula A-4 is reacted with an oxidizing agent such as, for example, meta-chloroperbenzoic acid in an inert solvent such as, for example, dichloromethane to give the phenothiazine of the general formula A-5. The compound of the general formula A-5 is deprotonated with a base such as, for example, potassium hexamethyldisilazide in a polar aprotic solvent such as tetrahydrofuran and alkylated with a compound of the general formula A-6, where B, R6 and R7 have the meanings mentioned above and LG is a leaving group such as, for example, an iodide, bromide, mesylate or tosylate. The resulting compound of the general formula A-7 is hydrolyzed with a base such as, for example, aqueous sodium hydroxide solution in a polar protic solvent mixture such as methanol/water to give the carboxylic acid of the general formula A-8. Under the action of a coupling agent such as, for example, O-[cyano(ethoxycarbonyl)methylenamino]-1,1,3,3-tetramethyluronium tetrafluoroborate (TOTU) or [dimethylamino-([1,2,3]triazolo[4,5-b]pyridin-3-yloxy)methylene]dimethylammonium hexafluorophosphate (HATU)/[1,2,3]triazolo[4,5-b]pyridin-3-ol (HOAT) in the presence of a base such as, for example, diisopropylethylamine in a polar aprotic solvent such as N,N-dimethylformamide, the carboxylic acid of the general formula A-8 is reacted with the amine of the general formula A-9 in which A, R4 and R5 have the meanings described above, to give the amide of the general formula A-10. The racemic compounds of the general formula A-10 can be separated into the enantiomers by chromatography on a chiral phase.

Examples 1-56 were prepared according to process A.
The abbreviations used denote:

| | |
|---|---|
| Ac | acetyl |
| Bn | benzyl |
| iBu | isobutyl |
| tBu | tert-butyl |
| BuLi | n-butyllithium |
| TLC | thin-layer chromatography |
| DCI | direct chemical ionization (in MS) |
| DCM | dichloromethane |
| DMAP | 4-N,N-dimethylaminopyridine |
| DMF | N,N-dimethylformamide |
| DMSO | dimethyl sulfoxide |
| dppp | 1,3-bis(diphenylphosphino)propane |
| EA | ethyl acetate |
| ent | enantiomer/enantiomerically pure |
| EI | electron impact ionization (in MS) |
| eq | equivalent |
| ESI | electron spray ionization (in MS) |
| Et | ethyl |
| GC | gas chromatography |
| HATU | [dimethylamino-([1,2,3]triazolo[4,5-b]pyridin-3-yloxy)methylene]-dimethylammonium hexafluorophosphate |
| HOAT | [1,2,3]triazolo[4,5-b]pyridin-3-ol |
| HPLC | high pressure, high performance liquid chromatography |
| LiHMDS | lithium hexamethyldisilazide |
| LC-MS | liquid chromatography-coupled mass spectroscopy |
| m | meta |
| M | molar |
| mCPBA | meta-chloroperbenzoic acid |
| Me | methyl |
| MeCN | acetonitrile |
| MS | mass spectroscopy |
| NMR | nuclear magnetic resonance spectroscopy |
| o | ortho |
| p | para |
| Pd/C | palladium on carbon |
| Ph | phenyl |
| iPr | isopropyl |
| nPr | n-propyl |
| rac | racemic/racemic mixture |
| Rf | retention time (in TLC) |
| RP | reversed phase |
| tert | tertiary |
| THF | tetrahydrofuran |
| TOTU | O-[cyano(ethoxycarbonyl)methylenamino]-1,1,3,3-tetramethyluronium tetrafluoroborate |

Exemplary syntheses according to process A

Example 1

2-(10-Methyl-5,5-dioxo-5,10-dihydrophenothiazin-2-yl)-3-(tetrahydropyran-4-yl)-N-thiazol-2-ylpropionamide

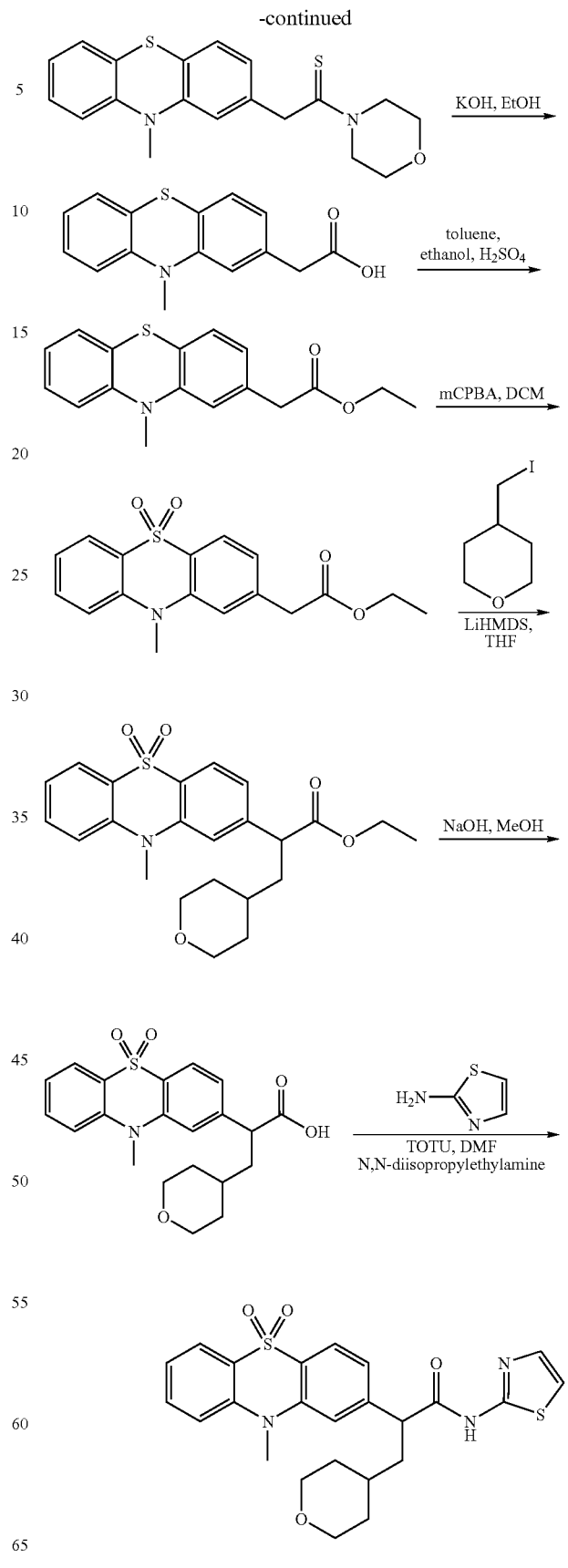

2-(10-Methyl-10H-phenothiazin-2-yl)-1-morpholin-4-ylethanethione

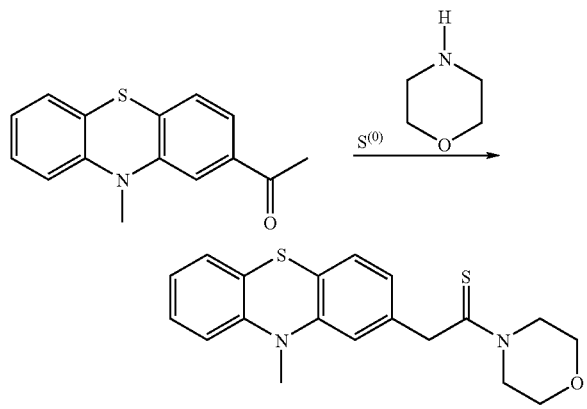

7.08 g of sulfur and 15.57 ml of morpholine are added to 22.7 g of 1-(10-methyl-10H-phenothiazin-2-yl)ethanone. The reaction mixture is stirred at 150° C. for two and a half hours. The reaction mixture is cooled in an ice bath and stirred with ethyl acetate and ethanol. The resulting precipitate is filtered off with suction and the filtrate is concentrated under reduced pressure until another precipitate is formed. This is again filtered off with suction. The precipitates are combined and dried under reduced pressure. This gives 30.2 g of 2-(10-methyl-10H-phenothiazin-2-yl)-1-morpholin-4-ylethanethione as an orange solid.

$C_{19}H_{20}N_2OS_2$ (356.51), LCMS (ESI): 357.1 (M+H$^+$), Rf (n-heptane:ethyl acetate=3:1)=0.12.

(10-Methyl-10H-phenothiazin-2-yl)acetic acid

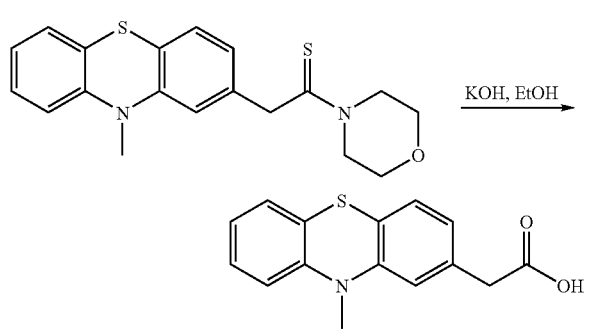

30.2 g of 2-(10-methyl-10H-phenothiazin-2-yl)-1-morpholin-4-ylethanethione are heated at the boil under reflux in a solution of 50 ml 50% strength aqueous potassium hydroxide solution and 100 ml of ethanol for twelve hours. The reaction mixture is cooled in an ice bath and acidified to pH 3 with concentrated hydrochloric acid. The product is then extracted three times with in each case 250 ml of ethyl acetate. The combined organic phases are dried over MgSO$_4$ and then concentrated under reduced pressure. This gives 18.0 g of (10-methyl-10H-phenothiazin-2-yl)acetic acid as a yellow oil.

$C_{15}H_{13}NO_2S$ (271.34), LCMS (ESI): 271.95 (M+H$^+$), Rf (n-heptane:ethyl acetate 1:1)=0.26.

Ethyl (10-methyl-10H-phenothiazin-2-yl)acetate

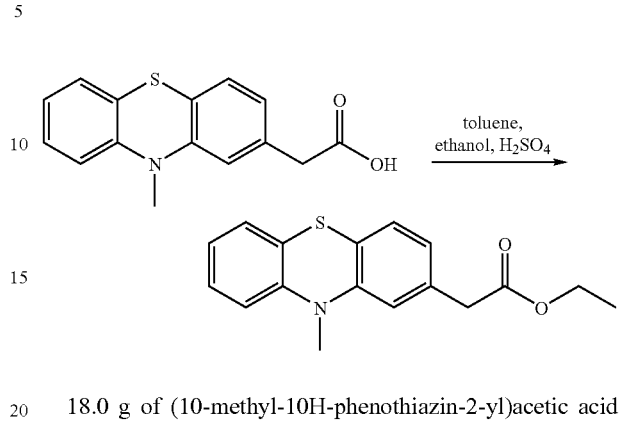

18.0 g of (10-methyl-10H-phenothiazin-2-yl)acetic acid are dissolved in a mixture of 400 ml of toluene and 200 ml of ethanol, and 5 ml of concentrated sulfuric acid are added. In a water separator filled with molecular sieve, the reaction mixture is heated at the boil under reflux for twelve hours. The reaction mixture is then cooled in an ice bath, and 200 ml of water are added. The mixture is then neutralized by addition of solid sodium carbonate. The product is then extracted five times with in each case 250 ml of ethyl acetate. The combined organic phases are dried over MgSO$_4$ and then concentrated under reduced pressure. The residue is purified on silica gel using the mobile phase n-heptane=>n-heptane:ethyl acetate=10:1. This gives 17.0 g of ethyl (10-methyl-10H-phenothiazin-2-yl)acetate as a yellow oil. $C_{17}H_{17}NO_2S$ (299.39), LCMS (ESI): 300.1 (M+H$^+$), Rf (n-heptane:ethyl acetate=3:1)=0.34.

Ethyl (10-methyl-5,5-dioxo-5,10-dihydrophenothiazin-2-yl)acetate

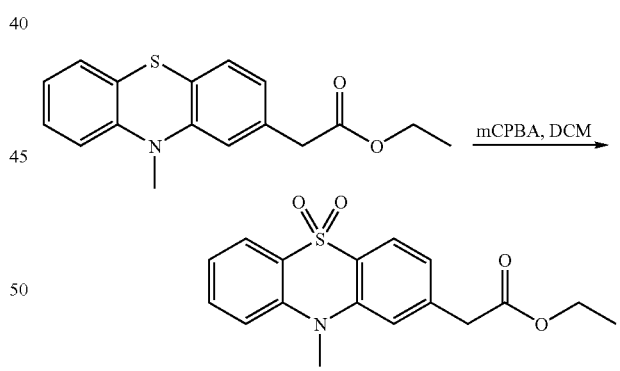

17.0 g of ethyl (10-methyl-10H-phenothiazin-2-yl)acetate are dissolved in 300 ml of dichloromethane, and 35.0 g of mCPBA are added a little at a time. The reaction mixture is stirred at room temperature for one hour. The reaction mixture is then washed with 100 ml of saturated NaHCO$_3$ solution, 5× with in each case 100 ml of 2 M NaOH and once with 100 ml of saturated NaCl solution and dried over MgSO$_4$, and the solvent is then removed under reduced pressure. This gives 6.7 g of ethyl (10-methyl-5,5-dioxo-5,10-dihydrophenothiazin-2-yl)acetate as a yellow oil which slowly crystallizes on standing.

$C_{17}H_{17}NO_4S$ (331.39), LCMS (ESI): 332.1 (M+H$^+$), Rf (n-heptane:EA=1:1)=0.49.

Ethyl 2-(10-methyl-5,5-dioxo-5,10-dihydrophenothiazin-2-yl)-3-(tetrahydropyran-4-yl)propionate

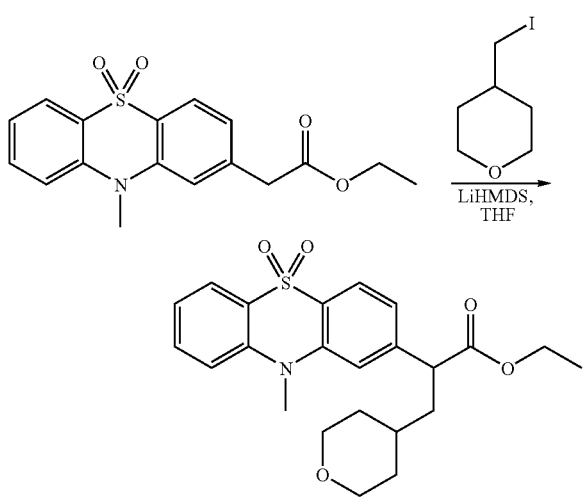

Under argon, 1.66 ml of 1,1,1,3,3,3-hexamethyldisilazane are dissolved in 20 ml of tetrahydrofuran. With ice cooling, 2.90 ml of n-butyllithium (2.5 M in n-hexane) are added dropwise, and the mixture is stirred at 0° C. for another 30 minutes. At −78° C., this solution is then added dropwise to a stirred solution of 2.0 g of ethyl (10-methyl-5,5-dioxo-5,10-dihydrophenothiazin-2-yl)acetate in 100 ml of tetrahydrofuran. The reaction mixture is stirred at −78° C. for 20 minutes, and 2.0 g of 4-(iodomethyl)tetrahydro-2H-pyran are then added dropwise. The cooling bath is removed and the mixture is allowed to slowly warm to room temperature. The reaction mixture is stirred at room temperature overnight. 10 ml of water are then added, the tetrahydrofuran is removed under reduced pressure and the residue is extracted three times with in each case 100 ml of ethyl acetate. The combined organic phases are dried over MgSO₄ and then concentrated under reduced pressure. The residue is purified on silica gel using the mobile phase n-heptane:ethyl acetate (100%:0%)=>n-heptane:ethyl acetate (0%:100%). This gives 2.0 g of ethyl 2-(10-methyl-5,5-dioxo-5,10-dihydrophenothiazin-2-yl)-3-(tetrahydropyran-4-yl)propionate as a colorless solid.

C23H27NO5S (429.54), LCMS (ESI): 430.2 (M+H⁺).

2-(10-Methyl-5,5-dioxo-5,10-dihydrophenothiazin-2-yl)-3-(tetrahydropyran-4-yl)propionic Acid

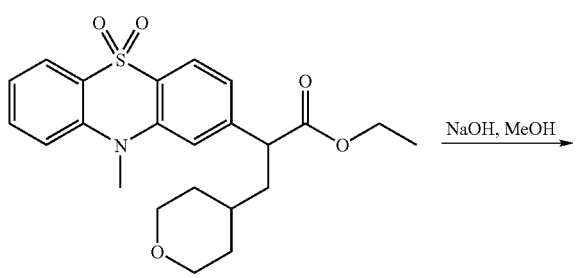

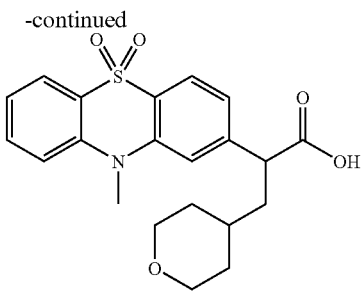

2.0 g of ethyl 2-(10-methyl-5,5-dioxo-5,10-dihydrophenothiazin-2-yl)-3-(tetrahydropyran-4-yl)propionate are suspended in 100 ml of methanol, and 32.1 ml of a 2M NaOH solution are added. The reaction mixture is stirred at 80° C. for one hour. The methanol is removed under reduced pressure and the reaction mixture is adjusted to pH 4 by addition of concentrated hydrochloric acid. The mixture is extracted three times with in each case 100 ml of ethyl acetate. The combined organic phases are dried over MgSO₄ and then concentrated under reduced pressure. This gives 1.85 g of 2-(10-methyl-5,5-dioxo-5,10-dihydrophenothiazin-2-yl)-3-(tetrahydropyran-4-yl)propionic acid as a solid.

C21H23NO5S (401.49), LCMS (ESI): 402.2 (M+H⁺).

2-(10-Methyl-5,5-dioxo-5,10-dihydrophenothiazin-2-yl)-3-(tetrahydropyran-4-yl)-N-thiazol-2-ylpropionamide

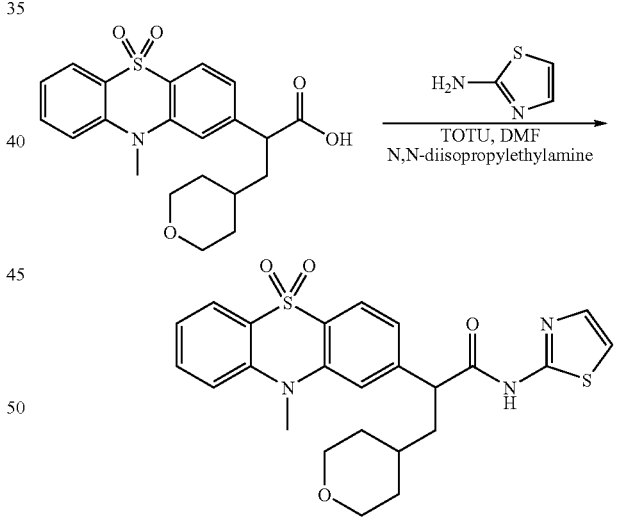

200 mg of 2-(10-methyl-5,5-dioxo-5,10-dihydrophenothiazin-2-yl)-3-(tetrahydropyran-4-yl)propionic acid, 74.8 mg of commercially available 2-aminothiazole and 220 µl of N,N-diisopropylethylamine are dissolved in 10 ml of dimethylformamide. 212 mg of TOTU are added, and the mixture is stirred at room temperature overnight. The reaction mixture is then diluted by addition of 50 ml of ethyl acetate and washed five times with in each case 30 ml of saturated sodium bicarbonate solution. The organic phase is dried over MgSO₄, and the solvent is then removed under reduced pressure. The residue is purified by RP-HPLC. This gives 141 mg of 2-(10- methyl-5,5-dioxo-5,10-dihydrophenothiazin-2-yl)-3-(tetrahydropyran-4-yl)-N-thiazol-2-ylpropionamide as a colorless lyophilisate.

C24H25N3O4S2 (483.61), LCMS (ESI): 484.1 (M+H⁺).

Example 2

2-(10-Methyl-5,5-dioxo-5,10-dihydrophenothiazin-2-yl)-N-(5-methylthiazol-2-yl)-3-(tetrahydropyran-4-yl)propionamide

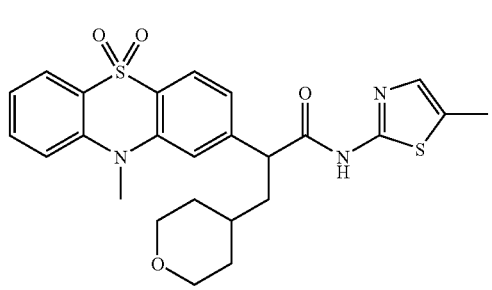

Analogously to Example 1, 2-(10-methyl-5,5-dioxo-5,10-dihydrophenothiazin-2-yl)-3-(tetrahydropyran-4-yl)propionic acid and commercially available 2-amino-5-methylthiazole give 2-(10-methyl-5,5-dioxo-5,10-dihydrophenothiazin-2-yl)-N-(5-methylthiazol-2-yl)-3-(tetrahydropyran-4-yl)propionamide.

C25H27N3O4S2 (497.64), LCMS (ESI): 498.1 (M+H⁺).

Example 3

N-(5-Chlorothiazol-2-yl)-2-(10-methyl-5,5-dioxo-5,10-dihydrophenothiazin-2-yl)-3-(tetrahydropyran-4-yl)propionamide

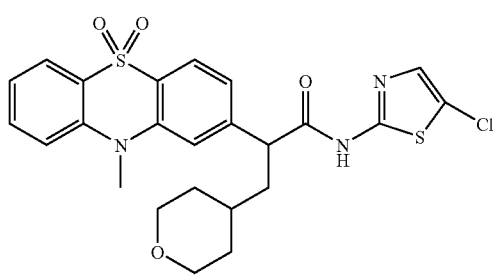

Analogously to Example 1, 2-(10-methyl-5,5-dioxo-5,10-dihydrophenothiazin-2-yl)-3-(tetrahydropyran-4-yl)propionic acid and commercially available 2-amino-5-chloro-thiazole hydrochloride give N-(5-chlorothiazol-2-yl)-2-(10-methyl-5,5-dioxo-5,10-dihydrophenothiazin-2-yl)-3-(tetrahydropyran-4-yl)propionamide.

C24H24ClN3O4S2 (518.06), LCMS (ESI): 518.1 (M+H⁺).

Example 4

2-(10-Methyl-5,5-dioxo-5,10-dihydrophenothiazin-2-yl)-N-(3-methyl-[1,2,4]thiadiazol-5-yl)-3-(tetrahydropyran-4-yl)propionamide

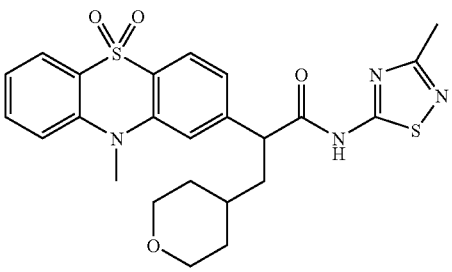

Analogously to Example 1, 2-(10-methyl-5,5-dioxo-5,10-dihydrophenothiazin-2-yl)-3-(tetrahydropyran-4-yl)propionic acid and commercially available 3-methyl-[1,2,4]thiadiazol-5-ylamine give 2-(10-methyl-5,5-dioxo-5,10-dihydrophenothiazin-2-yl)-N-(3-methyl-[1,2,4]thiadiazol-5-yl)-3-(tetrahydropyran-4-yl)propionamide.

C24H26N4O4S2 (498.63), LCMS (ESI): 499.2 (M+H⁺).

Example 5

2-(10-Methyl-5,5-dioxo-5,10-dihydrophenothiazin-2-yl)-N-(1-methyl-1H-pyrazol-3-yl)-3-(tetrahydropyran-4-yl)propionamide

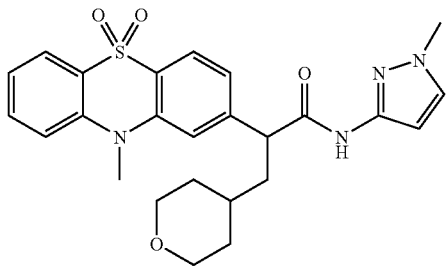

Analogously to Example 1, 2-(10-methyl-5,5-dioxo-5,10-dihydrophenothiazin-2-yl)-3-(tetrahydropyran-4-yl)propionic acid and commercially available 1-methyl-1H-pyrazol-3-amine give 2-(10-methyl-5,5-dioxo-5,10-dihydrophenothiazin-2-yl)-N-(1-methyl-1H-pyrazol-3-yl)-3-(tetrahydropyran-4-yl)propionamide.

C25H28N4O4S (480.59), LCMS (ESI): 481.2 (M+H⁺).

Example 6

2-(10-Methyl-5,5-dioxo-5,10-dihydrophenothiazin-2-yl)-N-(6-methylpyridazin-3-yl)-3-(tetrahydropyran-4-yl)propionamide

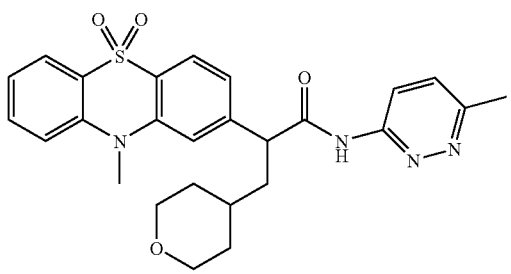

Analogously to Example 1, 2-(10-methyl-5,5-dioxo-5,10-dihydrophenothiazin-2-yl)-3-(tetrahydropyran-4-yl)propionic acid and commercially available 6-methyl-3-pyridazinamine give 2-(10-methyl-5,5-dioxo-5,10-dihydrophenothiazin-2-yl)-N-(6-methylpyridazin-3-yl)-3-(tetrahydropyran-4-yl)propionamide.

$C_{26}H_{28}N_4O_4S$ (492.60), LCMS (ESI): 493.2 (M+H$^+$).

Example 7

Ethyl 2-[2-(10-methyl-5,5-dioxo-5,10-dihydrophenothiazin-2-yl)-3-(tetrahydropyran-4-yl)propionylamino]thiazole-4-carboxylate

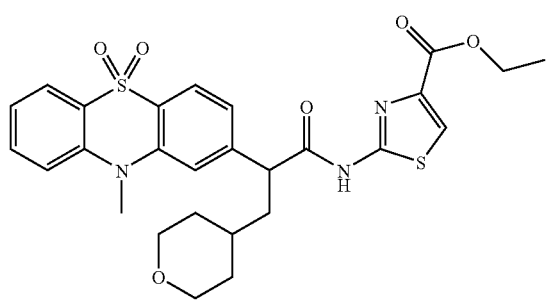

Analogously to Example 1, 2-(10-methyl-5,5-dioxo-5,10-dihydrophenothiazin-2-yl)-3-(tetrahydropyran-4-yl)propionic acid and commercially available ethyl 2-aminothiazole-4-carboxylate give ethyl 2-[2-(10-methyl-5,5-dioxo-5,10-dihydrophenothiazin-2-yl)-3-(tetrahydropyran-4-yl)propionylamino]thiazole-4-carboxylate.

$C_{27}H_{29}N_3O_6S_2$ (555.68), LCMS (ESI): 597.20(M+MeCN+H$^+$).

Example 8

Ethyl {2-[2-(10-methyl-5,5-dioxo-5,10-dihydrophenothiazin-2-yl)-3-(tetrahydropyran-4-yl)propionylamino]thiazol-4-yl}acetate

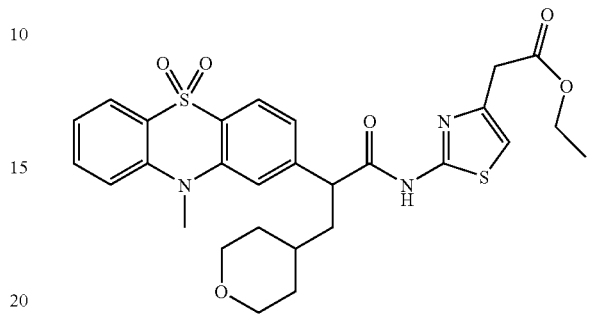

Analogously to Example 1, 2-(10-methyl-5,5-dioxo-5,10-dihydrophenothiazin-2-yl)-3-(tetrahydropyran-4-yl)propionic acid and commercially available ethyl 2-aminothiazole-4-acetate give ethyl {2-[2-(10-methyl-5,5-dioxo-5,10-dihydrophenothiazin-2-yl)-3-(tetrahydropyran-4-yl)propionylamino]thiazol-4-yl}acetate.

$C_{28}H_{31}N_3O_6S_2$ (569.70), LCMS (ESI): 570.20(M+H$^+$).

Example 9

3-Cyclopentyl-2-(10-methyl-5,5-dioxo-5,10-dihydrophenothiazin-2-yl)-N-thiazol-2-yl-propionamide

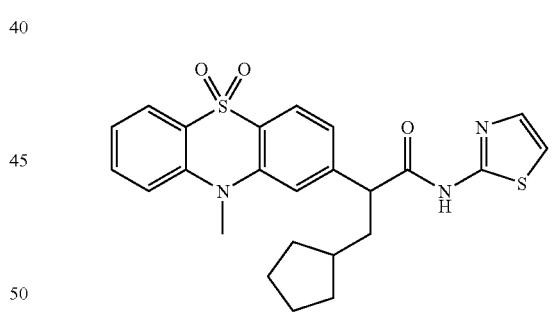

Analogously to Example 1, ethyl (10-methyl-5,5-dioxo-5,10-dihydrophenothiazin-2-yl)acetate, commercially available iodomethylcyclopentane and commercially available 2-aminothiazole give 3-cyclopentyl-2-(10-methyl-5,5-dioxo-5,10-dihydrophenothiazin-2-yl)-N-thiazol-2-ylpropionamide.

$C_{24}H_{25}N_3O_3S_2$ (467.61), LCMS (ESI): 468.2 (M+H$^+$), 509.3 (M+MeCN+H$^+$).

On a chiral phase (Chiralpak AS-H 43) using the mobile phase n-heptane:methanol:ethanol=10:1:1 (column preconditioned with trifluoroacetic acid), the racemic mixture is separated into the enantiomers (Rt=13.66 min and Rt=16.58 min).

Example 10

{2-[2-(10-Methyl-5,5-dioxo-5,10-dihydrophenothiazin-2-yl)-3-(tetrahydropyran-4-yl)propionylamino]thiazol-4-yl}acetic Acid

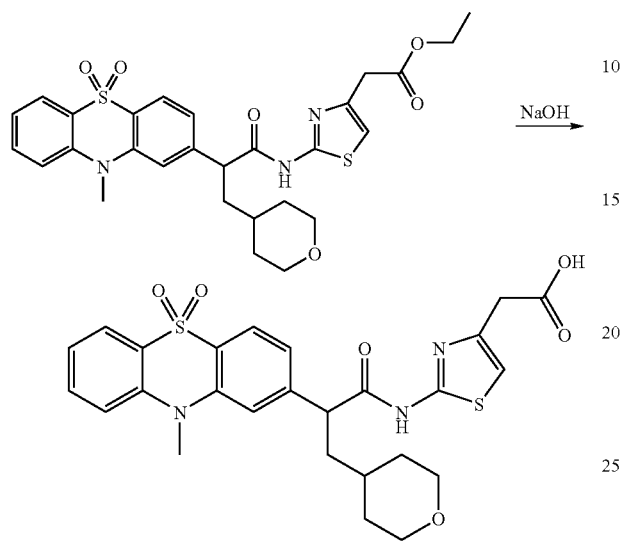

At room temperature and with stirring, 0.25 ml of 2M NaOH are added to a suspension of 25.0 mg of ethyl {2-[2-(10-methyl-5,5-dioxo-5,10-dihydrophenothiazin-2-yl)-3-(tetrahydropyran-4-yl)propionylamino]thiazol-4-yl}acetate in 5 ml of tetrahydrofuran and 2 ml of water, and the mixture is stirred at room temperature for 12 hours. The reaction mixture is then neutralized by addition of 1M HCl. The solvents are removed under reduced pressure, and the residue is taken up in 20 ml of ethyl acetate and washed three times with in each case 10 ml of water. The organic phase is dried with $MgSO_4$ and concentrated under reduced pressure. The residue is purified by RP-HPLC. This gives 22.5 mg of {2-[2-(10-methyl-5,5-dioxo-5,10-dihydrophenothiazin-2-yl)-3-(tetrahydropyran-4-yl)propionylamino]thiazol-4-yl}acetic acid as a lyophilisate.

$C_{26}H_{27}N_3O_6S_2$ (541.65), LCMS (ESI): 542.2 (M+H$^+$).

Example 11

2-[2-(10-Methyl-5,5-dioxo-5,10-dihydrophenothiazin-2-yl)-3-(tetrahydropyran-4-yl)propionylamino]thiazole-4-carboxylic Acid

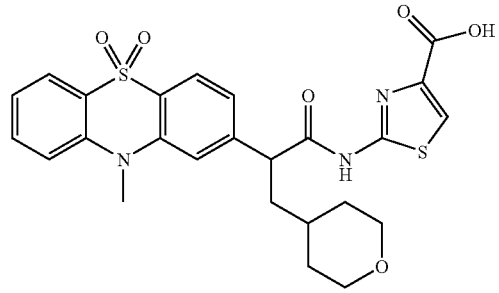

Analogously to Example 10, ethyl 2-[2-(10-methyl-5,5-dioxo-5,10-dihydrophenothiazin-2-yl)-3-(tetrahydropyran-4-yl)propionylamino]thiazol-4-carboxylate gives 2-[2-(10-methyl-5,5-dioxo-5,10-dihydrophenothiazin-2-yl)-3-(tetrahydropyran-4-yl)propionylamino]thiazol-4-carboxylic acid.

$C_{25}H_{25}N_3O_6S_2$ (527.62), LCMS (ESI): 528.2 (M+H$^+$), 569.2 (M+MeCN+H$^+$).

Example 12

2-(10-Methyl-5,5-dioxo-5,10-dihydrophenothiazin-2-yl)-N-(1-methyl-1H-pyrazol-3-yl)-3-(tetrahydrofuran-3-yl)propionamide

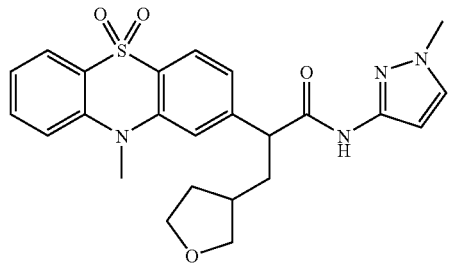

Analogously to Example 1, ethyl (10-methyl-5,5-dioxo-5,10-dihydrophenothiazin-2-yl)acetate, commercially available 3-iodomethyltetrahydrofuran and commercially available 1-methyl-1H-pyrazole-3-amine give 2-(10-methyl-5,5-dioxo-5,10-dihydrophenothiazin-2-yl)-N-(1-methyl-1H-pyrazol-3-yl)-3-(tetrahydrofuran-3-yl)propionamide.

$C_{24}H_{26}N_4O_4S$ (466.56), LCMS (ESI): 467.2 (M+H$^+$).

Example 13

2-(10-Methyl-5,5-dioxo-5,10-dihydrophenothiazin-2-yl)-3-(tetrahydrofuran-3-yl)-N-thiazol-2-ylpropionamide

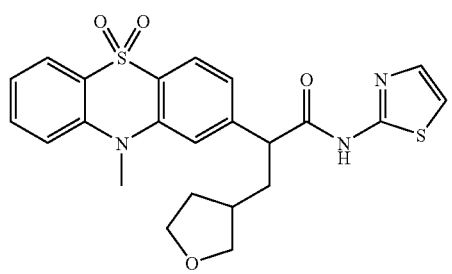

Analogously to Example 1, ethyl (10-methyl-5,5-dioxo-5,10-dihydrophenothiazin-2-yl)acetate, commercially available 3-iodomethyltetrahydrofuran and commercially available 2-aminothiazole give 2-(10-methyl-5,5-dioxo-5,10-dihydrophenothiazin-2-yl)-3-(tetrahydrofuran-3-yl)-N-thiazol-2-ylpropionamide.

$C_{23}H_{23}N_3O_4S_2$ (469.59), LCMS (ESI): 470.1 (M+H$^+$).

Example 14

N-Isoxazol-3-yl-2-(10-methyl-5,5-dioxo-5,10-dihydrophenothiazin-2-yl)-3-(tetrahydropyran-4-yl)propionamide

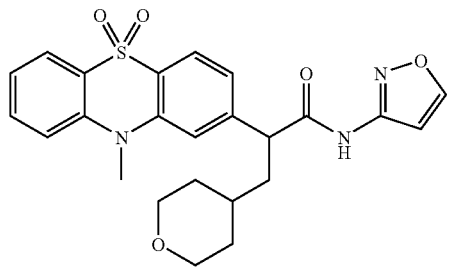

Analogously to Example 1, 2-(10-methyl-5,5-dioxo-5,10-dihydrophenothiazin-2-yl)-3-(tetrahydropyran-4-yl)propionic acid and commercially available 3-aminoisoxazole give N-isoxazol-3-yl-2-(10-methyl-5,5-dioxo-5,10-dihydrophenothiazin-2-yl)-3-(tetrahydropyran-4-yl)propionamide.

$C_{24}H_{25}N_3O_5S$ (467.55), LCMS (ESI): 468.3 (M+H$^+$).

Example 15

N-(5-Methoxy-thiazolo[5,4-b]pyridin-2-yl)-2-(10-methyl-5,5-dioxo-5,10-dihydrophenothiazin-2-yl)-3-(tetrahydropyran-4-yl)propionamide

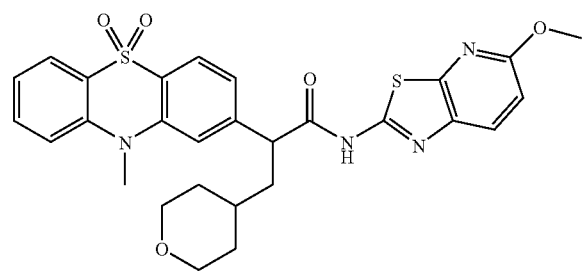

Analogously to Example 1, 2-(10-methyl-5,5-dioxo-5,10-dihydrophenothiazin-2-yl)-3-(tetrahydropyran-4-yl)propionic acid and 5-methoxythiazolo[5,4-b]pyridin-2-ylamine give N-(5-methoxy-thiazolo[5,4-b]pyridin-2-yl)-2-(10-methyl-5,5-dioxo-5,10-dihydrophenothiazin-2-yl)-3-(tetrahydropyran-4-yl)propionamide.

$C_{28}H_{28}N_4O_5S_2$ (564.69), LCMS (ESI): 565.2 (M+H$^+$).

Example 16

2-(10-Methyl-5,5-dioxo-5,10-dihydrophenothiazin-2-yl)-N-(4-methylthiazol-2-yl)-3-(tetrahydropyran-4-yl)propionamide

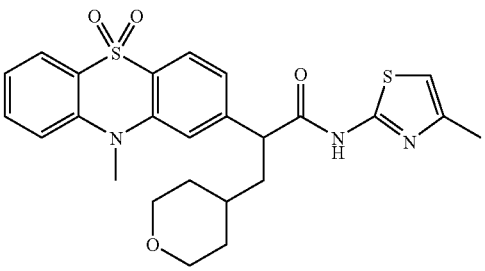

Analogously to Example 1, 2-(10-methyl-5,5-dioxo-5,10-dihydrophenothiazin-2-yl)-3-(tetrahydropyran-4-yl)propionic acid and commercially available 2-amino-4-methylthiazole hydrochloride give 2-(10-methyl-5,5-dioxo-5,10-dihydrophenothiazin-2-yl)-N-(4-methylthiazol-2-yl)-3-(tetrahydropyran-4-yl)propionamide.

$C_{25}H_{27}N_3O_4S_2$ (497.64), LCMS (ESI): 498.1 (M+H$^+$).

Example 17

Ethyl {3-[2-(10-methyl-5,5-dioxo-5,10-dihydrophenothiazin-2-yl)-3-(tetrahydropyran-4-yl)propionylamino]pyrazol-1-yl}acetate

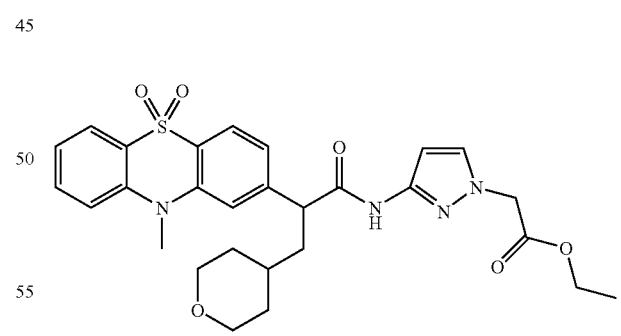

Analogously to Example 1, 2-(10-methyl-5,5-dioxo-5,10-dihydrophenothiazin-2-yl)-3-(tetrahydropyran-4-yl)propionic acid and commercially available ethyl (3-aminopyrazol-1-yl)acetate hydrochloride give ethyl {3-[2-(10-methyl-5,5-dioxo-5,10-dihydrophenothiazin-2-yl)-3-(tetrahydropyran-4-yl)propionylamino]pyrazol-1-yl}acetate.

$C_{28}H_{32}N_4O_6S$ (552.65), LCMS (ESI): 553.3 (M+H$^+$).

Example 18

{3-[2-(10-Methyl-5,5-dioxo-5,10-dihydrophenothi-azin-2-yl)-3-(tetrahydropyran-4-yl)propionylamino]pyrazol-1-yl}acetic Acid

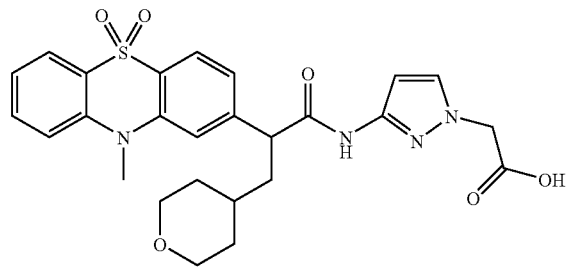

Analogously to Example 10, ethyl {3-[2-(10-methyl-5,5-dioxo-5,10-dihydrophenothiazin-2-yl)-3-(tetrahydropyran-4-yl)propionylamino]pyrazol-1-yl}acetate gives {3-[2-(10-methyl-5,5-dioxo-5,10-dihydrophenothiazin-2-yl)-3-(tetrahydropyran-4-yl)propionylamino]pyrazol-1-yl}acetic acid.

C26H28N4O6S (524.60), LCMS (ESI): 525.2 (M+H$^+$).

Example 19

Methyl 2-[2-(10-methyl-5,5-dioxo-5,10-dihydrophenothiazin-2-yl)-3-(tetrahydropyran-4-yl)propionylamino]thieno[2,3-d]thiazole-6-carboxylate

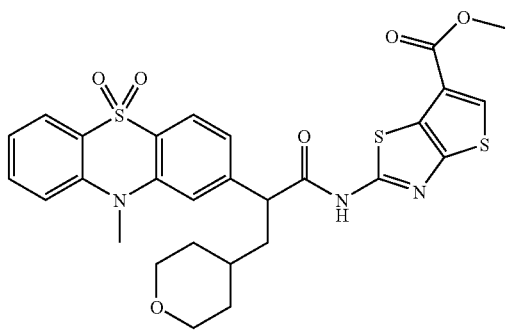

Analogously to Example 1, 2-(10-methyl-5,5-dioxo-5,10-dihydrophenothiazin-2-yl)-3-(tetrahydropyran-4-yl)propionic acid and commercially available methyl 2-aminothieno[2,3-d]thiazole-6-carboxylate give methyl 2-[2-(10-methyl-5,5-dioxo-5,10-dihydrophenothiazin-2-yl)-3-(tetrahydropyran-4-yl)propionylamino]thieno[2,3-d]thiazole-6-carboxylate.

C28H27N3O6S3 (597.74), LCMS (ESI): 598.3 (M+H$^+$).

Example 20

N-(1-Benzyl-1H-pyrazol-3-yl)-2-(10-methyl-5,5-dioxo-5,10-dihydrophenothiazin-2-yl)-3-(tetrahydropyran-4-yl)propionamide

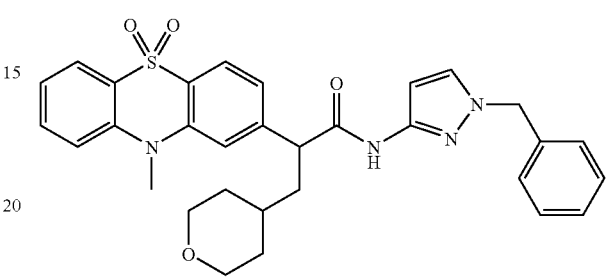

Analogously to Example 1, 2-(110-methyl-5,5-dioxo-5,10-dihydrophenothiazin-2-yl)-3-(tetrahydropyran-4-yl)propionic acid and commercially available 1-benzyl-1H-pyrazol-3-ylamine give N-(1-benzyl-1H-pyrazol-3-yl)-2-(10-methyl-5,5-dioxo-5,10-dihydrophenothiazin-2-yl)-3-(tetrahydropyran-4-yl)propionamide.

C31H32N4O4S (556.69), LCMS (ESI): 557.4 (M+H$^+$).

Example 21

2-(10-Methyl-5,5-dioxo-5,10-dihydrophenothiazin-2-yl)-N-(4-oxo-4,5-dihydrothiazol-2-yl)-3-(tetrahydropyran-4-yl)propionamide

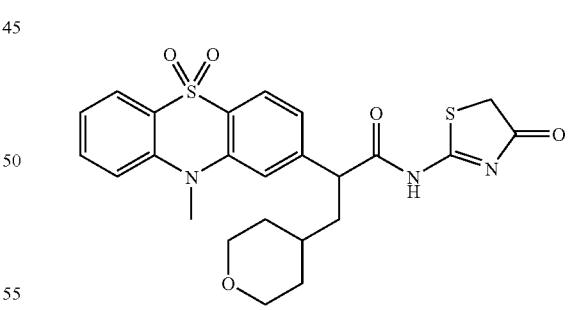

Analogously to Example 1, 2-(10-methyl-5,5-dioxo-5,10-dihydrophenothiazin-2-yl)-3-(tetrahydropyran-4-yl)propionic acid and commercially available pseudothiohydantoin give 2-(10-methyl-5,5-dioxo-5,10-dihydrophenothiazin-2-yl)-N-(4-oxo-4,5-dihydro-thiazol-2-yl)-3-(tetrahydropyran-4-yl)propionamide.

C24H25N3O5S2 (499.61), LCMS (ESI): 500.2 (M+H$^+$), 541.2 (M+MeCN+H$^+$).

Example 22

N-(4,5-Dihydrothiazol-2-yl)-2-(10-methyl-5,5-dioxo-5,10-dihydrophenothiazin-2-yl)-3-(tetrahydropyran-4-yl)propionamide

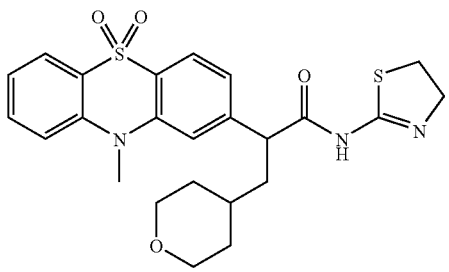

Analogously to Example 1, 2-(10-methyl-5,5-dioxo-5,10-dihydrophenothiazin-2-yl)-3-(tetrahydropyran-4-yl)propionic acid and commercially available 2-amino-2-thiazoline give N-(4,5-dihydrothiazol-2-yl)-2-(10-methyl-5,5-dioxo-5,10-dihydrophenothiazin-2-yl)-3-(tetrahydropyran-4-yl)propionamide.

C24H27N3O4S2 (485.62), LCMS (ESI): 486.2 (M+H$^+$).

Example 23

2-(10-Methyl-5,5-dioxo-5,10-dihydrophenothiazin-2-yl)-3-(tetrahydropyran-4-yl)-N-[1,3,4]thiadiazol-2-ylpropionamide

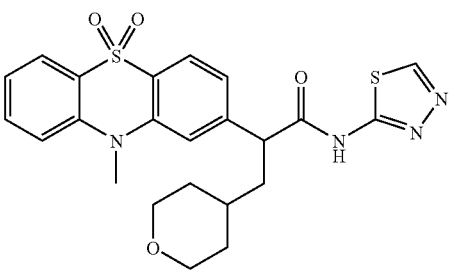

Analogously to Example 1, 2-(10-methyl-5,5-dioxo-5,10-dihydrophenothiazin-2-yl)-3-(tetrahydropyran-4-yl)propionic acid and commercially available 2-amino-1,3,4-thiadiazole give 2-(10-methyl-5,5-dioxo-5,10-dihydrophenothiazin-2-yl)-3-(tetrahydropyran-4-yl)-N-[1,3,4]thiadiazol-2-yl propionamide.

C23H24N4O4S2 (484.60), LCMS (ESI): 485.2 (M+H$^+$), 526.2 (M+MeCN+H$^+$).

Example 24

2-(10-Methyl-5,5-dioxo-5,10-dihydrophenothiazin-2-yl)-3-(tetrahydropyran-3-yl)-N-thiazol-2-ylpropionamide

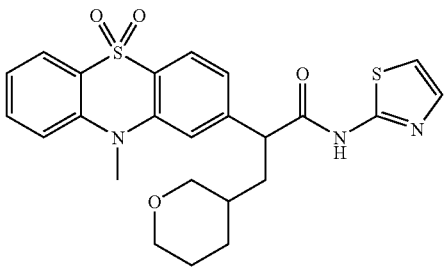

Analogously to Example 1, ethyl (10-methyl-5,5-dioxo-5,10-dihydrophenothiazin-2-yl)acetate, 3-iodomethyltetrahydropyran and commercially available 2-aminothiazole give 2-(10-methyl-5,5-dioxo-5,10-dihydrophenothiazin-2-yl)-3-(tetrahydropyran-3-yl)-N-thiazol-2-ylpropionamide.

C24H25N3O4S2 (483.61), LCMS (ESI): 484.1 (M+H$^+$).

Example 25

2-(10-Methyl-5,5-dioxo-5,10-dihydrophenothiazin-2-yl)-N-(1-methyl-1H-pyrazol-3-yl)-3-(tetrahydropyran-3-yl)propionamide

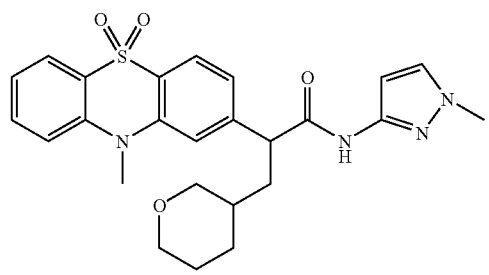

Analogously to Example 1, ethyl (10-methyl-5,5-dioxo-5,10-dihydrophenothiazin-2-yl)acetate, 3-iodomethyltetrahydropyran and commercially available 1-methyl-1H-pyrazol-3-amine give 2-(10-methyl-5,5-dioxo-5,10-dihydrophenothiazin-2-yl)-N-(1-methyl-1H-pyrazol-3-yl)-3-(tetrahydropyran-3-yl)propionamide.

C25H28N4O4S (480.59), LCMS (ESI): 481.2 (M+H$^+$).

Example 26

2-(10-Methyl-5,5-dioxo-5,10-dihydrophenothiazin-2-yl)-3-(3-methyloxetan-3-yl)-N-thiazol-2-ylpropionamide

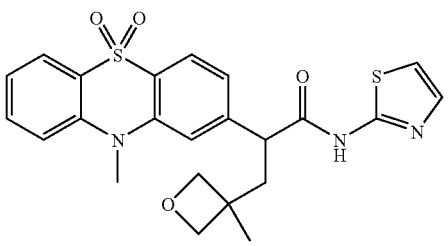

Analogously to Example 1, ethyl (10-methyl-5,5-dioxo-5,10-dihydrophenothiazin-2-yl)acetate, 3-iodomethyl-3-methyloxetane and commercially available 2-aminothiazole give 2-(10-methyl-5,5-dioxo-5,10-dihydrophenothiazin-2-yl)-3-(3-methyl-oxetan-3-yl)-N-thiazol-2-ylpropionamide.

C23H23N3O4S2 (469.59), LCMS (ESI): 470.10 (M+H$^+$).

Example 27

2-(10-Methyl-5,5-dioxo-5,10-dihydrophenothiazin-2-yl)-3-(3-methyloxetan-3-yl)-N-(1-methyl-1H-pyrazol-3-yl)propionamide

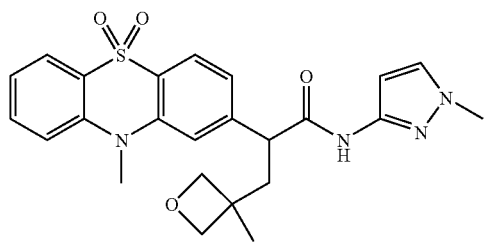

Analogously to Example 1, ethyl (10-methyl-5,5-dioxo-5,10-dihydrophenothiazin-2-yl)acetate, 3-iodomethyl-3-methyloxetane and commercially available 1-methyl-1H-pyrazol-3-amine give 2-(10-methyl-5,5-dioxo-5,10-dihydrophenothiazin-2-yl)-3-(3-methyloxetan-3-yl)-N-(1-methyl-1H-pyrazol-3-yl)propionamide.

C24H26N4O4S (466.56), LCMS (ESI): 467.2 (M+H$^+$).

Example 28

3-(3-Ethyloxetan-3-yl)-2-(10-methyl-5,5-dioxo-5,10-dihydrophenothiazin-2-yl)-N-thiazol-2-ylpropionamide

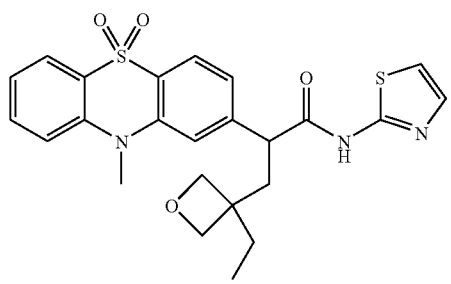

Analogously to Example 1, ethyl (10-methyl-5,5-dioxo-5,10-dihydrophenothiazin-2-yl)acetate, 3-ethyl-3-iodomethyloxetane and commercially available 2-aminothiazole give 3-(3-ethyloxetan-3-yl)-2-(10-methyl-5,5-dioxo-5,10-dihydrophenothiazin-2-yl)-N-thiazol-2-ylpropionamide.

C24H25N3O4S2 (483.61), LCMS (ESI): 484.1 (M+H$^+$).

Example 29

3-(3-Ethyloxetan-3-yl)-2-(10-methyl-5,5-dioxo-5,10-dihydrophenothiazin-2-yl)-N-(1-methyl-1H-pyrazol-3-yl)propionamide

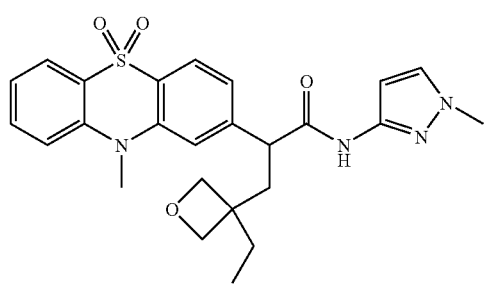

Analogously to Example 1, ethyl (10-methyl-5,5-dioxo-5,10-dihydrophenothiazin-2-yl)acetate, 3-ethyl-3-iodomethyloxetane and commercially available 1-methyl-1H-pyrazole-3-amine give 3-(3-ethyloxetan-3-yl)-2-(10-methyl-5,5-dioxo-5,10-dihydrophenothiazin-2-yl)-N-(1-methyl-1H-pyrazol-3-yl)propionamide.

C25H28N4O4S (480.59), LCMS (ESI): 481.2 (M+H$^+$).

Example 30

3-(4-Methylcyclohexyl)-2-(10-methyl-5,5-dioxo-5,10-dihydrophenothiazin-2-yl)-N-thiazol-2-ylpropionamide

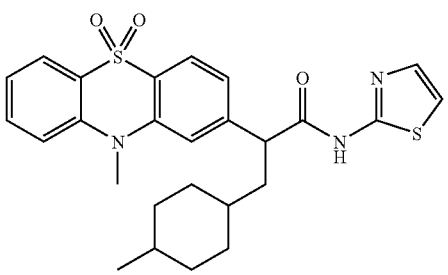

Analogously to Example 1, ethyl (10-methyl-5,5-dioxo-5,10-dihydrophenothiazin-2-yl)acetate, 1-iodomethyl-4-methylcyclohexane and commercially available 2-amino-thiazole give 3-(4-methylcyclohexyl)-2-(10-methyl-5,5-dioxo-5,10-dihydrophenothiazin-2-yl)-N-thiazol-2-ylpropionamide.

C26H29N3O3S2 (495.67), LCMS (ESI): 496.2 (M+H$^+$), 537.2 (M+MeCN+H$^+$).

Example 31

3-(4-Methylcyclohexyl)-2-(10-methyl-5,5-ioxo-5,10-dihydrophenothiazin-2-yl)-N-(1-methyl-1H-pyrazol-3-yl)propionamide

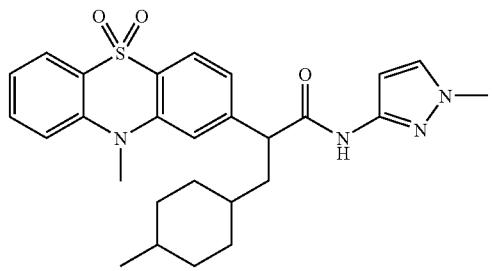

Analogously to Example 1, ethyl (10-methyl-5,5-dioxo-5,10-dihydrophenothiazin-2-yl)acetate, 1-iodomethyl-4-methylcyclohexane and commercially available 1-methyl-1H-pyrazole-3-amine give 3-(4-methylcyclohexyl)-2-(10-methyl-5,5-dioxo-5,10-dihydrophenothiazin-2-yl)-N-(1-methyl-1H-pyrazol-3-yl)propionamide.

C27H32N4O3S (492.65), LCMS (ESI): 493.2 (M+H$^+$).

Example 32

3-Indan-2-yl-2-(10-methyl-5,5-dioxo-5,10-dihydrophenothiazin-2-yl)-N-(1-methyl-1H-pyrazol-3-yl)propionamide

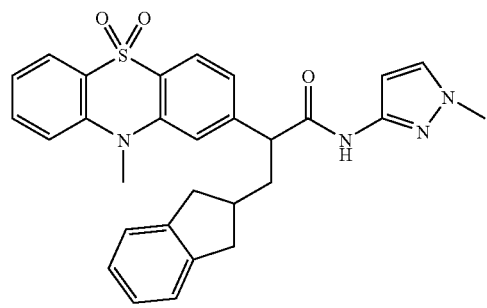

Analogously to Example 1, ethyl (10-methyl-5,5-dioxo-5,10-dihydrophenothiazin-2-yl)acetate, 2-iodomethylindane and commercially available 1-methyl-1H-pyrazole-3-amine give 3-indan-2-yl-2-(10-methyl-5,5-dioxo-5,10-dihydrophenothiazin-2-yl)-N-(1-methyl-1H-pyrazol-3-yl)propionamide.

C29H28N4O3S (512.63), LCMS (ESI): 513.2 (M+H$^+$).

Example 33

3-Indan-2-yl-N-(5-methoxythiazolo[5,4-b]pyridin-2-yl)-2-(10-methyl-5,5-dioxo-5,10-dihydrophenothiazin-2-yl)propionamide

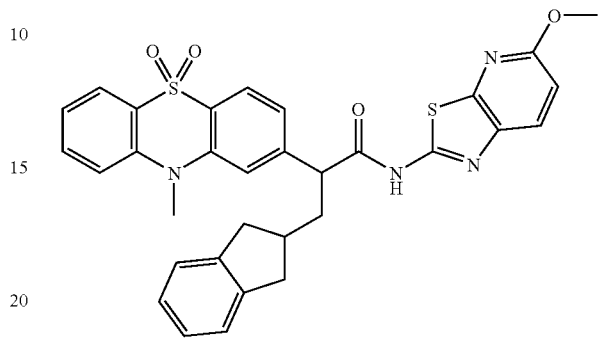

Analogously to Example 1, ethyl (10-methyl-5,5-dioxo-5,10-dihydrophenothiazin-2-yl)acetate, 2-iodomethylindane and 5-methoxythiazolo[5,4-b]pyridin-2-ylamine give 3-indan-2-yl-N-(5-methoxythiazolo[5,4-b]pyridin-2-yl)-2-(10-methyl-5,5-dioxo-5,10-dihydrophenothiazin-2-yl)propionamide.

C32H28N4O4S2 (596.73), LCMS (ESI): 597.3 (M+H$^+$).

Example 34

2-(10-Methyl-5,5-dioxo-5,10-dihydrophenothiazin-2-yl)-3-(1-methylpiperidin-3-yl)-N-thiazol-2-ylpropionamide 3-Iodomethyl-1-methylpiperidine

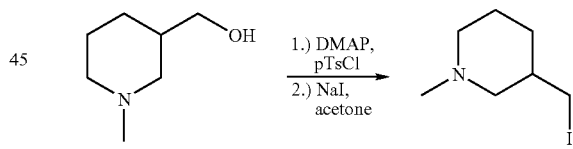

10.0 g of 1-methyl-3-piperidinemethanol are dissolved in 100 ml of dichloromethane, and 9.46 g of 4-dimethylaminopyridine and 15.5 g of p-toluenesulfonyl chloride are added with ice cooling The reaction solution is stirred at room temperature for twelve hours and then washed with saturated NaHCO$_3$ solution and dried over MgSO$_4$, and the solvent is removed under reduced pressure. The resulting residue is dissolved in 150 ml of acetone, and 39.5 g of sodium iodide are added. The reaction mixture is heated at the boil under reflux for two hours. The solvent is then removed under reduced pressure, and the residue is taken up in 300 ml of ethyl acetate and washed twice with in each case 100 ml of water. The organic phase is dried over MgSO$_4$ and then concentrated under reduced pressure. This gives 9.4 g of 3-iodomethyl-1-methylpiperidine.

C7H14IN (239.10), LCMS (ESI): 240.0 (M+H$^+$).

2-(10-Methyl-5,5-dioxo-5,10-dihydrophenothiazin-2-yl)-3-(1-methylpiperidin-3-yl)-N-thiazol-2-ylpropionamide

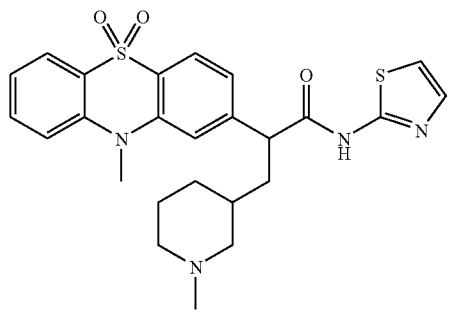

Analogously to Example 1, ethyl (10-methyl-5,5-dioxo-5,10-dihydrophenothiazin-2-yl)acetate, 3-iodomethyl-1-methylpiperidine and commercially available 2-amino-thiazole give 2-(10-methyl-5,5-dioxo-5,10-dihydrophenothiazin-2-yl)-3-(1-methylpiperidin-3-yl)-N-thiazol-2-ylpropionamide. C25H28N4O3S2 (496.65), LCMS (ESI): 497.2 (M+H+).

Example 35

2-(10-Methyl-5,5-dioxo-5,10-dihydrophenothiazin-2-yl)-3-(1-methylpiperidin-3-yl)-N-(1-methyl-1H-pyrazol-3-yl)propionamide

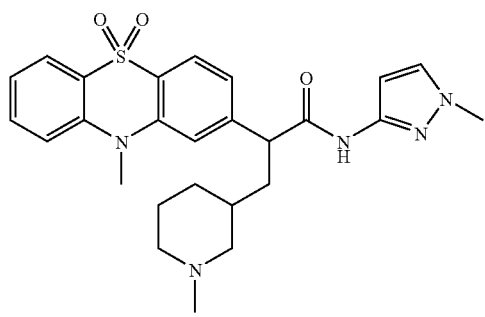

Analogously to Example 1, ethyl (10-methyl-5,5-dioxo-5,10-dihydrophenothiazin-2-yl)acetate, 3-iodomethyl-1-methylpiperidine and commercially available 1-methyl-1H-pyrazole-3-amine give 2-(10-methyl-5,5-dioxo-5,10-dihydrophenothiazin-2-yl)-3-(1-methylpiperidin-3-yl)-N-(1-methyl-1H-pyrazol-3-yl)propionamide.

C26H31N5O3S (493.63), LCMS (ESI): 494.2 (M+H+).

Example 36

2-(10-Methyl-5,5-dioxo-5,10-dihydrophenothiazin-2-yl)-N-(1-methyl-1H-pyrazol-3-yl)-3-(4-oxocyclohexyl)propionamide

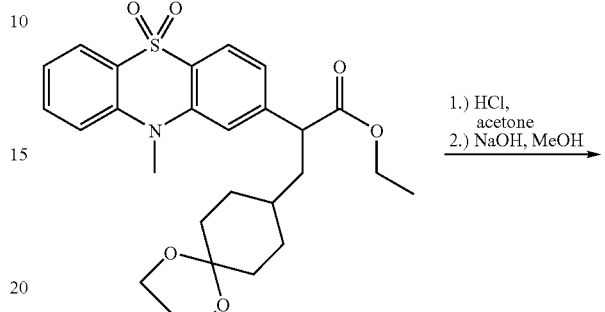

1.) HCl, acetone
2.) NaOH, MeOH

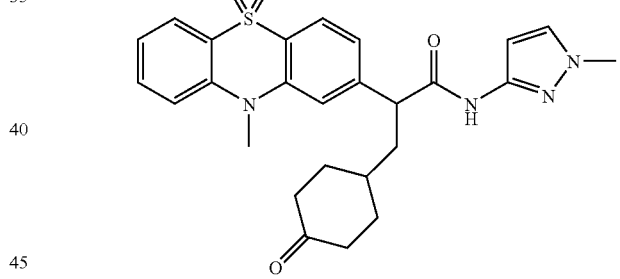

TOTU, Hünig's base

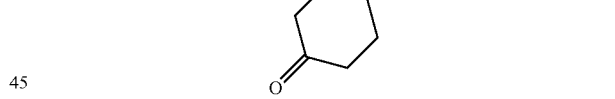

2-(10-Methyl-5,5-dioxo-5,10-dihydrophenothiazin-2-yl)-3-(4-oxocyclohexyl)propionic Acid

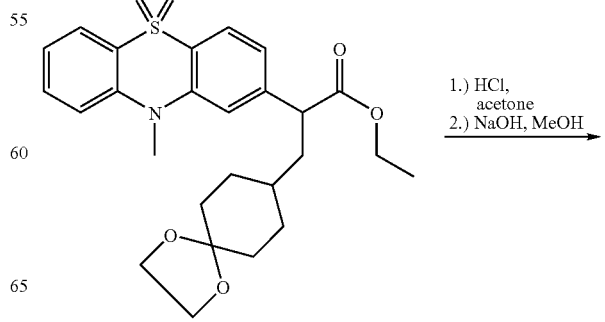

1.) HCl, acetone
2.) NaOH, MeOH

-continued

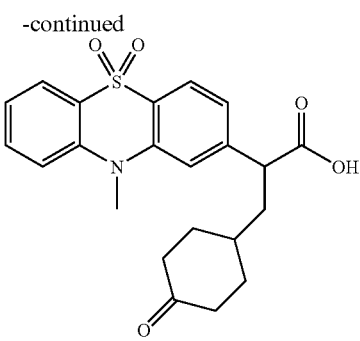

1.1 g of ethyl 3-(1,4-dioxaspiro[4.5]dec-8-yl)-2-(10-methyl-5,5-dioxo-5,10-dihydrophenothiazin-2-yl)propionate (prepared analogously to Example 1 from ethyl (10-methyl-5,5-dioxo-5,10-dihydrophenothiazin-2-yl)acetate and 8-iodomethyl-1,4-dioxaspiro[4.5]decane) are dissolved in 20 ml of acetone, and 4 ml of 10% strength hydrochloric acid are added. The reaction mixture is stirred at room temperature for three hours. The reaction mixture is then washed with saturated NaHCO$_3$ solution, dried over MgSO$_4$ and then concentrated under reduced pressure. The residue is dissolved in 20 ml of methanol, 7.9 ml of 2 M aqueous sodium hydroxide solution are added and the mixture is heated at the boil under reflux for one hour. The cooled reaction mixture is diluted by addition of 200 ml of ethyl acetate and acidified with 2 N HCl. The organic phase is then washed twice with in each case 80 ml of water and of saturated sodium chloride solution, dried over MgSO$_4$ and then concentrated under reduced pressure. This gives 600 mg of 2-(10-methyl-5,5-dioxo-5,10-dihydrophenothiazin-2-yl)-3-(4-oxo-cyclohexyl)propionic acid. C22H23NO5S (413.50), LCMS (ESI): 414.1 (M+H$^+$). 2-(10-Methyl-5,5-dioxo-5,10-dihydrophenothiazin-2-yl)-N-(1-methyl-1H-pyrazol-3-yl)-3-(4-oxocyclohexyl)propionamide

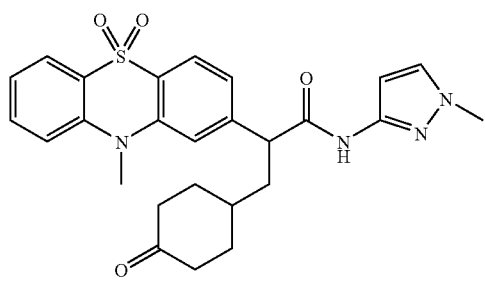

Analogously to Example 1, 2-(10-methyl-5,5-dioxo-5,10-dihydrophenothiazin-2-yl)-3-(4-oxocyclohexyl)propionic acid and commercially available 1-methyl-1H-pyrazole-3-amine give 2-(10-methyl-5,5-dioxo-5,10-dihydrophenothiazin-2-yl)-N-(1-methyl-1H-pyrazol-3-yl)-3-(4-oxocyclohexyl)propionamide.

C26H28N4O4S (492.60), LCMS (ESI): 493.2 (M+H$^+$).

The racemic mixture is separated into the enantiomers on a chiral phase (S,S-Whelk 51) using the mobile phase n-heptane:methanol:ethanol=4:1:1+0.1% diethylamine (Rt=10.68 min and Rt=12.54 min).

Example 37

3-(4-Hydroxycyclohexyl)-2-(10-methyl-5,5-dioxo-5,10-dihydrophenothiazin-2-yl)-N-(1-methyl-1H-pyrazol-3-yl)propionamide

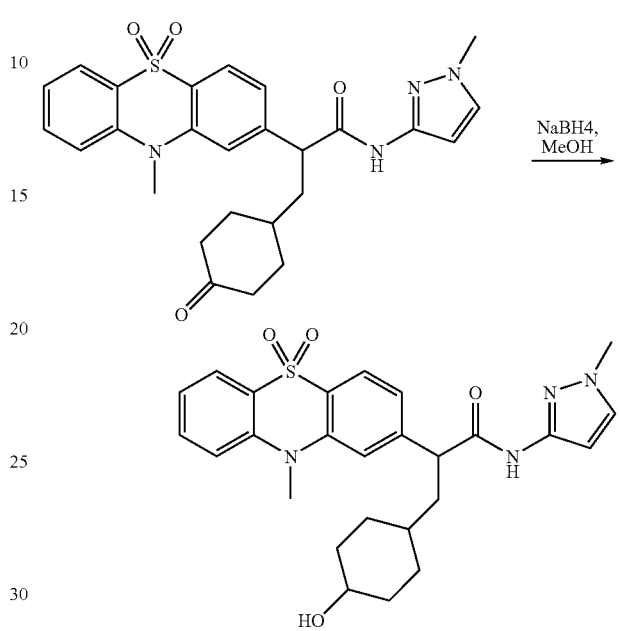

50 mg of 2-(10-methyl-5,5-dioxo-5,10-dihydrophenothiazin-2-yl)-N-(1-methyl-1H-pyrazol-3-yl)-3-(4-oxocyclohexyl)propionamide are suspended in 20 ml of methanol, and 3.8 mg of sodium borohydride are added at room temperature. The mixture is stirred at room temperature for another hour. During the duration of the reaction, a clear solution slowly forms. The methanol is removed under reduced pressure, and the residue is extracted with ethyl acetate and water. The organic phase is washed twice with water and then dried over MgSO$_4$ and concentrated under reduced pressure. The residue is lyophilized. This gives 42 mg of 3-(4-hydroxycyclohexyl)-2-(10-methyl-5,5-dioxo-5,10-dihydrophenothiazin-2-yl)-N-(1-methyl-1H-pyrazol-3-yl)propionamide as a white amorphous solid.

C26H30N4O4S (494.62), LCMS (ESI): 495.3 (M+H$^+$).

Example 38

3-(4-Hydroxyiminocyclohexyl)-2-(10-methyl-5,5-dioxo-5,10-dihydrophenothiazin-2-yl)-N-(1-methyl-1H-pyrazol-3-yl)propionamide

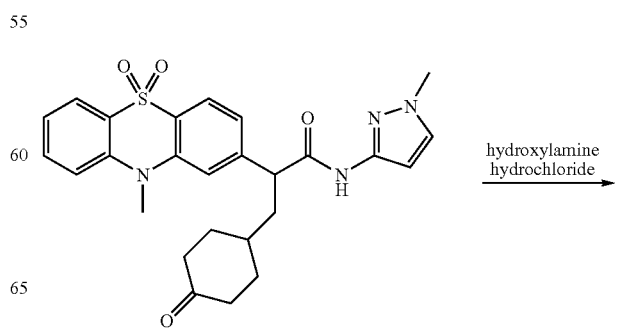

83

-continued

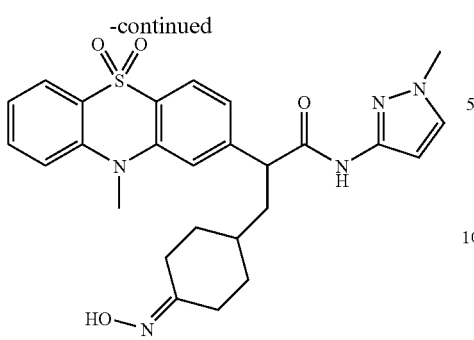

67 mg of 2-(10-methyl-5,5-dioxo-5,10-dihydrophenothiazin-2-yl)-N-(1-methyl-1H-pyrazol-3-yl)-3-(4-oxocyclohexyl)propionamide and 14 mg of hydroxylamine hydrochloride are dissolved in 13 ml of methanol and heated at the boil under reflux for three hours. The methanol is then removed under reduced pressure, and the resulting residue is taken up in a mixture of 20 ml of ethyl acetate and 10 ml of water. The organic phase is washed twice with in each case 10 ml of water, dried over $MgSO_4$, concentrated under reduced pressure and then lyophilized. This gives 49 mg of 3-(4-hydroxyiminocyclohexyl)-2-(10-methyl-5,5-dioxo-5,10-dihydrophenothiazin-2-yl)-N-(1-methyl-1H-pyrazol-3-yl)propionamide.

$C_{26}H_{29}N_5O_4S$ (507.62), LCMS (ESI): 508.2 $(M+H^+)$.

Example 39

3-(1,1-Dioxotetrahydrothiophen-3-yl)-N-(5-methoxythiazolo[5,4-b]pyridin-2-yl)-2-(10-methyl-5,5-dioxo-5,10-dihydrophenothiazin-2-yl)propionamide 3-Iodomethyltetrahydrothiophene 1,1-dioxide

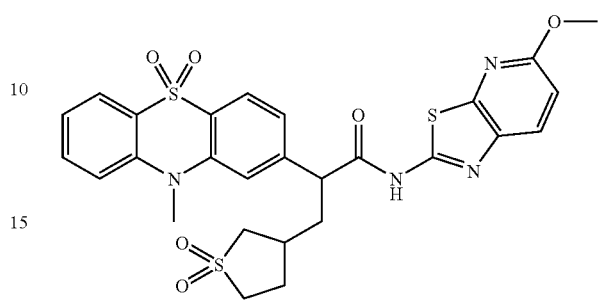

1.0 g of (1,1-dioxotetrahydrothiophen-3-yl)methanol are dissolved in 30 ml of dichloromethane, and 902 mg of 4-dimethylaminopyridine and 1.33 g of p-toluenesulfonyl chloride are added with ice cooling. The reaction solution is stirred at room temperature for twelve hours and then washed with saturated $NaHCO_3$ solution and dried over $MgSO_4$, and the solvent is removed under reduced pressure. Rf of the intermediate (tosylate) in n-heptane:ethyl acetate=1:1:Rf (tosylate)=0.18. The resulting residue is dissolved in 30 ml of acetone, and 3.5 g of sodium iodide are added. The reaction mixture is heated at the boil under reflux for six hours. The solvent is then removed under reduced pressure and the residue is taken up in 150 ml of ethyl acetate and washed twice with in each case 50 ml of water. The organic phase is dried over $MgSO_4$ and then concentrated under reduced pressure. This gives 1.44 g of 3-iodomethyltetrahydrothiophene 1,1-dioxide. $C_5H_9IO_2S$ (260.09), LCMS (ESI): 260.9 $(M+H^+)$, Rf (n-heptane:ethyl acetate=4:1)=0.33.

84

3-(1,1-Dioxotetrahydrothiophen-3-yl)-N-(5-methoxythiazolo[5,4-b]pyridin-2-yl)-2-(10-methyl-5,5-dioxo-5,10-dihydrophenothiazin-2-yl)propionamide

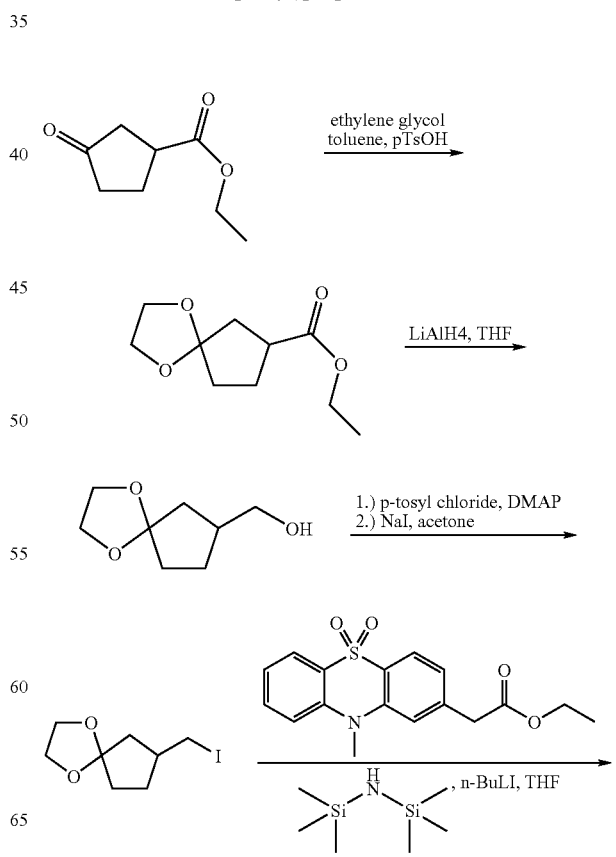

Analogously to Example 1, ethyl (10-methyl-5,5-dioxo-5,10-dihydrophenothiazin-2-yl)acetate, 3-iodomethyltetrahydrothiophene 1,1-dioxide and 5-methoxy-thiazolo[5,4-b]pyridin-2-ylamine give 3-(1,1-dioxotetrahydrothiophen-3-yl)-N-(5-methoxy-thiazolo[5,4-b]pyridin-2-yl)-2-(10-methyl-5,5-dioxo-5,10-dihydrophenothiazin-2-yl)propionamide.

$C_{27}H_{26}N_4O_6S_3$ (598.72), LCMS (ESI): 599.1 $(M+H^+)$.

Example 40

2-(10-Methyl-5,5-dioxo-5,10-dihydrophenothiazin-2-yl)-N-(1-methyl-1H-pyrazol-3-yl)-3-(3-oxocyclopentyl)propionamid -continued

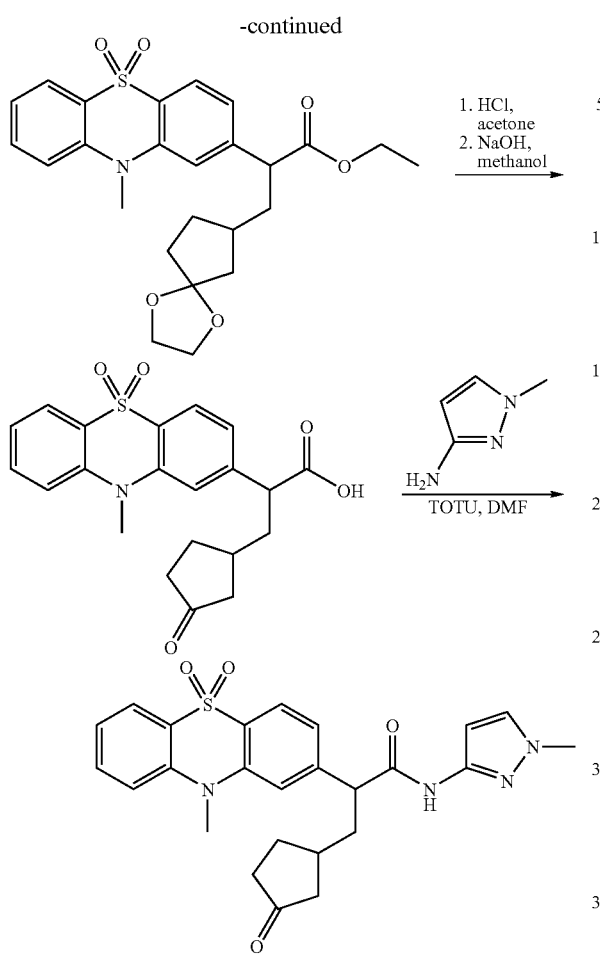

of n-heptane to n-heptane:ethyl acetate=7:10. This gives 8.65 g of ethyl 1,4-dioxaspiro[4.4]nonane-7-carboxylate as an oil.

C10H16O4 (200.24), Rf (n-heptane:ethyl acetate=2:1)=0.38.

(1,4-Dioxaspiro[4.4]non-7-yl)methanol

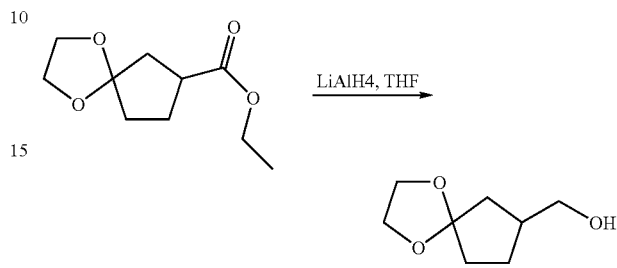

1.22 g of lithium aluminum hydride are initially charged in 200 ml of dry tetrahydrofuran and cooled to −20° C. At this temperature, 8.65 g of ethyl 1,4-dioxa-spiro[4.4]nonane-7-carboxylate dissolved in 50 ml of tetrahydrofuran are added dropwise under argon. After one hour, the cooling bath is removed and the reaction mixture is stirred for another three hours. The reaction mixture is quenched by addition of 10 ml of water and stirred at room temperature for two hours. The reaction mixture is filtered and the filtrate is concentrated under reduced pressure. This gives 6.7 g of (1,4-dioxaspiro[4.4]non-7-yl)methanol as an oil.

C8H14O3 (158.20), Rf (n-heptane:ethyl acetate=2:1)=0.09.

7-Iodomethyl-1,4-dioxaspiro[4.4]nonane

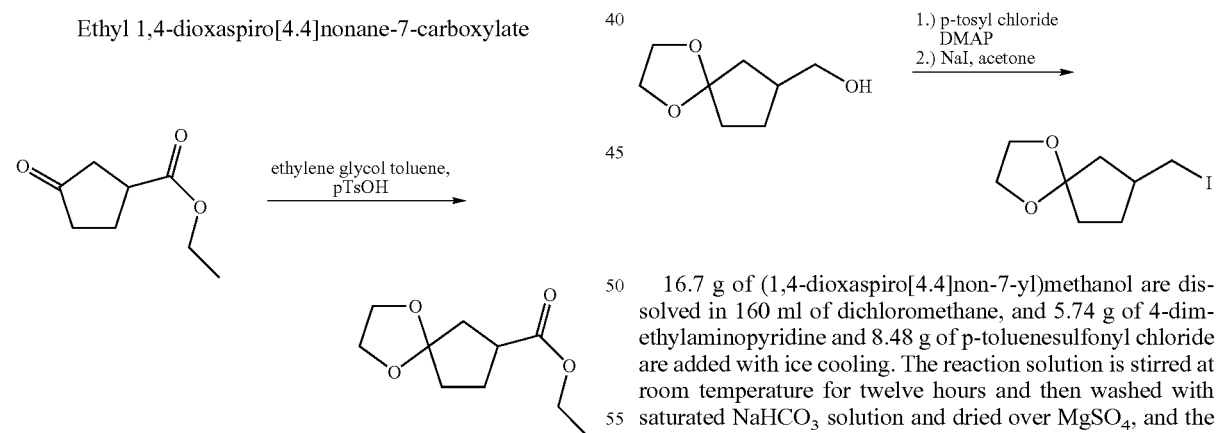

Ethyl 1,4-dioxaspiro[4.4]nonane-7-carboxylate

A solution of 9.9 g of ethyl 3-oxocyclopentanecarboxylate, 600 mg of p-toluenesulfonic acid monohydrate and 3.5 ml of ethylene glycol in 100 ml of toluene is heated at the boil under reflux in a water separator for four hours. The solvent is removed under reduced pressure and the residue is taken up in 250 ml of ethyl acetate and washed with 150 ml of water. The organic phase is dried over MgSO4 and concentrated under reduced pressure. The residue is purified on silica gel using the mobile phase n-heptane:ethyl acetate as a linear gradient 16.7 g of (1,4-dioxaspiro[4.4]non-7-yl)methanol are dissolved in 160 ml of dichloromethane, and 5.74 g of 4-dimethylaminopyridine and 8.48 g of p-toluenesulfonyl chloride are added with ice cooling. The reaction solution is stirred at room temperature for twelve hours and then washed with saturated NaHCO3 solution and dried over MgSO4, and the solvent is removed under reduced pressure. Rf of the intermediate (tosylate) in n-heptane:ethyl acetate=4:1:Rf (tosylate)=0.09. The resulting residue is dissolved in 160 ml of acetone, and 21.58 g of sodium iodide are added. The reaction mixture is heated at the boil under reflux for six hours. The solvent is then removed under reduced pressure and the residue is taken up in 150 ml of ethyl acetate and washed twice with in each case 50 ml of water. The organic phase is dried over MgSO4 and then concentrated under reduced pressure. This gives 9.1 g of 7-iodomethyl-1,4-dioxaspiro[4.4]nonane. C8H13IO2 (268.10), LCMS (ESI): 269.1 (M+H+), Rf (n-heptane:ethyl acetate=4:1)=0.34.

2-(10-Methyl-5,5-dioxo-5,10-dihydrophenothiazin-2-yl)-N-(1 methyl-1H-pyrazol-3-yl)-3-(3-oxocyclopentyl)propionamide

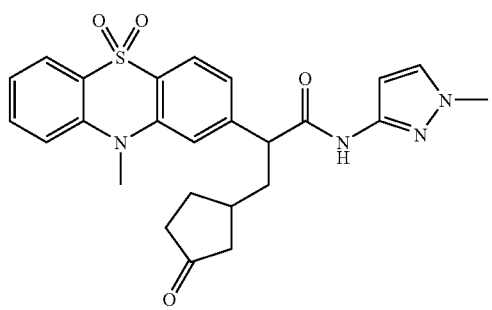

Analogously to Example 1 and Example 36, ethyl (10-methyl-5,5-dioxo-5,10-dihydrophenothiazin-2-yl)acetate, 7-iodomethyl-1,4-dioxaspiro[4.4]nonane and commercially available 1-methyl-1H-pyrazole-3-amine give 2-(10-methyl-5,5-dioxo-5,10-dihydrophenothiazin-2-yl)-N-(1-methyl-1H-pyrazol-3-yl)-3-(3-oxo-cyclopentyl)propionamide.

C25H26N4O4S (478.57), LCMS (ESI): 479.2 (M+H$^+$).

The racemic diastereomer mixture is separated into the isomers on a chiral phase (IA-103) using the mobile phase methanol:ethanol=1:1 (Rt=8.276 min, Rt=9.897 min, Rt=10.539 min and Rt=12.117 min).

Example 41

N-(5-Methoxythiazolo[5,4-b]pyridin-2-yl)-2-(10-methyl-5,5-dioxo-5,10-dihydrophenothiazin-2-yl)-3-((R)-3-oxocyclopentyl)propionamide

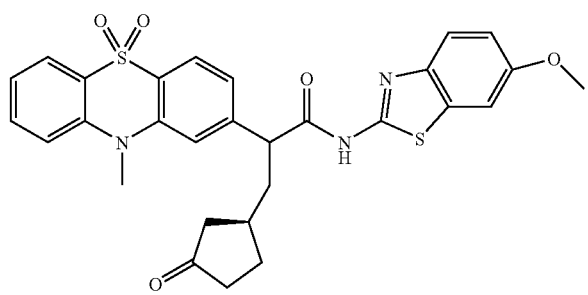

Analogously to Example 1 and Example 36, ethyl (10-methyl-5,5-dioxo-5,10-dihydrophenothiazin-2-yl)acetate, (S)-7-iodomethyl-1,4-d ioxaspiro[4.4]nonane (prepared analogously to Example 40 from commercially available methyl (S)-3-oxo-cyclopentanecarboxylate) and 5-methoxy-thiazolo[5,4-b]pyridin-2-ylamine give N-(5-methoxythiazolo[5,4-b]pyridin-2-yl)-2-(10-methyl-5,5-dioxo-5,10-dihydrophenothiazin-2-yl)-3-((R)-3-oxocyclopentyl)propionamide.

C28H26N4O5S2 (562.67), LCMS (ESI): 563.1 (M+H$^+$).

Example 42

Ethyl 10-methyl-8-[1-(1-methyl-1H-pyrazol-3-ylcarbamoyl)-2-(3-oxocyclopentyl)-ethyl]-5,5-dioxo-5,10-dihydrophenothiazine-3-carboxylate

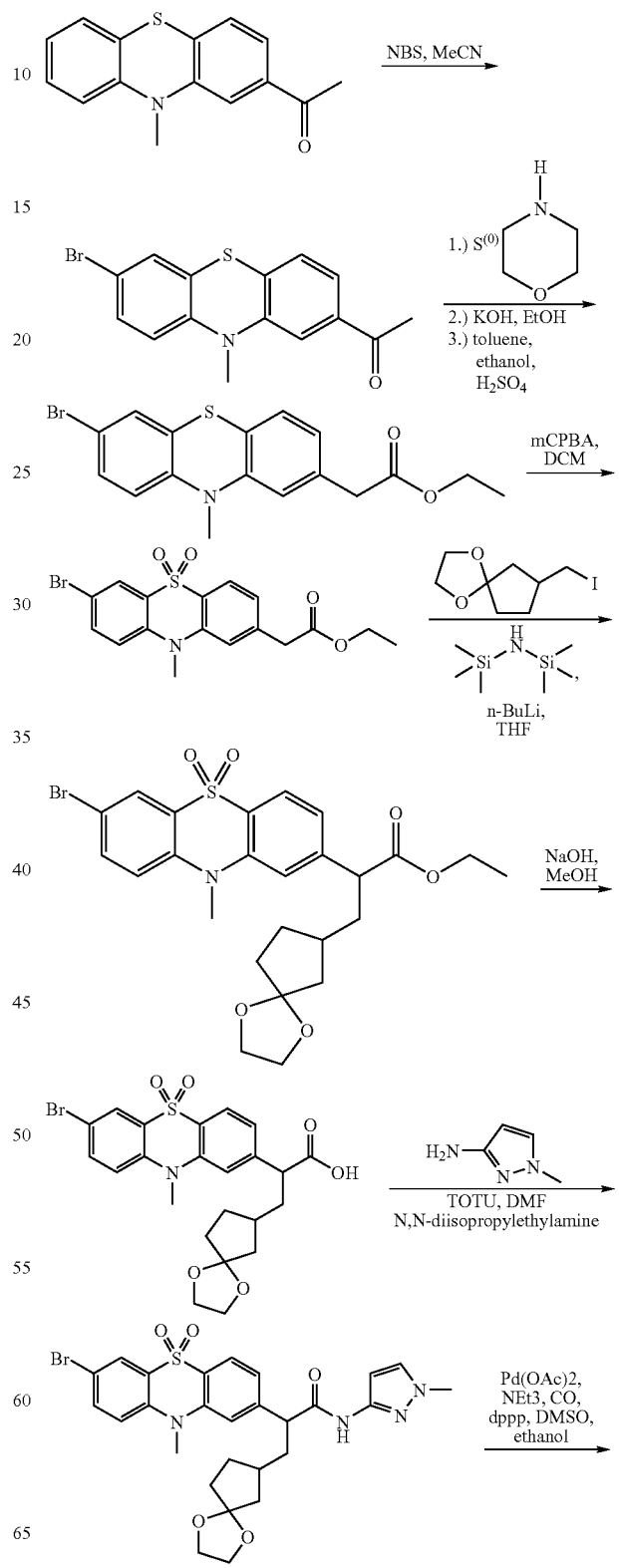

90

Ethyl 10-methyl-8-[1-(1-methyl-1H-pyrazol-3-ylcarbamoyl)-2-(3-oxocyclopentyl)ethyl]-5,5-dioxo-5,10-dihydrophenothiazin-3-carboxylate

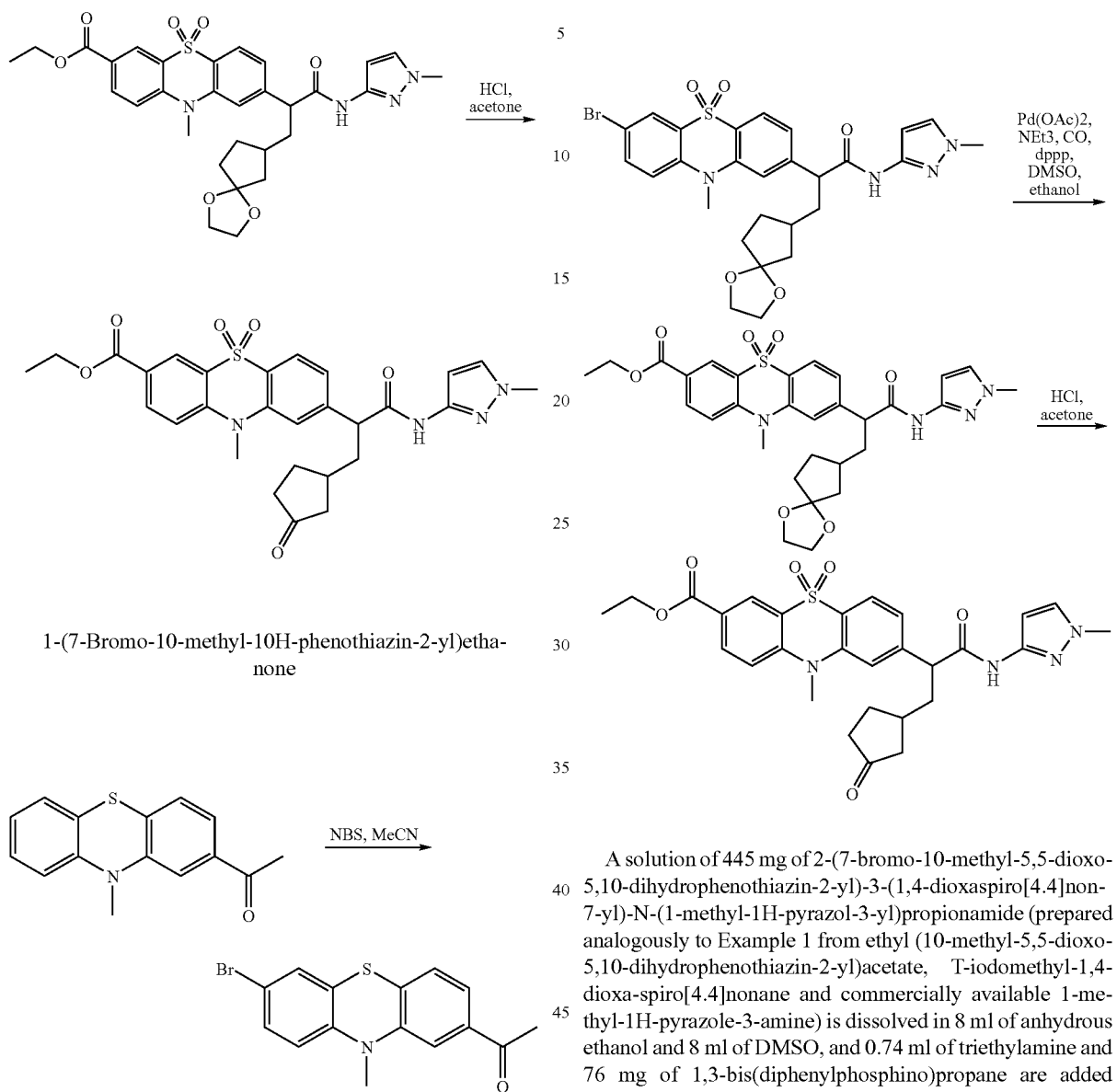

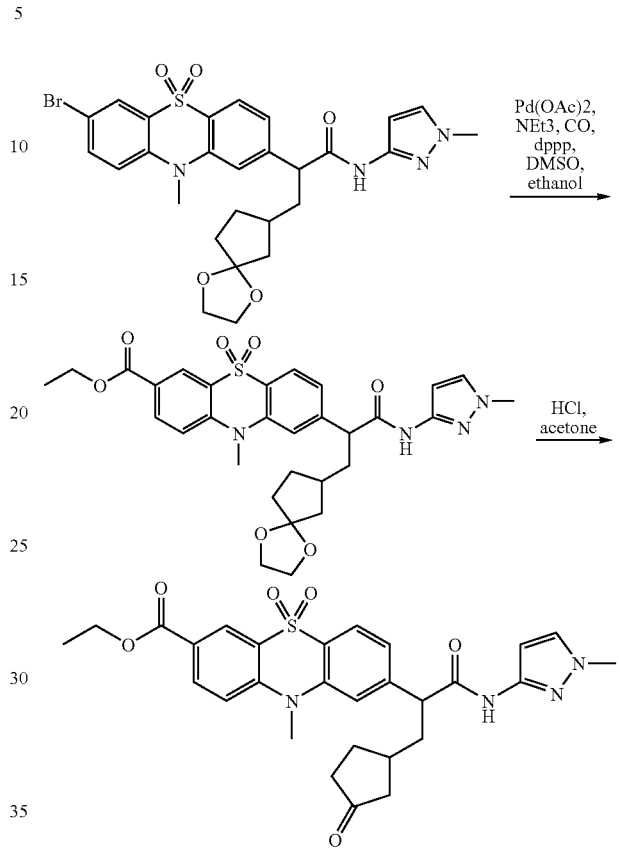

1-(7-Bromo-10-methyl-10H-phenothiazin-2-yl)ethanone 9.93 g of 1-(10-methyl-10H-phenothiazin-2-yl)ethanone are dissolved in 300 ml of acetonitrile, and 8.31 g of N-bromosuccinimide are added. The color of the reaction mixture changes to black.

The reaction mixture is diluted by addition of 500 ml of ethyl acetate, washed three times with in each case 200 ml of saturated sodium thiosulfate solution and saturated NaHCO$_3$ solution and dried over MgSO$_4$, and the solvents are then removed under reduced pressure. The resulting residue is purified on silica gel using the mobile phase n-heptane=>n-heptane:ethyl acetate=>ethyl acetate as a linear gradient. This gives 10.8 g of 1-(7-bromo-10-methyl-10H-phenothiazin-2-yl)ethanone as a yellow solid.

C15H12BrNOS (334.24), LCMS (ESI): 333.95, 334.95, 335.95 (M+H$^+$), Rf (n-heptane:ethyl acetate=4:1)=0.21.

A solution of 445 mg of 2-(7-bromo-10-methyl-5,5-dioxo-5,10-dihydrophenothiazin-2-yl)-3-(1,4-dioxaspiro[4.4]non-7-yl)-N-(1-methyl-1H-pyrazol-3-yl)propionamide (prepared analogously to Example 1 from ethyl (10-methyl-5,5-dioxo-5,10-dihydrophenothiazin-2-yl)acetate, 7-iodomethyl-1,4-dioxa-spiro[4.4]nonane and commercially available 1-methyl-1H-pyrazole-3-amine) is dissolved in 8 ml of anhydrous ethanol and 8 ml of DMSO, and 0.74 ml of triethylamine and 76 mg of 1,3-bis(diphenylphosphino)propane are added under argon. The reaction solution is flushed with argon, and 35 mg of palladium acetate are then added. The reaction mixture is stirred at 70° C. and 1 bar of CO for three hours. The cooled reaction mixture is diluted by addition of 200 ml of ethyl acetate and washed with in each case 100 ml of water and saturated sodium chloride solution, dried over MgSO$_4$ and then concentrated under reduced pressure. The residue is dissolved in 25 ml of acetone, and 3 ml of 10% strength hydrochloric acid are added. The reaction mixture is stirred at room temperature for three hours. The reaction mixture is then washed with saturated NaHCO$_3$ solution, dried over MgSO$_4$ and then concentrated under reduced pressure. The residue is purified on silica gel using the mobile phase n-heptane:ethyl acetate=1:1=>ethyl acetate=>ethyl acetate:methanol=99:1. This gives 844 mg of ethyl 10-methyl-8-[1-(1-methyl-1H-pyrazol-3-ylcarbamoyl)-2-(3-oxocyclopentyl)-ethyl]-5,5-dioxo-5,10-dihydrophenothiazine-3-carboxylate.

C28H30N4O6S (550.64), LCMS (ESI): 551.2.

Example 43

10-Methyl-8-[1-(1-methyl-1H-pyrazol-3-ylcarbamoyl)-2-(3-oxo-cyclopentyl)-ethyl]-5,5-dioxo-5,10-dihydrophenothiazin-3-carboxylic acid

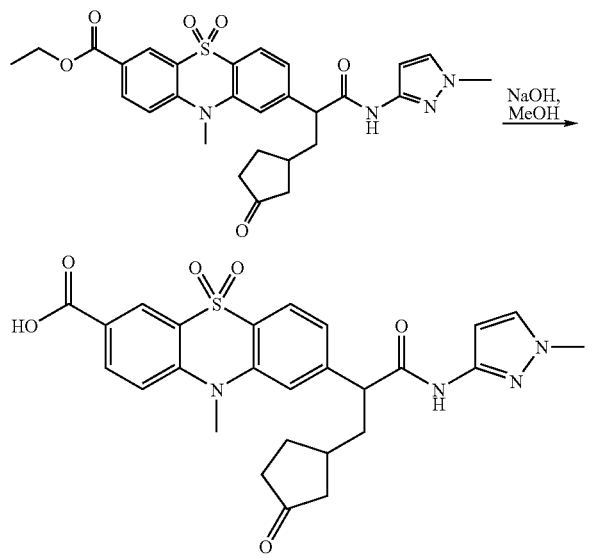

260 mg of ethyl 10-methyl-8-[1-(1-methyl-1H-pyrazol-3-ylcarbamoyl)-2-(3-oxocyclopentyl)ethyl]-5,5-dioxo-5,10-dihydrophenothiazine-3-carboxylate are suspended in 10 ml of methanol, and 1.64 ml of a 2 M NaOH solution are added. The reaction mixture is heated at the boil under reflux for one hour. The methanol is removed under reduced pressure and the reaction mixture is adjusted to pH 4 by addition of concentrated hydrochloric acid. The mixture is extracted three times with in each case 100 ml of ethyl acetate. The combined organic phases are dried over $MgSO_4$ and then concentrated under reduced pressure. This gives 155 mg of 10-methyl-8-[1-(1-methyl-1H-pyrazol-3-ylcarbamoyl)-2-(3-oxocyclopentyl)ethyl]-5,5-dioxo-5,10-dihydrophenothiazine-3-carboxylic acid.

C26H26N4O6S (522.58), LCMS (ESI): 523.20 (M+H$^+$).

Example 44

2-(5,5-Dioxo-5,10-dihydrophenothiazin-2-yl)-N-(1-methyl-1H-pyrazol-3-yl)-3-(tetrahydropyran-4-yl)propionamide

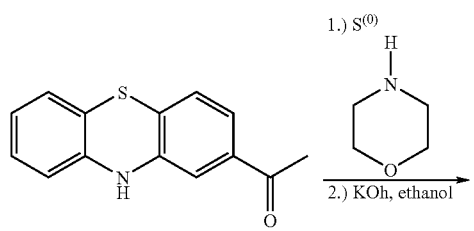

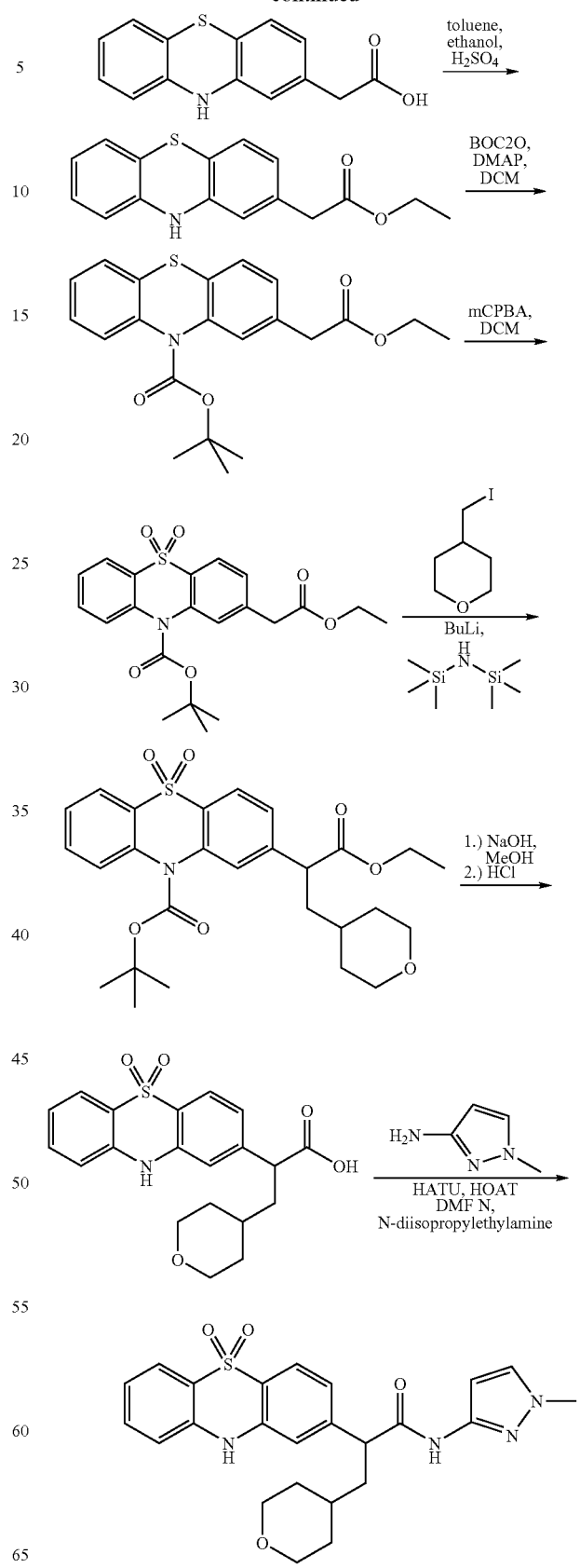

tert-Butyl 2-ethoxycarbonylmethyl-5,5-dioxo-5H-phenothiazine-10-carboxylate

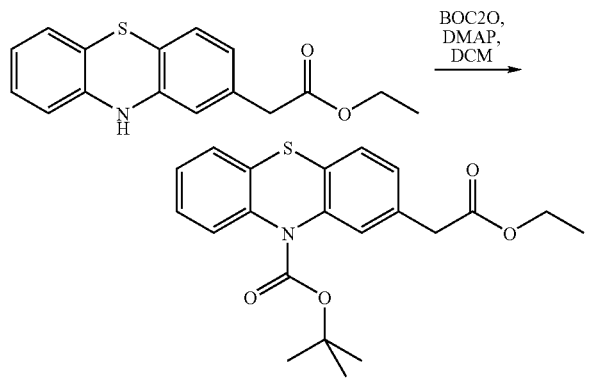

18.5 g of ethyl (10H-phenothiazin-2-yl)acetate (prepared analogously to Example 1 from 2-acetylphenothiazine) are dissolved in 300 ml of acetonitrile, and 21.2 g of di-tert-butyl dicarbonate and 1.58 g of 4-dimethylaminopyridine are added. The reaction mixture is heated at the boil under reflux for three hours. The cooled reaction mixture is diluted by addition of 500 ml of ethyl acetate and washed three times with in each case 200 ml of 0.5% strength citric acid solution. The organic phase is dried over $MgSO_4$ and then concentrated under reduced pressure. This gives 25.0 g of tert-butyl 2-ethoxycarbonylmethyl-5,5-dioxo-5H-phenothiazine-10-carboxylate as a colorless amorphous foam.

C21H23NO4S (385.49), LCMS (ESI): 330.1 (M-tert butyl+H$^+$), Rf (n-heptane:ethyl acetate=3:1)=0.49.

tert-Butyl 2-ethoxycarbonylmethyl-5,5-dioxo-5H-phenothiazine-10-carboxylate

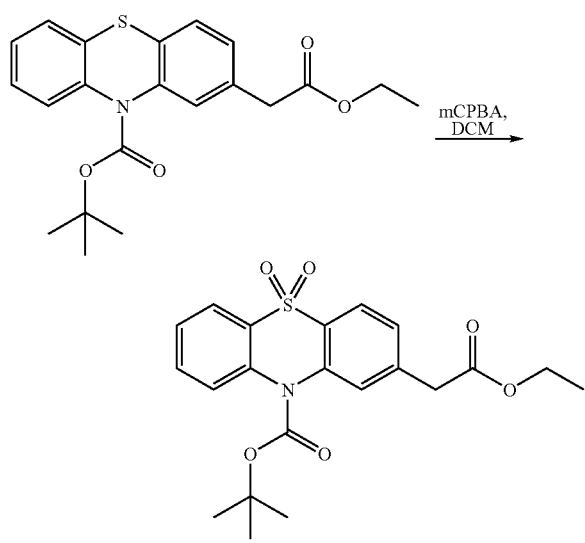

25.0 g of tert-butyl 2-ethoxycarbonylmethyl-5,5-dioxo-5H-phenothiazine-10-carboxylate are dissolved in 500 ml of dichloromethane, and 50.4 g of mCPBA are added a little at a time. The reaction mixture is stirred at room temperature for one hour. The reaction mixture is then washed with 200 ml of saturated $NaHCO_3$ solution, 5× with in each case 200 ml of 2 M NaOH and once with 100 ml of saturated NaCl solution and dried over $MgSO_4$, and the solvent is then removed under reduced pressure. This gives 14.4 g of tert-butyl 2-ethoxycarbonylmethyl-5,5-dioxo-5H-phenothiazine-10-carboxylate as an amorphous colorless foam.

C21H23NO6S (417.48), LCMS (ESI): 435.1 (M+NH4$^+$), 362.1 (M-tert-butyl+H$^+$), Rf (n-heptane:EA=1:1)=0.31.

tert-Butyl 2-[1-ethoxycarbonyl-2-(tetrahydropyran-4-yl)ethyl]-5,5-dioxo-5H-phenothiazine-10-carboxylate

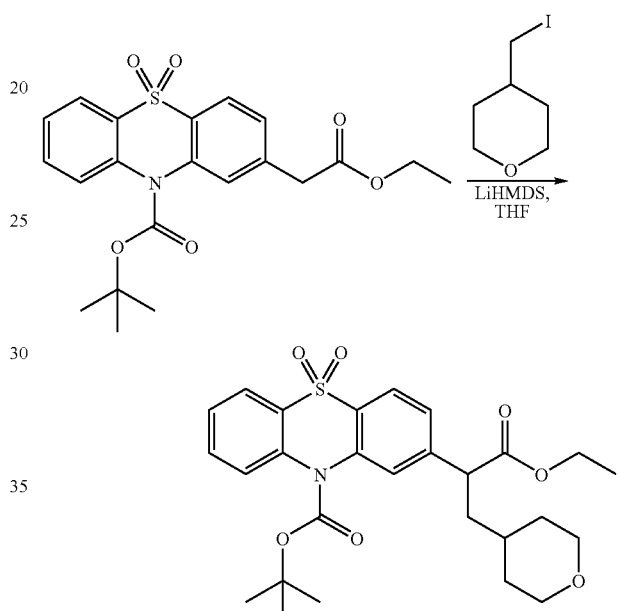

Under argon, 1.31 ml of 1,1,1,3,3,3-hexamethyldisilazane are dissolved in 20 ml of tetrahydrofuran. With ice cooling, 2.3 ml of n-butyllithium (2.5 M in n-hexane) are added dropwise, and the mixture is stirred at 0° C. for another 30 minutes. At −78° C., this solution is then added dropwise to a stirred solution of 2.0 g of tert-butyl 2-ethoxycarbonylmethyl-5,5-dioxo-5H-phenothiazine-10-carboxylate in 100 ml of tetrahydrofuran. The reaction mixture is stirred at −78° C. for 20 minutes, and 1.1 g of 4-(iodomethyl)tetrahydro-2H-pyran are then added dropwise. The cooling bath is removed and the mixture is allowed to slowly warm to room temperature. The reaction mixture is stirred at room temperature overnight. 10 ml of water are then added, the tetrahydrofuran is removed under reduced pressure and the residue is extracted three times with in each case 100 ml of ethyl acetate. The combined organic phases are dried over $MgSO_4$ and then concentrated under reduced pressure. The residue is purified on silica gel using the mobile phase n-heptane:ethyl acetate (100%:0%) =>n-heptane:ethyl acetate (50%:50%). This gives 700 mg of tert-butyl 2-[1-ethoxycarbonyl-2-(tetrahydropyran-4-yl)ethyl]-5,5-dioxo-5H-phenothiazine-10-carboxylate.

C27H33NO7S (515.63), LCMS (ESI): 533.2 (M+NH4$^+$), 460.1 (M-tert-butyl+H$^+$), Rf (n-heptane:EA=1:1)=0.28.

2-(5,5-Dioxo-5,10-dihydrophenothiazin-2-yl)-3-(tetrahydropyran-4-yl)propionic Acid

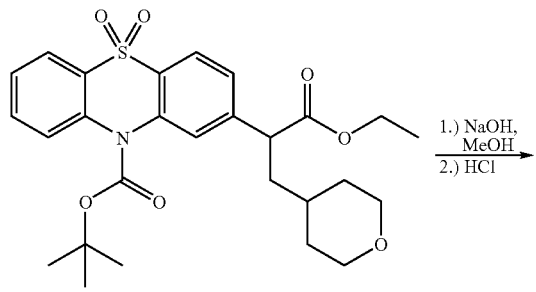

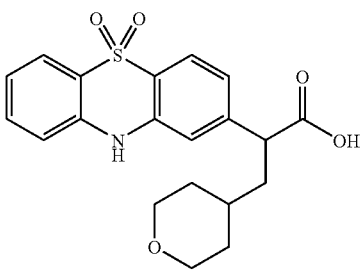

700 mg of tert-butyl 2-[1-ethoxycarbonyl-2-(tetrahydropyran-4-yl)ethyl]-5,5-dioxo-5H-phenothiazine-10-carboxylate are suspended in 50 ml of methanol, and 10 ml of 2 M NaOH solution are added. The reaction mixture is stirred at 60° C. for one hour. The methanol is removed under reduced pressure and the reaction mixture is adjusted to pH 4 by addition of concentrated hydrochloric acid. The mixture is extracted three times with in each case 100 ml of ethyl acetate. The combined organic phases are dried over MgSO$_4$ and then concentrated under reduced pressure. This gives 600 mg of 2-(5,5-dioxo-5,10-dihydrophenothiazin-2-yl)-3-(tetrahydropyran-4-yl)propionic acid. C20H21NO5S (387.46), LCMS (ESI): 388.1 (M+H$^+$).

2-(5,5-Dioxo-5,10-dihydrophenothiazin-2-yl)-N-(1-methyl-1H-pyrazol-3-yl)-3-(tetrahydropyran-4-yl)propionamide

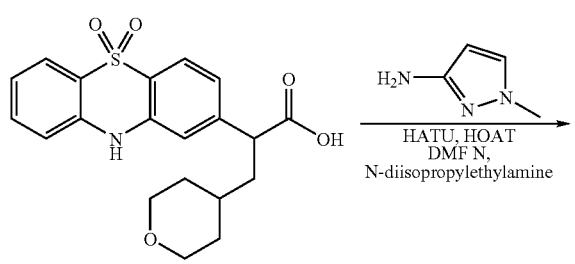

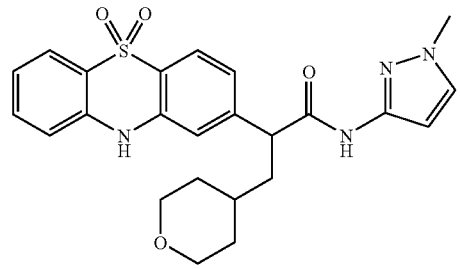

600 mg of 2-(5,5-dioxo-5,10-dihydrophenothiazin-2-yl)-3-(tetrahydropyran-4-yl)propionic acid, 120 mg of commercially available 1-methyl-1H-pyrazole-3-amine and 729 µl of N,N-diisopropylethylamine are dissolved in 5 ml of dimethylformamide. 561 mg of HATU and 200 mg of HOAT are added, and the mixture is stirred at room temperature for two hours. The reaction mixture is then diluted by addition of 200 ml of ethyl acetate and washed three times with in each case 50 ml of water and saturated sodium chloride solution. The organic phase is dried over MgSO$_4$, and the solvent is then removed under reduced pressure. The residue is purified by RP-HPLC. This gives 200 mg of 2-(5,5-dioxo-5,10-dihydrophenothiazin-2-yl)-N-(11-methyl-1H-pyrazol-3-yl)-3-(tetrahydropyran-4-yl)propionamide as a colorless lyophilisate.

C24H26N4O4S (466.17), LCMS (ESI): 467.2 (M+H$^+$).

Example 45

2-(5,5-Dioxo-5,10-dihydrophenothiazin-2-yl)-N-(1-methyl-1H-pyrazol-3-yl)-3-(3-oxo-cyclopentyl)propionamide

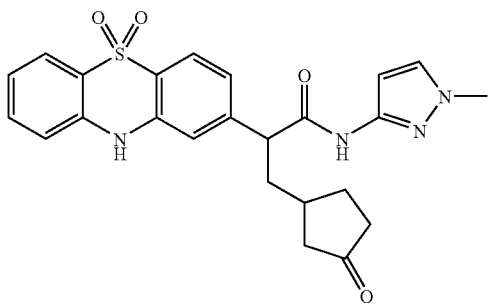

Analogously to Example 36 and Example 44, tert-butyl 2-ethoxycarbonylmethyl-5,5-dioxo-5H-phenothiazine-10-carboxylate, 7-iodomethyl-1,4-dioxaspiro[4.4]nonane and 1-methyl-1H-pyrazole-3-amine give 2-(5,5-dioxo-5,10-dihydrophenothiazin-2-yl)-N-(1-methyl-1H-pyrazol-3-yl)-3-(3-oxocyclopentyl)propionamide.

C24H24N4O4S (464.55), LCMS (ESI): 465.4 (M+H$^+$).

Example 46

2-(5,5-Dioxo-5,10-dihydrophenothiazin-2-yl)-N-(1-methyl-1H-pyrazol-3-yl)-3-((R)-3-oxocyclopentyl)propionamide

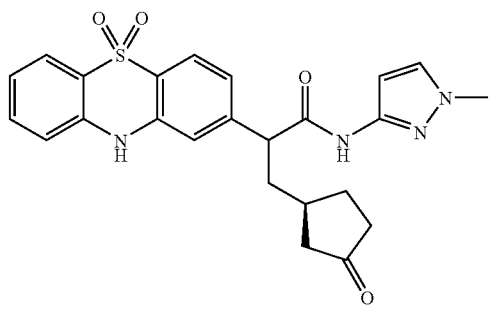

Analogously to Example 36 and Example 44, tert-butyl 2-ethoxycarbonylmethyl-5,5-dioxo-5H-phenothiazine-10-carboxylate, (2R,3R,7S)-7-iodomethyl-2,3-diphenyl-1,4-dioxaspiro[4.4]nonane and 1-methyl-1H-pyrazole-3-amine give 2-(5,5-dioxo-5,10-dihydrophenothiazin-2-yl)-N-(1-methyl-1H-pyrazol-3-yl)-3-((R)-3-oxo-cyclopentyl)propionamide.

C24H24N4O4S (464.55), LCMS (ESI): 465.4 (M+H$^+$).

Example 47

2-(5,5-Dioxo-5,10-dihydrophenothiazin-2-yl)-N-(5-methoxythiazolo[5,4-b]pyridin-2-yl)-3-(3-oxocyclopentyl)propionamide

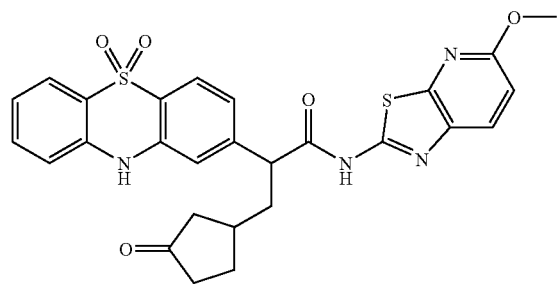

Analogously to Example 36 and Example 44, tert-butyl 2-ethoxycarbonylmethyl-5,5-dioxo-5H-phenothiazine-10-carboxylate, 7-iodomethyl-1,4-dioxaspiro[4.4]nonane and 5-methoxy-thiazolo[5,4-b]pyridin-2-ylamine give 2-(5,5-dioxo-5,10-dihydrophenothiazin-2-yl)-N-(5-methoxythiazolo[5,4-b]pyridin-2-yl)-3-(3-oxo-cyclopentyl)propionamide.

C27H24N4O5S2 (548.64), LCMS (ESI): 549.4 (M+H$^+$).

Example 48

2-(5,5-Dioxo-5,10-dihydrophenothiazin-2-yl)-N-(5-methoxythiazolo[5,4-b]pyridin-2-yl)-3-((R)-3-oxo-cyclopentyl)propionamide

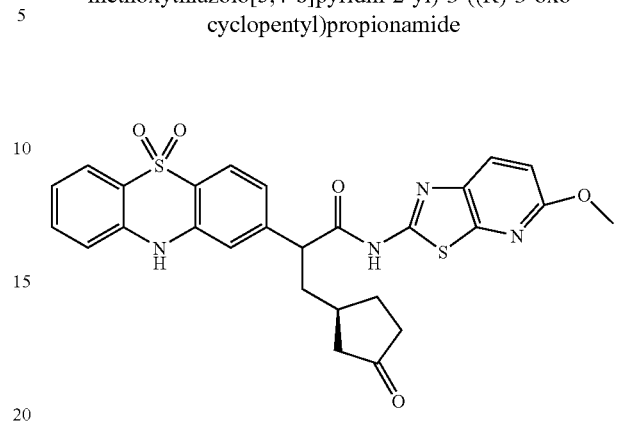

Analogously to Example 36 and Example 44, tert-butyl 2-ethoxycarbonylmethyl-5,5-dioxo-5H-phenothiazine-10-carboxylate, 7(2R,3R,7S)-7-iodomethyl-2,3-diphenyl-1,4-dioxaspiro[4.4]nonane and 5-methoxythiazolo[5,4-b]pyridin-2-ylamine give 2-(5,5-dioxo-5,10-dihydrophenothiazin-2-yl)-N-(5-methoxythiazolo[5,4-b]pyridin-2-yl)-3-((R)-3-oxocyclopentyl)propionamide.

C27H24N4O5S2 (548.64), LCMS (ESI): 549.4 (M+H$^+$).

The diastereomer mixture is separated into the diastereomers on a chiral phase (Chiracel OD-H/74) using the mobile phase n-heptane:ethanol:methanol=4:1.1 (Rt=7.745 min and Rt=9.064 min).

Example 49

N-(1-Benzyl-1H-pyrazol-3-yl)-2-(5,5-dioxo-5,10-dihydrophenothiazin-2-yl)-3-(3-oxo-cyclopentyl)propionamide

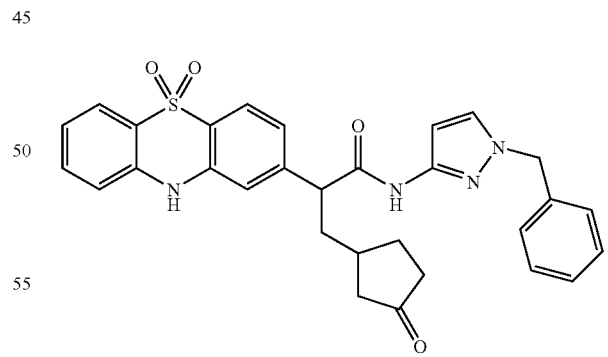

Analogously to Example 36 and Example 44, tert-butyl 2-ethoxycarbonylmethyl-5,5-dioxo-5H-phenothiazine-10-carboxylate, 7-iodomethyl-1,4-dioxaspiro[4.4]nonane and 1-benzyl-1H-pyrazol-3-ylamine give N-(1-benzyl-1H-pyrazol-3-yl)-2-(5,5-dioxo-5,10-dihydrophenothiazin-2-yl)-3-(3-oxocyclopentyl)propionamide. C30H28N4O4S (540.65), LCMS (ESI): 541.44 (M+H$^+$).

Example 50

3-(4,4-Difluorocyclohexyl)-2-(5,5-dioxo-5,10-dihydrophenothiazin-2-yl)-N-(5-methoxy-thiazolo[5,4-b]pyridin-2-yl)propionamide

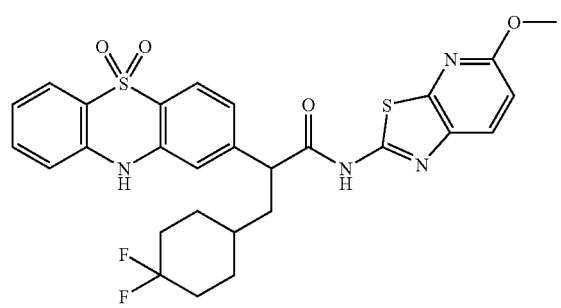

Analogously to Example 36 and Example 44, tert-butyl 2-ethoxycarbonylmethyl-5,5-dioxo-5H-phenothiazine-10-carboxylate, 1,1-difluoro-4-iodomethylcyclohexane (prepared from commercially available ethyl 4,4-difluorocyclohexanecarboxylate analogously to the synthesis of the iodide described in Example 40) and 5-methoxy-thiazolo[5,4-b]pyridin-2-ylamine give 3-(4,4-difluorocyclohexyl)-2-(5,5-dioxo-5,10-dihydrophenothiazin-2-yl)-N-(5-methoxythiazolo[5,4-b]pyridin-2-yl)propionamide.

C28H26F2N4O4S2 (584.67), LCMS (ESI): 585.1 (M+H$^+$), 626.1 (M+MeCN+H$^+$).

Example 51

N-(1-Benzyl-1H-pyrazol-3-yl)-3-(4,4-difluorocyclohexyl)-2-(5,5-dioxo-5,10-dihydrophenothiazin-2-yl)propionamide

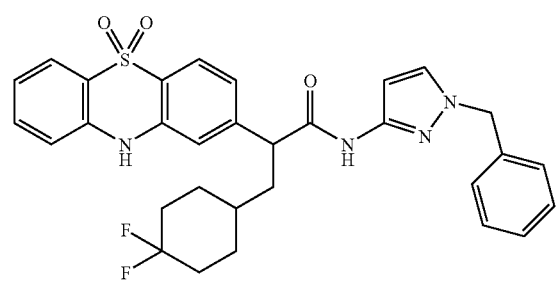

Analogously to Example 36 and Example 44, tert-butyl 2-ethoxycarbonylmethyl-5,5-dioxo-5H-phenothiazine-10-carboxylate, 1,1-difluoro-4-iodomethylcyclohexane (prepared from commercially available ethyl 4,4-difluoro-cyclohexanecarboxylate analogously to the synthesis of the iodide described in Example 40) and 1-benzyl-1H-pyrazole-3-ylamine give N-(1-benzyl-1H-pyrazol-3-yl)-3-(4,4-difluorocyclohexyl)-2-(5,5-dioxo-5,10-dihydrophenothiazin-2-yl)propionamide.

C31H30F2N4O3S (576.67), LCMS (ESI): 577.3 (M+H$^+$).

Example 52

3-(4,4-Difluorocyclohexyl)-2-(5,5-dioxo-5,10-dihydrophenothiazin-2-yl)-N-(1-methyl-1H-pyrazol-3-yl)propionamide

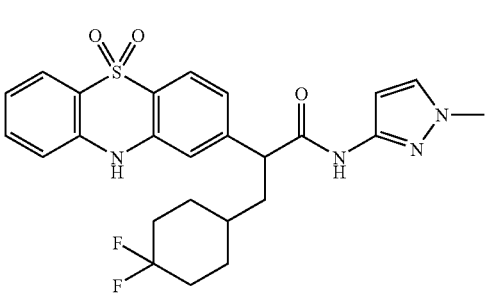

Analogously to Example 36 and Example 44, tert-butyl 2-ethoxycarbonylmethyl-5,5-dioxo-5H-phenothiazine-10-carboxylate, 1,1-difluoro-4-iodomethylcyclohexane (prepared from commercially available ethyl 4,4-difluorocyclohexanecarboxylate analogously to the synthesis of the iodide described in Example 40) and 1-methyl-1H-pyrazol-3-amine give 3-(4,4-difluorocyclohexyl)-2-(5,5-dioxo-5,10-dihydrophenothiazin-2-yl)-N-(1-methyl-1H-pyrazol-3-yl)propionamide.

C25H26F2N4O3S (500.57), LCMS (ESI): 501.2 (M+H$^+$).

Example 53

2-(5,5-Dioxo-5,10-dihydrophenothiazin-2-yl)-3-(4-fluorocyclohex-3-enyl)-N-(5-methoxythiazolo[5,4-b]pyridin-2-yl)propionamide 1-Fluoro-4-iodomethylcyclohexene

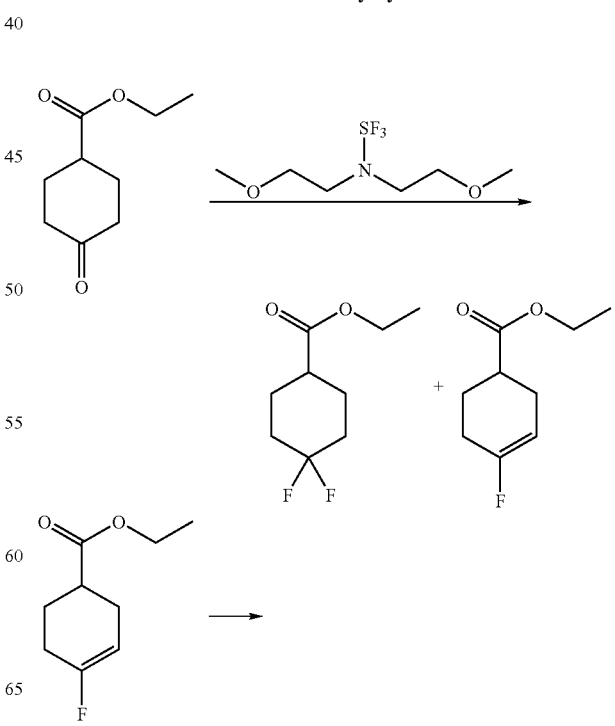

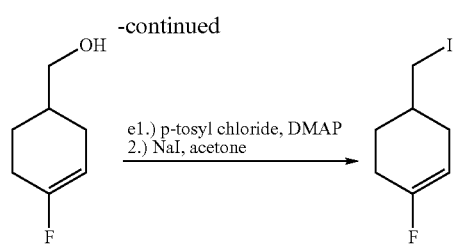

Ethyl 4-fluorocyclohex-3-enecarboxylate

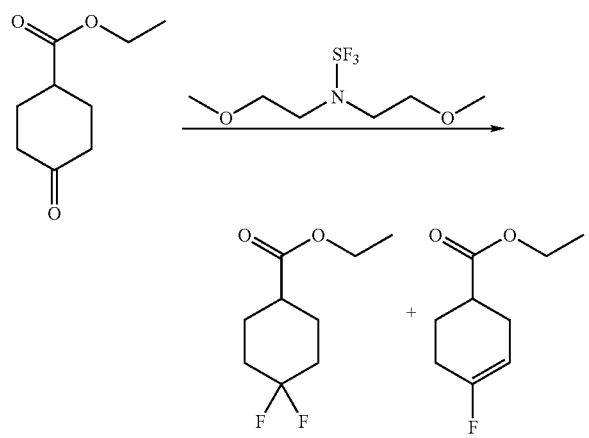

In a Teflon flask and under argon, 4.0 g of ethyl 4-oxocyclohexanecarboxylate are dissolved in 50 ml of dichloromethane. With ice cooling, 13 ml of [bis(2-methoxyethyl)amino]sulfur trifluoride (50% strength solution in toluene) are added. The reaction mixture is stirred at room temperature for twelve hours and then poured onto ice and extracted five times with in each case 100 ml of dichloromethane. The combined organic phases are washed twice with in each case 100 ml of water, dried over MgSO₄ and concentrated under reduced pressure. The resulting residue is purified on silica gel using the mobile phase n-heptane=>n-heptane:ethyl acetate=10:3, and the desired product is separated from the byproduct ethyl 4,4-difluoro-cyclohexanecarboxylate. This gives 726 mg of ethyl 4-fluorocyclohex-3-enecarboxylate.

C9H13FO2 (172.20), GC-MS: 172 (M⁺), Rf (n-heptane:ethyl acetate=4:1)=0.51.

(4-Fluorocyclohex-3-enyl)methanol

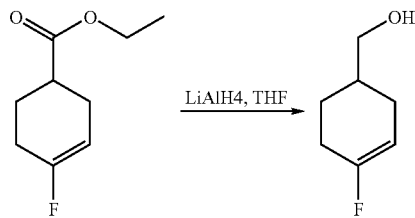

119 mg of lithium aluminum hydride are initially charged in 20 ml of dry tetrahydrofuran and cooled to −20° C. At this temperature, 720 mg of ethyl 4-fluoro-cyclohex-3-enecarboxylate dissolved in 10 ml of tetrahydrofuran are added dropwise under argon. The cooling bath is removed after one hour, and the reaction mixture is stirred for another three hours. The reaction mixture is quenched by addition of 10 ml of water and stirred at room temperature for another two hours. The reaction mixture is filtered and the filtrate is concentrated under reduced pressure. This gives 584 mg of (4-fluorocyclohex-3-enyl)methanol as a colorless oil.

C7H11FO (130.16), Rf (n-heptane:ethyl acetate=2:1)=0.22.

1-Fluoro-4-iodomethylcyclohexene

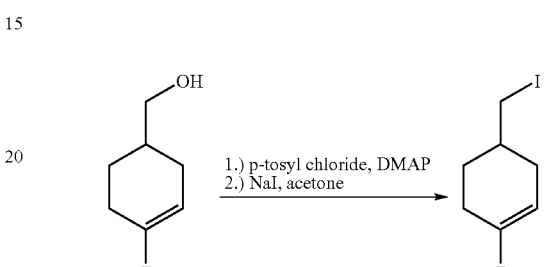

584 mg of (4-fluorocyclohex-3-enyl)methanol are dissolved in 10 ml of dichloromethane, and 610 mg of 4-dimethylaminopyridine and 900 mg of p-toluenesulfonyl chloride are added with ice cooling. The reaction solution is stirred at room temperature for twelve hours and then washed with saturated NaHCO₃ solution and dried over MgSO₄, and the solvent is removed under reduced pressure. The resulting residue is dissolved in 15 ml of acetone, and 2.29 g of sodium iodide are added. The reaction mixture is heated at the boil under reflux for three hours. The solvent is then removed under reduced pressure and the residue is taken up in 100 ml of ethyl acetate and washed twice with in each case 30 ml of water. The organic phase is dried over MgSO₄ and then concentrated under reduced pressure. This gives 696 mg of 1-fluoro-4-iodomethylcyclohexene.

C7H10FI (240.06), Rf (n-heptane:ethyl acetate=4:1)=0.61.

2-(5,5-Dioxo-5,10-dihydrophenothiazin-2-yl)-3-(4-fluorocyclohex-3-enyl)-N-(5-methoxythiazolo[5,4-b]pyridin-2-yl)propionamide

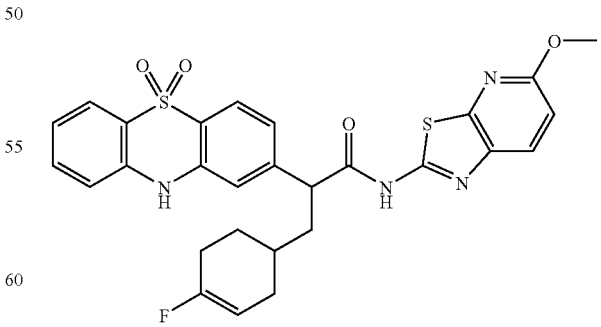

Analogously to Example 36 and Example 44, tert-butyl 2-ethoxycarbonylmethyl-5,5-dioxo-5H-phenothiazine-10-carboxylate, 1-fluoro-4-iodomethylcyclohexene and 5-methoxythiazolo[5,4-b]pyridin-2-ylamine give 2-(5,5-dioxo-5, 10-dihydrophenothiazin-2-yl)-3-(4-fluorocyclohex-3-enyl)-N-(5-methoxythiazolo[5,4-b]pyridin-2-yl)propionamide.

C28H25FN4O4S2 (564.66), LCMS (ESI): 565.2

Example 54

2-(5,5-Dioxo-5,10-dihydrophenothiazin-2-yl)-3-(4-fluorocyclohex-3-enyl)-N-(1-methyl-1H-pyrazol-3-yl)propionamide

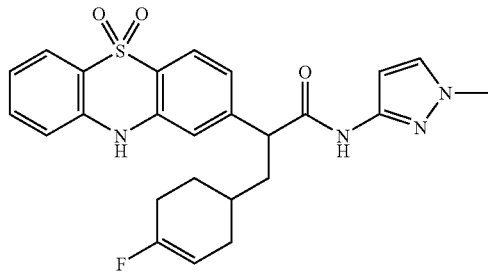

Analogously to Example 36 and Example 44, tert-butyl 2-ethoxycarbonylmethyl-5,5-dioxo-5H-phenothiazine-10-carboxylate, 1-fluoro-4-iodomethylcyclohexene and 1-methyl-1H-pyrazole-3-amine give 2-(5,5-dioxo-5,10-dihydrophenothiazin-2-yl)-3-(4-fluorocyclohex-3-enyl)-N-(1-methyl-1H-pyrazol-3-yl)propionamide.

C25H25FN4O3S (480.57), LCMS (ESI): 481.2

Example 55

3-(3,3-Difluorocyclopentyl)-2-(5,5-dioxo-5,10-dihydrophenothiazin-2-yl)-N-(5-methoxythiazolo[5,4-b]pyridin-2-yl)propionamide 1,1-Difluoro-3-iodomethylcyclopentane

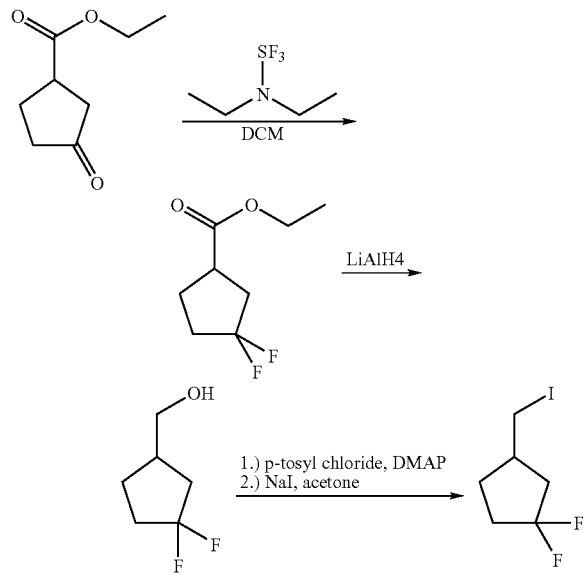

Ethyl 3,3-difluorocyclopentanecarboxylate

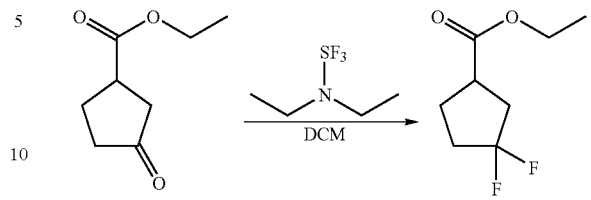

In a Teflon flask and under argon, 1.0 g of ethyl 3-oxocyclopentanecarboxylate is dissolved in 1 ml of dichloromethane. With ice cooling, 0.84 ml of diethylaminosulfur trifluoride are added. The reaction mixture is allowed to slowly warm to room temperature over a period of two hours and stirred at room temperature for another two days. The reaction mixture is then diluted by addition of 100 ml of dichloromethane, washed twice with in each case 50 ml of water, dried over MgSO4 and concentrated under reduced pressure. This gives 1.12 g of ethyl 3,3-difluoro-cyclopentanecarboxylate.

C8H12F2O2 (178.20), GC-MS: 178.0 (M+).

(3,3-Difluorocyclopentyl)methanol

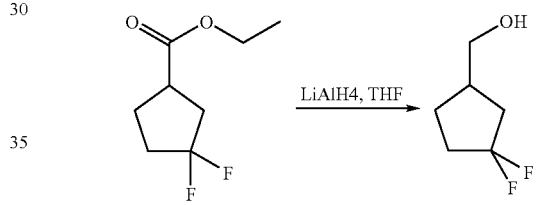

6.4 ml of a 1M solution of lithium aluminum hydride in THF are initially charged in 40 ml of diethyl ether. With ice cooling, 1.12 g of ethyl 3,3-difluoro-cyclopentanecarboxylate dissolved in 10 ml of diethyl ether are added dropwise under argon. After one hour, the cooling bath is removed, and the reaction mixture is stirred for another three hours. The reaction mixture is then poured onto ice-cold saturated ammonium chloride solution and filtered off over a filtration aid. The filtrate is washed with saturated NaHCO3 solution, dried over MgSO4 and concentrated under reduced pressure. This gives 625 mg of (3,3-difluorocyclopentyl)methanol.

C6H10F2O (136.14), GC-MS: 99.0 (M+–F–H2O).

1,1-Difluoro-3-iodomethylcyclopentane

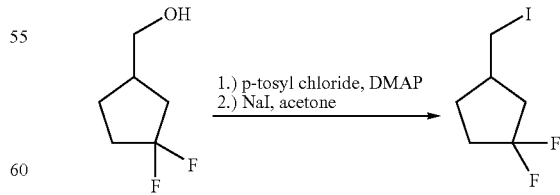

620 mg of (3,3-difluorocyclopentyl)methanol are dissolved in 17 ml of dichloromethane, and 618 mg of 4-dimethylaminopyridine and 911 mg of p-toluenesulfonyl chloride are added with ice cooling. The reaction solution is stirred at room temperature for twelve hours and then washed with saturated NaHCO₃ solution and dried over MgSO₄, and the solvent is removed under reduced pressure. The resulting residue is dissolved in 20 ml of acetone, and 2.32 g of sodium iodide are added. The reaction mixture is heated at the boil under reflux for six hours. The solvent is then removed under reduced pressure, and the residue is taken up in 100 ml of ethyl acetate and washed twice with in each case 30 ml of water. The organic phase is dried over MgSO₄ and then concentrated under reduced pressure. This gives 570 mg of 1,1-difluoro-3-iodomethylcyclopentane.

C6H9F2I (246.04).

3-(3,3-Difluorocyclopentyl)-2-(5,5-dioxo-5,10-dihydrophenothiazin-2-yl)-N-(5-methoxythiazolo[5,4-b]pyridin-2-yl)propionamide

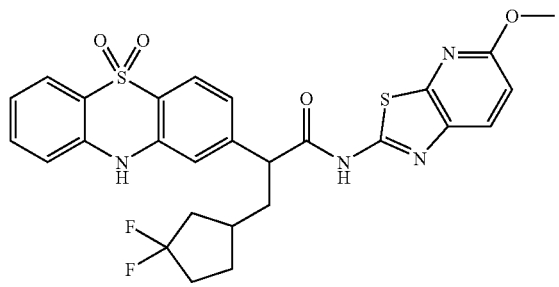

Analogously to Example 36 and Example 44, tert-butyl 2-ethoxycarbonylmethyl-5,5-dioxo-5H-phenothiazine-10-carboxylate, 1,1-difluoro-3-iodomethylcyclopentane and 5-methoxythiazolo[5,4-b]pyridin-2-ylamine give 3-(3,3-difluorocyclopentyl)-2-(5,5-dioxo-5,10-dihydrophenothiazin-2-yl)-N-(5-methoxythiazolo[5,4-b]pyridin-2-yl)propionamide.

C27H24F2N4O4S2 (570.64), LCMS (ESI): 571.2

Example 56

3-(3,3-Difluorocyclopentyl)-2-(5,5-dioxo-5,10-dihydrophenothiazin-2-yl)-N-(1-methyl-1H-pyrazol-3-yl)propionamide

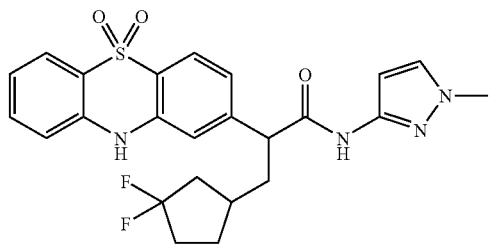

Analogously to Example 36 and Example 44, tert-butyl 2-ethoxycarbonylmethyl-5,5-dioxo-5H-phenothiazine-10-carboxylate, 1,1-difluoro-3-iodomethylcyclopentane and 1-methyl-1H-pyrazole-3-amine give 3-(3,3-difluorocyclopentyl)-2-(5,5-dioxo-5,10-dihydrophenothiazin-2-yl)-N-(1-methyl-1H-pyrazol-3-yl)propionamide.

C24H24F2N4O3S (486.54), LCMS (ESI): 487.2

We claim:
1. A compound of formula I

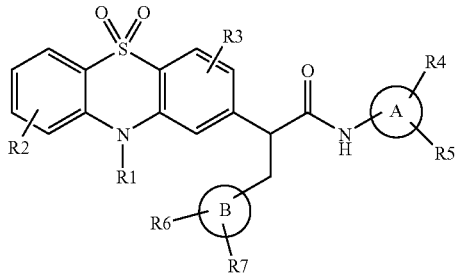

wherein:
R1 is H, (C₁-C₆)-alkyl, (C₀-C₆)-alkylene-aryl, CO—(C₁-C₆)-alkyl, (C₂-C₆)-alkylene-COO—(C₀-C₆)-alkyl, or (C₂-C₆)-alkylene-O—(C₁-C₆)-alkyl;
R2 and R3 independently of one another are H, F, Cl, Br, CN, NO₂, (C₀-C₆)-alkylene-COO—(C₀-C₆)-alkyl, (C₀-C₆)-alkylene-O—(C₀-C₆)-alkyl, (C₁-C₆)-alkyl, (C₀-C₆)-alkylene-CO—(C₁-C₆)-alkyl, (C₀-C₆)-alkylene-phenyl, SCF₃, SF₅, or SCH₃;
R4 and R5 independently of one another are H, F, Cl, Br, CN, SCN, NO₂, =O, (C₀-C₆)-alkylene-COO—(C₀-C₆)-alkyl, —CO—COO—(C₀-C₆)-alkyl, (C₀-C₆)-alkylene-O—(C₀-C₆)-alkyl, (C₁-C₆)-alkyl, (C₀-C₆)-alkylene-CO—(C₁-C₆)-alkyl, (C₀-C₆)-alkylene-CONH(C₀-C₆)-alkyl, (C₀-C₆)-alkylene-CON[(C₀-C₆)-alkyl]₂, (C₀-C₆)-alkylene-NH(C₀-C₆)-alkyl, (C₀-C₆)-alkylene-NH—COO—(C₀-C₆)-alkyl, (C₀-C₆)-alkylene-CON[(C₀-C₆)-alkyl]-O—(C₀-C₆)-alkyl, (C₀-C₆)-alkylene-N[(C₀-C₆)-alkyl]₂, (C₀-C₆)-alkylene-aryl, SF₅, (C₀-C₆)-alkyl-S(O)ₓ(C₁-C₆)-alkyl, S(O)ₓ(C₁-C₆)-alkylene-COO—(C₀-C₆)-alkyl, S(O)ₓ(C₂-C₆)-alkylene-O—(C₀-C₆)-alkyl, —SO₂—NH—(C₀-C₆)-alkyl, —SO₂—N—[(C₀-C₆)-alkyl]₂, S(O)ₓ(C₀-C₆)-alkylene-heterocycle, S(O)ₓ(C₁-C₆)-alkylene-CO-heterocycle, —NH—SO₂—(C₁-C₆)-alkyl, (C₀-C₆)-alkylene-cycloalkyl, (C₀-C₆)-alkylene-heterocycle, or (C₀-C₆)-alkylene-aryl;
x is 0, 1, or 2;
R6 and R7 independently of one another are H, F, Cl, Br, CN, NO₂, =O, =S, =N—O—(C₀-C₆)-alkyl, (C₀-C₆)-alkylene-COO—(C₀-C₆)-alkyl, (C₀-C₆)-alkylene-O—(C₀-C₆)-alkyl, (C₀-C₆)-alkylene-O—CO—(C₁-C₆)-alkyl, (C₁-C₆)-alkyl, (C₀-C₆)-alkylene-CO—(C₁-C₆)-alkyl, (C₀-C₆)-alkylene-aryl, SF₅, or S(O)ₓ—(C₁-C₆)-alkyl;
A is a 5- to 10-membered heterocycle, which may be fused to a further 5- to 10-membered ring; and
B is a 4- to 8-membered cycloalkyl ring, a 4- to 10-membered heterocycle or a 6- to 10-membered aryl ring;
or a physiologically acceptable salt thereof.
2. The compound according to claim 1, wherein
R4 and R5 independently of one another are H, F, Cl, Br, CN, SCN, NO₂, (C₀-C₆)-alkylene-COO—(C₀-C₆)-alkyl, —CO—COO—(C₀-C₆)-alkyl, (C₀-C₆)-alkylene-O—(C₀-C₆)-alkyl, (C₁-C₆)-alkyl, (C₀-C₆)-alkylene-CO—(C₁-C₆)-alkyl, (C₀-C₆)-alkylene-CONH(C₀-C₆)-alkyl, (C₀-C₆)-alkylene-CON[(C₀-C₆)-alkyl]₂, (C₀-C₆)-alkylene-NH(C₀-C₆)-alkyl, (C₀-C₆)-alkylene-NH—COO—(C₀-C₆)-alkyl, (C₀-C₆)-alkylene-CON[(C₀-C₆)-alkyl]-O—(C₀-C₆)-alkyl, (C₀-C₆)-alkylene-N[(C₀-C₆)- alkyl]$_2$, (C$_0$-C$_6$)-alkylene-aryl, SF$_5$, (C$_0$-C$_6$)-alkyl-S(O)$_x$(C$_1$-C$_6$)-alkyl, S(O)$_x$(C$_1$-C$_6$)-alkylene-COO—(C$_0$-C$_6$)-alkyl, S(O)$_x$(C$_2$-C$_6$)-alkylene-O—(C$_0$-C$_6$)-alkyl, —SO$_2$—NH—(C$_0$-C$_6$)-alkyl, —SO$_2$—N—[(C$_0$-C$_6$)-alkyl]$_2$, S(O)$_x$(C$_0$-C$_6$)-alkylene-heterocycle, S(O)$_x$(C$_1$-C$_6$)-alkylene-CO-heterocycle, —NH—SO$_2$—(C$_1$-C$_6$)-alkyl, (C$_0$-C$_6$)-alkylene-cycloalkyl, (C$_0$-C$_6$)-alkylene-heterocycle, or (C$_0$-C$_6$)-alkylene-aryl;

or a physiologically acceptable salt thereof.

3. The compound according to claim 1, wherein

R4 and R5 independently of one another are H, F, Cl, Br, CN, SCN, NO$_2$, (C$_0$-C$_6$)-alkylene-COO—(C$_0$-C$_6$)-alkyl, —CO—COO—(C$_0$-C$_6$)-alkyl, (C$_0$-C$_6$)-alkylene-O—(C$_0$-C$_6$)-alkyl, (C$_1$-C$_6$)-alkyl, (C$_0$-C$_6$)-alkylene-CO—(C$_1$-C$_6$)-alkyl, (C$_0$-C$_6$)-alkylene-CONH(C$_0$-C$_6$)-alkyl, (C$_0$-C$_6$)-alkylene-CON[(C$_0$-C$_6$)-alkyl]$_2$, (C$_0$-C$_6$)-alkylene-NH(C$_0$-C$_6$)-alkyl, (C$_0$-C$_6$)-alkylene-NH—COO—(C$_0$-C$_6$)-alkyl, (C$_0$-C$_6$)-alkylene-CON[(C$_0$-C$_6$)-alkyl]-O—(C$_0$-C$_6$)-alkyl, (C$_0$-C$_6$)-alkylene-N[(C$_0$-C$_6$)-alkyl]$_2$, (C$_0$-C$_6$)-alkylene-aryl, SF$_5$, (C$_0$-C$_6$)-alkyl-S(O)$_x$(C$_1$-C$_6$)-alkyl, S(O)$_x$(C$_1$-C$_6$)-alkylene-COO—(C$_0$-C$_6$)-alkyl, S(O)$_x$(C$_2$-C$_6$)-alkylene-O—(C$_0$-C$_6$)-alkyl, —SO$_2$—NH—(C$_0$-C$_6$)-alkyl, —SO$_2$—N—[(C$_0$-C$_6$)-alkyl]$_2$, S(O)$_x$(C$_0$-C$_6$)-alkylene-heterocycle, S(O)$_x$(C$_1$-C$_6$)-alkylene-CO-heterocycle, —NH—SO$_2$—(C$_1$-C$_6$)-alkyl, (C$_0$-C$_6$)-alkylene-cycloalkyl, (C$_0$-C$_6$)-alkylene-heterocycle, or (C$_0$-C$_6$)-alkylene-aryl; and A is a 5- to 10-membered heterocycle which contains a —C=N— bond in the alpha position, wherein the heterocycle may be fused to a further 5- to 10-membered ring;

or a physiologically acceptable salt thereof.

4. The compound according to claim 1, wherein

R2 and R3 are H;

R4 and R5 independently of one another are H, F, Cl, Br, CN, SCN, NO$_2$, (C$_0$-C$_6$)-alkylene-COO—(C$_0$-C$_6$)-alkyl, —CO—COO—(C$_0$-C$_6$)-alkyl, (C$_0$-C$_6$)-alkylene-O—(C$_0$-C$_6$)-alkyl, (C$_1$-C$_6$)-alkyl, (C$_0$-C$_6$)-alkylene-CO—(C$_1$-C$_6$)-alkyl, (C$_0$-C$_6$)-alkylene-CONH(C$_0$-C$_6$)-alkyl, (C$_0$-C$_6$)-alkylene-CON[(C$_0$-C$_6$)-alkyl]$_2$, (C$_0$-C$_6$)-alkylene-NH(C$_0$-C$_6$)-alkyl, (C$_0$-C$_6$)-alkylene-NH—COO—(C$_0$-C$_6$)-alkyl, (C$_0$-C$_6$)-alkylene-CON[(C$_0$-C$_6$)-alkyl]-O—(C$_0$-C$_6$)-alkyl, (C$_0$-C$_6$)-alkylene-N[(C$_0$-C$_6$)-alkyl]$_2$, (C$_0$-C$_6$)-alkylene-aryl, SF$_5$, (C$_0$-C$_6$)-alkyl-S(O)$_x$(C$_1$-C$_6$)-alkyl, S(O)$_x$(C$_1$-C$_6$)-alkylene-COO—(C$_0$-C$_6$)-alkyl, S(O)$_x$(C$_2$-C$_6$)-alkylene-O—(C$_0$-C$_6$)-alkyl, —SO$_2$—NH—(C$_0$-C$_6$)-alkyl, —SO$_2$—N—[(C$_0$-C$_6$)-alkyl]$_2$, S(O)$_x$(C$_0$-C$_6$)-alkylene-heterocycle, S(O)$_x$(C$_1$-C$_6$)-alkylene-CO-heterocycle, —NH—SO$_2$—(C$_1$-C$_6$)-alkyl, (C$_0$-C$_6$)-alkylene-cycloalkyl, (C$_0$-C$_6$)-alkylene-heterocycle, or (C$_0$-C$_6$)-alkylene-aryl; and A is a 5-membered heterocycle which contains a —C=N— bond in the alpha position, wherein the heterocycle may be fused to a further 5- to 10-membered ring;

or a physiologically acceptable salt thereof.

5. The compound according to claim 1, wherein

R2 and R3 are H;

R4 and R5 independently of one another are H, F, Cl, Br, CN, SCN, NO$_2$, (C$_0$-C$_6$)-alkylene-COO—(C$_0$-C$_6$)-alkyl, —CO—COO—(C$_0$-C$_6$)-alkyl, (C$_0$-C$_6$)-alkylene-O—(C$_0$-C$_6$)-alkyl, (C$_1$-C$_6$)-alkyl, (C$_0$-C$_6$)-alkylene-CO—(C$_1$-C$_6$)-alkyl, (C$_0$-C$_6$)-alkylene-CONH(C$_0$-C$_6$)-alkyl, (C$_0$-C$_6$)-alkylene-CON[(C$_0$-C$_6$)-alkyl]$_2$, (C$_0$-C$_6$)-alkylene-NH(C$_0$-C$_6$)-alkyl, (C$_0$-C$_6$)-alkylene-NH—COO—(C$_0$-C$_6$)-alkyl, (C$_0$-C$_6$)-alkylene-CON[(C$_0$-C$_6$)-alkyl]-O—(C$_0$-C$_6$)-alkyl, (C$_0$-C$_6$)-alkylene-N[(C$_0$-C$_6$)-alkyl]$_2$, (C$_0$-C$_6$)-alkylene-aryl, SF$_5$, (C$_0$-C$_6$)-alkyl-S(O)$_x$(C$_1$-C$_6$)-alkyl, S(O)$_x$(C$_1$-C$_6$)-alkylene-COO—(C$_0$-C$_6$)-alkyl, S(O)$_x$(C$_2$-C$_6$)-alkylene-O—(C$_0$-C$_6$)-alkyl, —SO$_2$—NH—(C$_0$-C$_6$)-alkyl, —SO$_2$—N—[(C$_0$-C$_6$)-alkyl]$_2$, S(O)$_x$(C$_0$-C$_6$)-alkylene-heterocycle, S(O)$_x$(C$_1$-C$_6$)-alkylene-CO-heterocycle, —NH—SO$_2$—(C$_1$-C$_6$)-alkyl, (C$_0$-C$_6$)-alkylene-cycloalkyl, (C$_0$-C$_6$)-alkylene-heterocycle, or (C$_0$-C$_6$)-alkylene-aryl;

A is thiazol-2-yl, pyrazol-3-yl, pyridin-2-yl, oxazol-2-yl, isoxazol-3-yl, imidazol-2-yl, [1,2,4]thiadiazol-3-yl, [1,2,4]thiadiazol-5-yl, [1,3,4]thiadiazol-3-yl, pyridin-2-yl, pyrimidin-2-yl, pyrimidin-4-yl, pyrazin-2-yl, pyridazin-2-yl, [1,2,4]triazin-3-yl, [1,2,4]triazin-6-yl, thiazolo[4,5-b]pyridin-2-yl, thieno[2,3-d]thiazol-2-yl, benzothiazol-2-yl, benzoxazol-2-yl, benzimidazol-2-yl, quinolin-2-yl, isoquinolin-3-yl, 4,5,6,7-tetrahydro-benzothiazol-2-yl, 4,5,6,7-tetrahydrobenzoxazol-2-yl, 4,5,6,7-tetrahydro-benzimidazol-2-yl, 4,5,6,7-tetrahydro-pyrazolo[1,5-a]pyridin-2-yl, 5,6-dihydro-4H-cyclopentathiazol-2-yl, or 4,5-dihydrothiazol-2-yl; and B is cyclopentyl, cyclohexyl, tetrahydrofuranyl, tetrahydropyranyl, tetrahydrothiopyranyl, piperidinyl, phenyl, pyridyl, furanyl, thiophenyl, thiazolyl, oxazolyl, pyrazolyl, or isoxazolyl;

or a physiologically acceptable salt thereof.

6. The compound according to claim 1, wherein

R1 is H or (C$_1$-C$_6$)-alkyl;

R2 and R3 are H;

R4 is H, F, Cl, Br, (C$_0$-C$_6$)-alkylene-COO—(C$_0$-C$_6$)-alkyl, (C$_0$-C$_6$)-alkylene-O—(C$_0$-C$_6$)-alkyl, =O, (C$_1$-C$_6$)-alkyl, or (C$_0$-C$_6$)-alkylene-aryl;

R5 is H;

R6 is H;

R7 is H, F, Cl, Br, =O, =N—O—(C$_0$-C$_6$)-alkyl, or (C$_1$-C$_6$)-alkyl;

A is thiazol-2-yl, pyrazol-3-yl, isoxazol-3-yl, [1,2,4]thiadiazol-3-yl, [1,2,4]thiadiazol-5-yl, [1,3,4]thiadiazol-3-yl, pyridazin-2-yl, thiazolo[4,5-b]pyridin-2-yl, or thieno[2,3-d]thiazol-2-yl; and B is cyclopentyl, cyclohexyl, cyclohexenyl, tetrahydrofuranyl, tetrahydropyranyl, tetrahydrothiophenyl, oxetanyl, piperidinyl, or indanyl;

or a physiologically acceptable salt thereof.

7. The compound according to claim 1, wherein

R1 is (C$_1$-C$_6$)-alkyl;

R2 and R3 are H;

R4 is H, F, Cl, Br, (C$_0$-C$_6$)-alkylene-COO—(C$_0$-C$_6$)-alkyl, (C$_0$-C$_6$)-alkylene-O—(C$_0$-C$_6$)-alkyl, =O, (C$_1$-C$_6$)-alkyl, or (C$_0$-C$_6$)-alkylene-aryl;

R5 is H;

R6 is H;

R7 is H, F, Cl, Br, =O, =N—O—(C$_0$-C$_6$)-alkyl, or (C$_1$-C$_6$)-alkyl;

A is thiazol-2-yl, pyrazol-3-yl, isoxazol-3-yl, [1,2,4]thiadiazol-3-yl, [1,2,4]thiadiazol-5-yl, [1,3,4]thiadiazol-3-yl, pyridazin-2-yl, thiazolo[4,5-b]pyridin-2-yl, or thieno[2,3-d]thiazol-2-yl; and B is cyclopentyl, cyclohexyl, cyclohexenyl, tetrahydrofuranyl, tetrahydropyranyl, tetrahydrothiophenyl, oxetanyl, piperidinyl, or indanyl;

or a physiologically acceptable salt thereof.

8. A pharmaceutical composition comprising at least one compound according to claim 1 or a physiologically acceptable salt thereof, in combination with a pharmaceutically acceptable carrier or excipient.

9. A pharmaceutical composition comprising at least one compound according to claim 2 or a physiologically acceptable salt thereof, in combination with a pharmacologically acceptable carrier or excipient.

10. A pharmaceutical composition comprising at least one compound according to claim 3 or a physiologically acceptable salt thereof, in combination with a pharmacologically acceptable carrier or excipient.

11. A pharmaceutical composition comprising at least one compound according to claim 4 or a physiologically acceptable salt thereof, in combination with a pharmacologically acceptable carrier or excipient.

12. A pharmaceutical composition comprising at least one compound according to claim 5 or a physiologically acceptable salt thereof, in combination with a pharmacologically acceptable carrier or excipient.

13. A pharmaceutical composition comprising at least one compound according to claim 6 or a physiologically acceptable salt thereof, in combination with a pharmacologically acceptable carrier or excipient.

14. A pharmaceutical composition comprising at least one compound according to claim 7 or a physiologically acceptable salt thereof, in combination with a pharmacologically acceptable carrier or excipient.

15. The pharmaceutical composition according to claim 8, comprising at least one further active ingredient.

16. The pharmaceutical composition according to claim 9, wherein the further active ingredient is selected from antidiabetics, hypoglycemic active ingredients, HMGCOA reductase inhibitors, cholesterol absorption inhibitors, PPAR gamma agonists, PPAR alpha agonists, PPAR alpha/gamma agonists, PPAR delta agonists, fibrates, MTP inhibitors, bile acid absorption inhibitors, CETP inhibitors, polymeric bile acid adsorbents, LDL receptor inducers, ACAT inhibitors, antioxidants, lipoprotein lipase inhibitors, ATP-citrate lyase inhibitors, squalene synthetase inhibitors, lipoprotein(a) antagonists, HM74A receptor agonists, lipase inhibitors, insulins, sulfonylureas, biguanides, meglitinides, thiazolidinediones, α-glucosidase inhibitors, active ingredients which act on the ATP-dependent potassium channel of the beta cells, glycogen phosphorylase inhibitors, glucagon receptor antagonists, activators of glucokinase, inhibitors of gluconeogenesis, inhibitors of fructose-1,6-biphosphatase, modulators of glucose transporter 4, inhibitors of glutamine-fructose-6-phosphate amidotransferase, inhibitors of dipeptidylpeptidase IV, inhibitors of 11-beta-hydroxysteroid dehydrogenase 1, inhibitors of protein tyrosine phosphatase 1B, modulators of the sodium-dependent glucose transporter 1, modulators of the sodium-dependent glucose transporter 2, GPR40 modulators, inhibitors of hormone-sensitive lipase, inhibitors of acetyl-CoA carboxylase, inhibitors of phosphoenolpyruvate carboxykinase, inhibitors of glycogen synthase kinase-3 beta, inhibitors of protein kinase C beta, endothelin-A receptor antagonists, inhibitors of I kappaB kinase, modulators of glucocorticoid receptor, CART agonists, NPY agonists, MC4 agonists, orexin agonists, H3 agonists, TNF agonists, CRF agonists, CRF BP antagonists, urocortin agonists, β3 agonists, CB1 receptor antagonists, MSH agonists, CCK agonists, serotonin reuptake inhibitors, mixed serotoninergic and noradrenergic compounds, 5HT agonists, bombesin agonists, galanin antagonists, human growth hormones, growth hormone-releasing compounds, TRH agonists, uncoupling protein 2 modulators, uncoupling protein 3 modulators, leptin agonists, DA agonists, bromocriptine, Doprexin, lipase/amylase inhibitors, PPAR modulators, RXR modulators, TR-β agonists, and amphetamines.

17. A method for treating type-2 diabetes, schizophrenia, or for lowering blood glucose level lowering blood glucose level, in a patient in need thereof, comprising administering to the patient a pharmaceutically effective amount of the compound according to claim 1, or a physiologically acceptable salt thereof.

18. A method for manufacturing a pharmaceutical composition comprising at least one compound according to claim 1 or a physiologically acceptable salt thereof, in combination with a pharmaceutically acceptable carrier or excipient, comprising mixing the compound according to claim 1 or the physiologically acceptable salt thereof with the pharmaceutically acceptable carrier or excipient, and converting this mixture into a form suitable for administration.

* * * * *